(12) United States Patent
Boeke et al.

(10) Patent No.: US 11,661,589 B2
(45) Date of Patent: *May 30, 2023

(54) COMPOSITIONS AND METHODS FOR CONTROLLING MICROBIAL GROWTH

(71) Applicants: New York University, New York, NY (US); The Johns Hopkins University, Baltimore, MD (US)

(72) Inventors: Jef D. Boeke, New York, NY (US); Neta Agmon, New York, NY (US); Yizhi Cai, Edinburgh (GB)

(73) Assignees: New York University, New York, NY (US); The Johns Hopkins University, Baitimore, MD (US)

( * ) Notice: Subject to any disclaimer, the term of this patent is extended or adjusted under 35 U.S.C. 154(b) by 1112 days.

This patent is subject to a terminal disclaimer.

(21) Appl. No.: 16/113,671

(22) Filed: Aug. 27, 2018

(65) Prior Publication Data
US 2020/0024582 A1    Jan. 23, 2020

Related U.S. Application Data

(63) Continuation of application No. 15/000,640, filed on Jan. 19, 2016, now Pat. No. 10,059,927.

(60) Provisional application No. 62/105,112, filed on Jan. 19, 2015.

(51) Int. Cl.
*C12N 9/12*    (2006.01)
(52) U.S. Cl.
CPC ........ *C12N 9/1241* (2013.01); *C12N 2510/00* (2013.01); *C12Y 207/07* (2013.01)
(58) Field of Classification Search
None
See application file for complete search history.

(56) References Cited

U.S. PATENT DOCUMENTS 10,059,927 B2 * 8/2018 Boeke ................. C12N 9/1241

OTHER PUBLICATIONS

Cai et al. Intrinsic biocontainment: Multiplex genome safeguards combine transcriptional and recombinational control of essential yeast genes. PNAS. Published Jan. 26, 2015. PNAS. 6 pages. (Year: 2015).*
Hayashi et al. Ubc9 Is Essential for Viability of Higher Eukaryotic Cells. 2002. Experimental Cell Research. vol. 280, p. 212-221. (Year: 2002).*
Lindstrom et al. The Mother Enrichment Program: A Genetic System for Facile Replicative Life Span Analysis in *Saccharomyces cerevisiae*. 2009. Genetics. vol. 183, p. 413-422. (Year: 2009).*

* cited by examiner

*Primary Examiner* — Nancy J Leith
(74) *Attorney, Agent, or Firm* — Hodgson Russ LLP

(57) ABSTRACT

Provided are modified microorganisms which are modified such that their growth can be controlled using exogenously provided compounds. The microorganisms can be modified by genetic alterations that include a promoter inducible by a first exogenously supplied compound. The promoter can be configured to drive expression of an RNA coding sequence that may be essential to growth of the microorganism. The microorganisms may also be modified to include site specific recombinase recognition sites flanking or within the RNA coding sequence so that expression of the corresponding site specific recombinase will disrupt transcription of the RNA. The site specific recombinase can be configured such that it expression and/or activity is suppressed by a second exogenously supplied compound. Methods of making the modified microorganisms and kits that contain reagents for making and using the modified microorganisms are also provided.

11 Claims, 28 Drawing Sheets
(26 of 28 Drawing Sheet(s) Filed in Color)
Specification includes a Sequence Listing.

Figure 9, continued
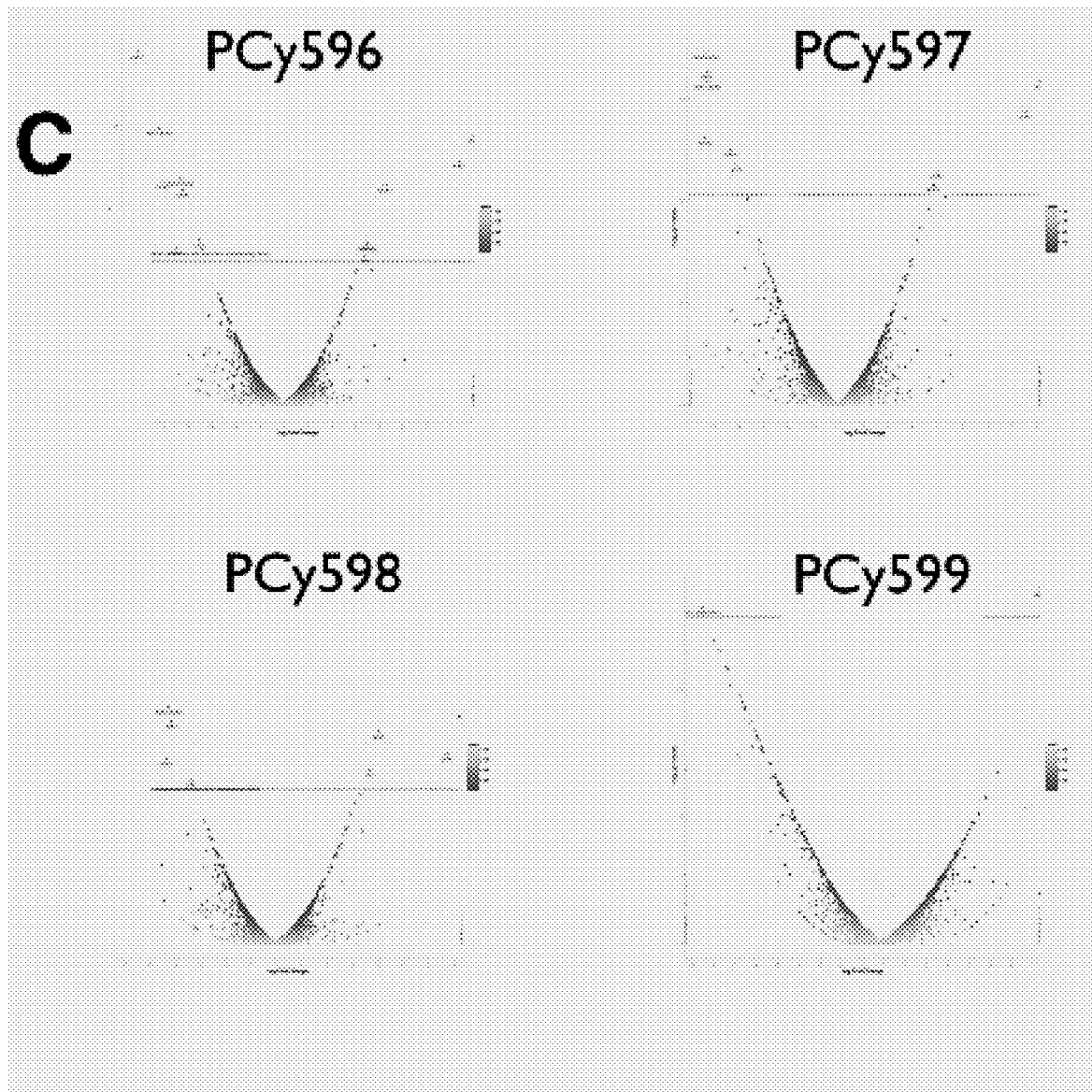

Figure 14, continued
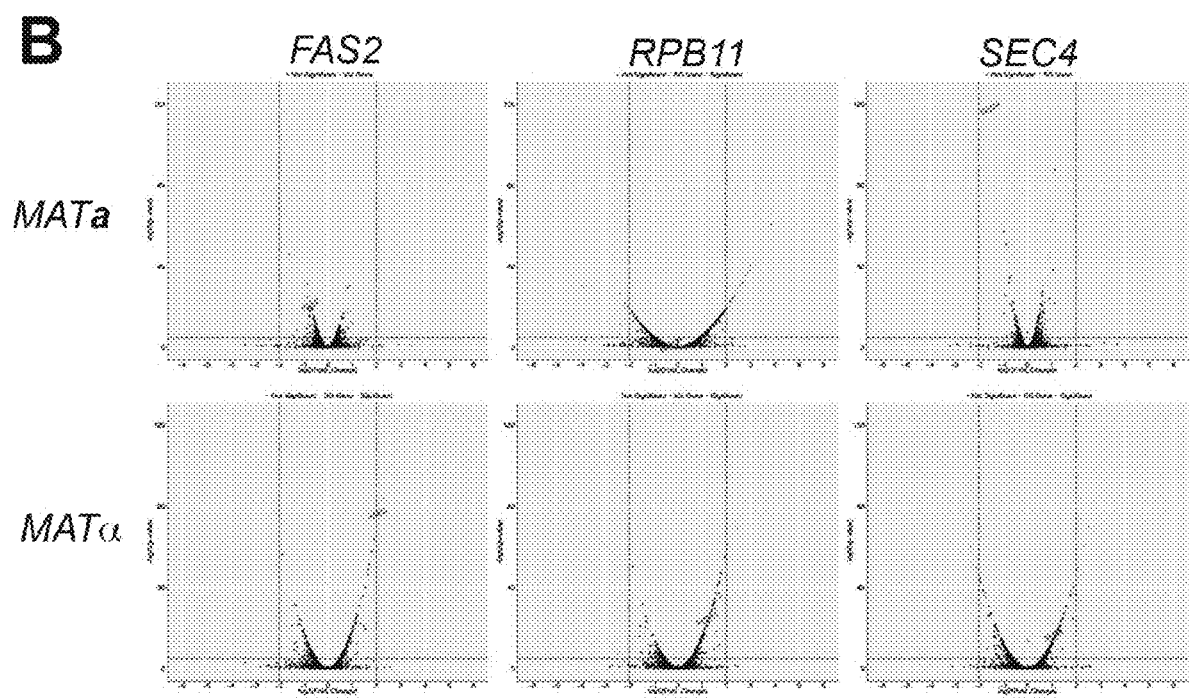

Figure 14, continued
C
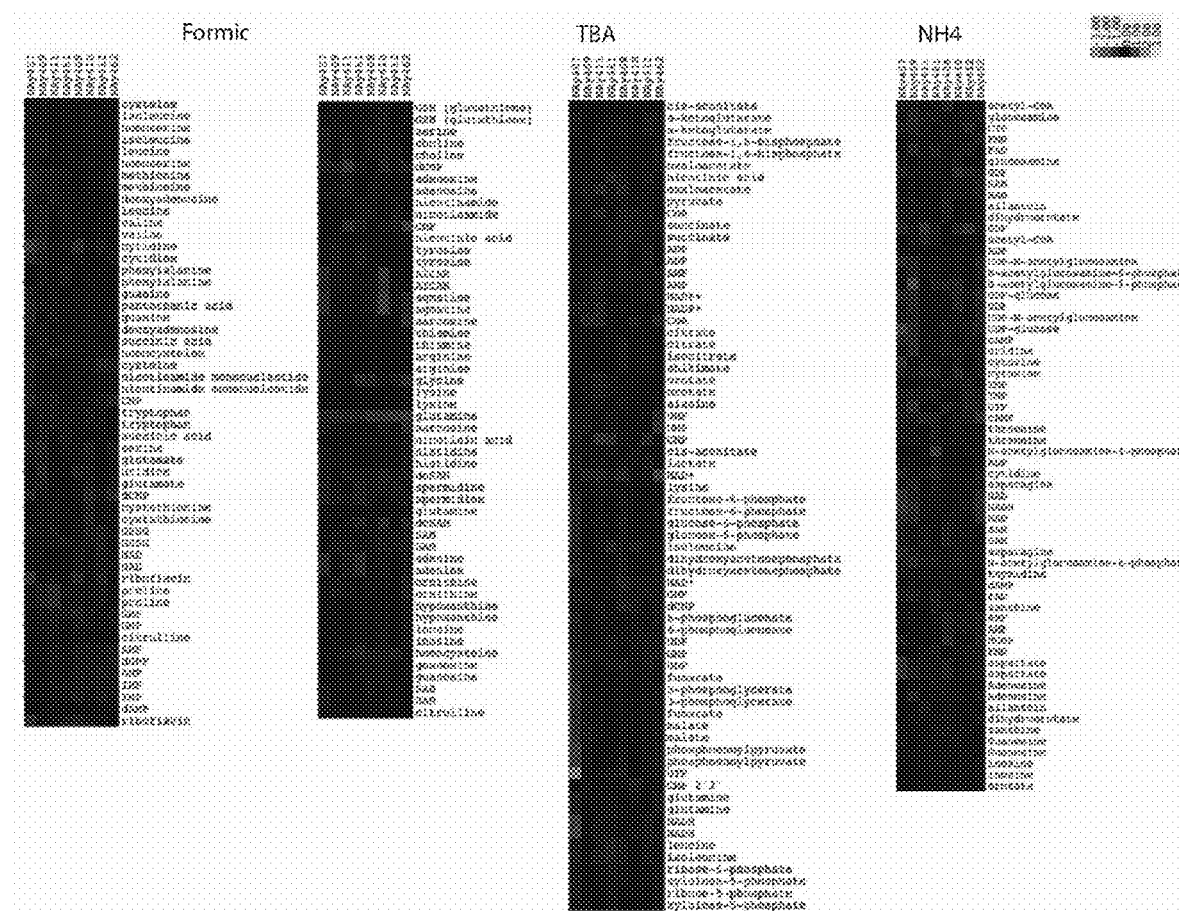

Figure 16, Continued
D
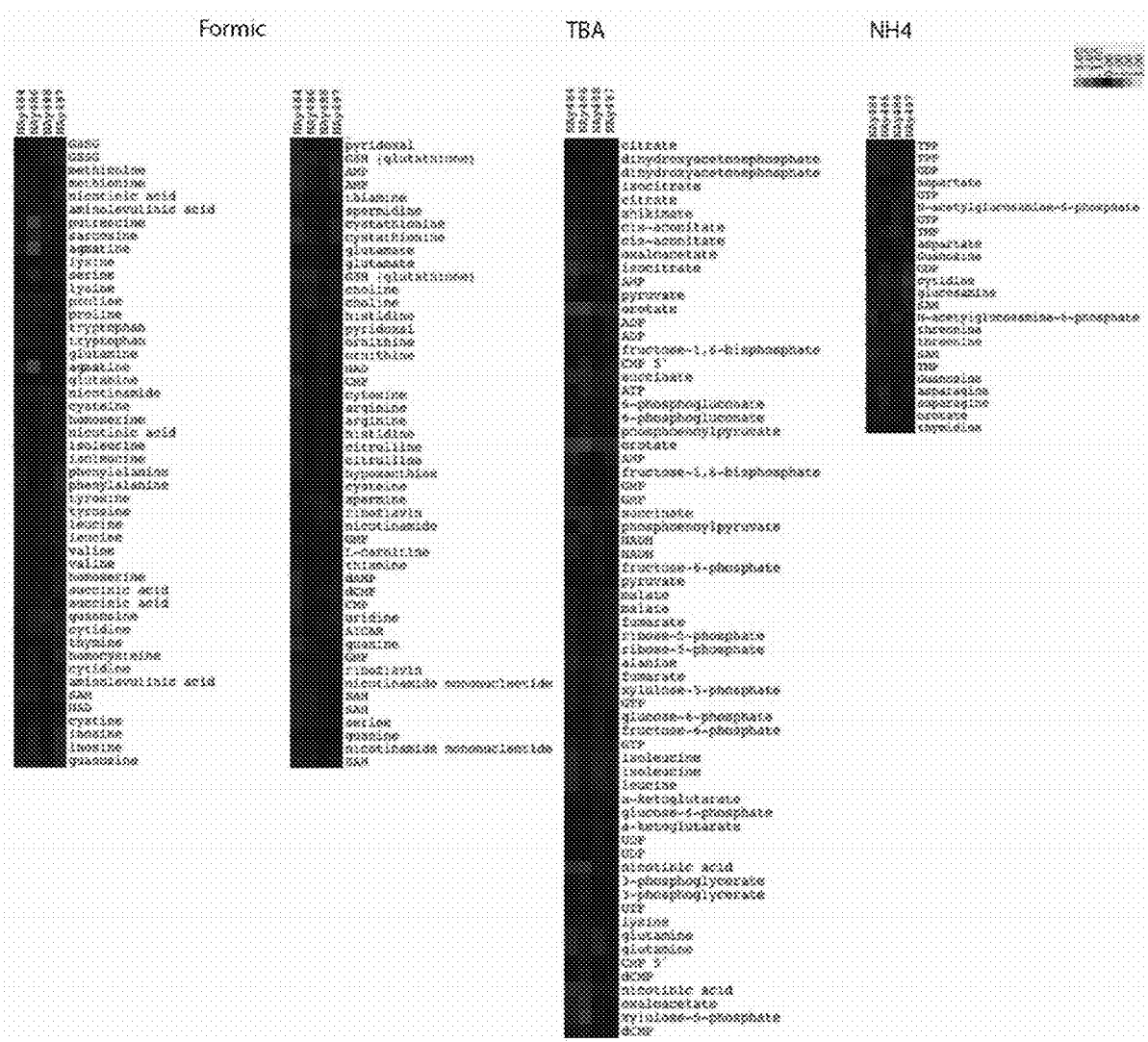

FIGURE 23

SEQUENCE LISTING

<160> NUMBER OF SEQ ID NOS: 108

<210> SEQ ID NO 1
<211> LENGTH: 16
<212> TYPE: DNA
<213> ORGANISM: artificial sequence
<220> FEATURE:
<223> OTHER INFORMATION: primer

<400> SEQUENCE: 1
gtaaaacgac ggccag        16

<210> SEQ ID NO 2
<211> LENGTH: 17
<212> TYPE: DNA
<213> ORGANISM: artificial sequence
<220> FEATURE:
<223> OTHER INFORMATION: primer

<400> SEQUENCE: 2
caggaaacag ctatgac        17

<210> SEQ ID NO 3
<211> LENGTH: 60
<212> TYPE: DNA
<213> ORGANISM: artificial sequence
<220> FEATURE:
<223> OTHER INFORMATION: primer

<400> SEQUENCE: 3
gaaggttaat gtggctgtgg tttcagggtc cataaagctt gtcctggaag tctcatggag        60

<210> SEQ ID NO 4
<211> LENGTH: 34

<212> TYPE: DNA
<213> ORGANISM: artificial sequence
<220> FEATURE:
<223> OTHER INFORMATION: primer

<400> SEQUENCE: 4
tcaggatccc taggttcctt tgttacttct tccg                           34

<210> SEQ ID NO 5
<211> LENGTH: 36
<212> TYPE: DNA
<213> ORGANISM: artificial sequence
<220> FEATURE:
<223> OTHER INFORMATION: primer

<400> SEQUENCE: 5
ggtctcacag tgaaggttaa tgtggctgtg gtttca                         36

<210> SEQ ID NO 6
<211> LENGTH: 29
<212> TYPE: DNA
<213> ORGANISM: artificial sequence
<220> FEATURE:
<223> OTHER INFORMATION: primer

<400> SEQUENCE: 6
ggtctcacat tattattctc gactcaact                                 29

<210> SEQ ID NO 7
<211> LENGTH: 20
<212> TYPE: DNA
<213> ORGANISM: artificial sequence
<220> FEATURE:
<223> OTHER INFORMATION: primer

<400> SEQUENCE: 7
gtacagatgc tccatgcctt                                           20

<210> SEQ ID NO 8
<211> LENGTH: 20
<212> TYPE: DNA
<213> ORGANISM: artificial sequence
<220> FEATURE:
<223> OTHER INFORMATION: primer

<400> SEQUENCE: 8
aagaatgagc caagacttgc                                           20

<210> SEQ ID NO 9
<211> LENGTH: 21
<212> TYPE: DNA
<213> ORGANISM: artificial sequence
<220> FEATURE:
<223> OTHER INFORMATION: primer

<400> SEQUENCE: 9
ggatcatact cggaatagag t                                         21

<210> SEQ ID NO 10
<211> LENGTH: 20
<212> TYPE: DNA
<213> ORGANISM: artificial sequence
<220> FEATURE:
<223> OTHER INFORMATION: primer

<400> SEQUENCE: 10

```
cgaactaata ctgtagccct                                                   20

<210> SEQ ID NO 11
<211> LENGTH: 75
<212> TYPE: DNA
<213> ORGANISM: artificial sequence
<220> FEATURE:
<223> OTHER INFORMATION: oligonucleotide

<400> SEQUENCE: 11
cccccctcga ggtcgacggt atcgataagc ttgatatcga attcctgcag tggtttacca      60
ctaacaagaa aagaa                                                        75

<210> SEQ ID NO 12
<211> LENGTH: 75
<212> TYPE: DNA
<213> ORGANISM: artificial sequence
<220> FEATURE:
<223> OTHER INFORMATION: oligonucleotide

<400> SEQUENCE: 12
cccccctcga ggtcgacggt atcgataagc ttgatatcga attcctgcag tgcatatata      60
ccgggtgagg gccac                                                        75

<210> SEQ ID NO 13
<211> LENGTH: 75
<212> TYPE: DNA
<213> ORGANISM: artificial sequence
<220> FEATURE:
<223> OTHER INFORMATION: oligonucleotide

<400> SEQUENCE: 13
cccccctcga ggtcgacggt atcgataagc ttgatatcga attcctgcag tttttaaaaa      60
aagttgcatt atttc                                                        75

<210> SEQ ID NO 14
<211> LENGTH: 75
<212> TYPE: DNA
<213> ORGANISM: artificial sequence
<220> FEATURE:
<223> OTHER INFORMATION: oligonucleotide

<400> SEQUENCE: 14
cccccctcga ggtcgacggt atcgataagc ttgatatcga attcctgcag tcttgcgaga      60
tgatcccgca ttttc                                                        75

<210> SEQ ID NO 15
<211> LENGTH: 75
<212> TYPE: DNA
<213> ORGANISM: artificial sequence
<220> FEATURE:
<223> OTHER INFORMATION: oligonucleotide

<400> SEQUENCE: 15
cccccctcga ggtcgacggt atcgataagc ttgatatcga attcctgcag gtcacaggtg      60
tcaaggtgtt aactc                                                        75

<210> SEQ ID NO 16
<211> LENGTH: 75
<212> TYPE: DNA
<213> ORGANISM: artificial sequence
<220> FEATURE:
<223> OTHER INFORMATION: oligonucleotide
```

<400> SEQUENCE: 16
cccccctcga ggtcgacggt atcgataagc ttgatatcga attcctgcag tgagcgtggt  60
tcagggcact ctacg  75

<210> SEQ ID NO 17
<211> LENGTH: 75
<212> TYPE: DNA
<213> ORGANISM: artificial sequence
<220> FEATURE:
<223> OTHER INFORMATION: oligonucleotide

<400> SEQUENCE: 17
cccccctcga ggtcgacggt atcgataagc ttgatatcga attcctgcag actaccactg  60
cctcccttcg tatac  75

<210> SEQ ID NO 18
<211> LENGTH: 75
<212> TYPE: DNA
<213> ORGANISM: artificial sequence
<220> FEATURE:
<223> OTHER INFORMATION: oligonucleotide

<400> SEQUENCE: 18
cccccctcga ggtcgacggt atcgataagc ttgatatcga attcctgcag acgagatcat  60
tttcttatct atcta  75

<210> SEQ ID NO 19
<211> LENGTH: 75
<212> TYPE: DNA
<213> ORGANISM: artificial sequence
<220> FEATURE:
<223> OTHER INFORMATION: oligonucleotide

<400> SEQUENCE: 19
cccccctcga ggtcgacggt atcgataagc ttgatatcga attcctgcag aactattttc  60
tatatttcta ttcta  75

<210> SEQ ID NO 20
<211> LENGTH: 75
<212> TYPE: DNA
<213> ORGANISM: artificial sequence
<220> FEATURE:
<223> OTHER INFORMATION: oligonucleotide

<400> SEQUENCE: 20
cccccctcga ggtcgacggt atcgataagc ttgatatcga attcctgcag ttgttgcgca  60
ctaggtacga tttcc  75

<210> SEQ ID NO 21
<211> LENGTH: 75
<212> TYPE: DNA
<213> ORGANISM: artificial sequence
<220> FEATURE:
<223> OTHER INFORMATION: oligonucleotide

<400> SEQUENCE: 21
cccccctcga ggtcgacggt atcgataagc ttgatatcga attcctgcag tattttatta  60
cggttcagca aaggc  75

<210> SEQ ID NO 22

```
<211> LENGTH: 75
<212> TYPE: DNA
<213> ORGANISM: artificial sequence
<220> FEATURE:
<223> OTHER INFORMATION: oligonucleotide

<400> SEQUENCE: 22
cccccctcga ggtcgacggt atcgataagc ttgatatcga attcctgcag acagatcctt     60
tataatgtag taatt                                                      75

<210> SEQ ID NO 23
<211> LENGTH: 75
<212> TYPE: DNA
<213> ORGANISM: artificial sequence
<220> FEATURE:
<223> OTHER INFORMATION: oligonucleotide

<400> SEQUENCE: 23
aaaagctgga gctccaccgc ggtggcggcc gctctagaac tagtggatcc aaaatccgta     60
agccaaaaaa acaag                                                      75

<210> SEQ ID NO 24
<211> LENGTH: 75
<212> TYPE: DNA
<213> ORGANISM: artificial sequence
<220> FEATURE:
<223> OTHER INFORMATION: oligonucleotide

<400> SEQUENCE: 24
aaaagctgga gctccaccgc ggtggcggcc gctctagaac tagtggatcc agagagggcg     60
ttgttcctcc tgtag                                                      75

<210> SEQ ID NO 25
<211> LENGTH: 75
<212> TYPE: DNA
<213> ORGANISM: artificial sequence
<220> FEATURE:
<223> OTHER INFORMATION: oligonucleotide

<400> SEQUENCE: 25
aaaagctgga gctccaccgc ggtggcggcc gctctagaac tagtggatcc gaacgtttgg     60
ggcttgacgg ctcga                                                      75

<210> SEQ ID NO 26
<211> LENGTH: 75
<212> TYPE: DNA
<213> ORGANISM: artificial sequence
<220> FEATURE:
<223> OTHER INFORMATION: oligonucleotide

<400> SEQUENCE: 26
aaaagctgga gctccaccgc ggtggcggcc gctctagaac tagtggatcc taaaaaataa     60
gagtggaaaa aaagt                                                      75

<210> SEQ ID NO 27
<211> LENGTH: 75
<212> TYPE: DNA
<213> ORGANISM: artificial sequence
<220> FEATURE:
<223> OTHER INFORMATION: oligonucleotide

<400> SEQUENCE: 27
aaaagctgga gctccaccgc ggtggcggcc gctctagaac tagtggatcc taaagaaaag     60
```
gcaagaagat tttga                                                         75

<210> SEQ ID NO 28
<211> LENGTH: 75
<212> TYPE: DNA
<213> ORGANISM: artificial sequence
<220> FEATURE:
<223> OTHER INFORMATION: oligonucleotide

<400> SEQUENCE: 28
aaaagctgga gctccaccgc ggtggcggcc gctctagaac tagtggatcc aaagtataaa        60
acacttcggt taata                                                         75

<210> SEQ ID NO 29
<211> LENGTH: 75
<212> TYPE: DNA
<213> ORGANISM: artificial sequence
<220> FEATURE:
<223> OTHER INFORMATION: oligonucleotide

<400> SEQUENCE: 29
aaaagctgga gctccaccgc ggtggcggcc gctctagaac tagtggatcc atatagtttt        60
tagaattaac ctgaa                                                         75

<210> SEQ ID NO 30
<211> LENGTH: 75
<212> TYPE: DNA
<213> ORGANISM: artificial sequence
<220> FEATURE:
<223> OTHER INFORMATION: oligonucleotide

<400> SEQUENCE: 30
aaaagctgga gctccaccgc ggtggcggcc gctctagaac tagtggatcc caatgaggag        60
tgattttaca caaaa                                                         75

<210> SEQ ID NO 31
<211> LENGTH: 75
<212> TYPE: DNA
<213> ORGANISM: artificial sequence
<220> FEATURE:
<223> OTHER INFORMATION: oligonucleotide

<400> SEQUENCE: 31
aaaagctgga gctccaccgc ggtggcggcc gctctagaac tagtggatcc tgtgggccga        60
ccaaatagaa gaatt                                                         75

<210> SEQ ID NO 32
<211> LENGTH: 75
<212> TYPE: DNA
<213> ORGANISM: artificial sequence
<220> FEATURE:
<223> OTHER INFORMATION: oligonucleotide

<400> SEQUENCE: 32
aaaagctgga gctccaccgc ggtggcggcc gctctagaac tagtggatcc gggtttaacg        60
gaggagatga aggat                                                         75

<210> SEQ ID NO 33
<211> LENGTH: 75
<212> TYPE: DNA
<213> ORGANISM: artificial sequence
<220> FEATURE:

```
<223> OTHER INFORMATION: oligonucleotide

<400> SEQUENCE: 33
aaaagctgga gctccaccgc ggtggcggcc gctctagaac tagtggatcc atagtttgta      60
cacatagtgt cccta                                                      75

<210> SEQ ID NO 34
<211> LENGTH: 75
<212> TYPE: DNA
<213> ORGANISM: artificial sequence
<220> FEATURE:
<223> OTHER INFORMATION: oligonucleotide

<400> SEQUENCE: 34
aaaagctgga gctccaccgc ggtggcggcc gctctagaac tagtggatcc tgagcagact      60
ggaaaagatg taatg                                                      75

<210> SEQ ID NO 35
<211> LENGTH: 75
<212> TYPE: DNA
<213> ORGANISM: artificial sequence
<220> FEATURE:
<223> OTHER INFORMATION: oligonucleotide

<400> SEQUENCE: 35
cccccctcga ggtcgacggt atcgataagc ttgatatcga attcctgcag cgctgtcact      60
gaactaaaac aataa                                                      75

<210> SEQ ID NO 36
<211> LENGTH: 75
<212> TYPE: DNA
<213> ORGANISM: artificial sequence
<220> FEATURE:
<223> OTHER INFORMATION: oligonucleotide

<400> SEQUENCE: 36
cccccctcga ggtcgacggt atcgataagc ttgatatcga attcctgcag ctttgataaa      60
ttaatacggt aagat                                                      75

<210> SEQ ID NO 37
<211> LENGTH: 75
<212> TYPE: DNA
<213> ORGANISM: artificial sequence
<220> FEATURE:
<223> OTHER INFORMATION: oligonucleotide

<400> SEQUENCE: 37
cccccctcga ggtcgacggt atcgataagc ttgatatcga attcctgcag gaaaaattgc      60
aaaattttga tagag                                                      75

<210> SEQ ID NO 38
<211> LENGTH: 75
<212> TYPE: DNA
<213> ORGANISM: artificial sequence
<220> FEATURE:
<223> OTHER INFORMATION: oligonucleotide

<400> SEQUENCE: 38
cccccctcga ggtcgacggt atcgataagc ttgatatcga attcctgcag gtagacatga      60
tgtactatac aacca                                                      75
```

<210> SEQ ID NO 39
<211> LENGTH: 75
<212> TYPE: DNA
<213> ORGANISM: artificial sequence
<220> FEATURE:
<223> OTHER INFORMATION: oligonucleotide

<400> SEQUENCE: 39
cccccctcga ggtcgacggt atcgataagc ttgatatcga attcctgcag ttcttttctt   60
agaagaggtt ttgtt                                                    75

<210> SEQ ID NO 40
<211> LENGTH: 75
<212> TYPE: DNA
<213> ORGANISM: artificial sequence
<220> FEATURE:
<223> OTHER INFORMATION: oligonucleotide

<400> SEQUENCE: 40
cccccctcga ggtcgacggt atcgataagc ttgatatcga attcctgcag taatcttcgc   60
tacttcaagt ttcat                                                    75

<210> SEQ ID NO 41
<211> LENGTH: 75
<212> TYPE: DNA
<213> ORGANISM: artificial sequence
<220> FEATURE:
<223> OTHER INFORMATION: oligonucleotide

<400> SEQUENCE: 41
cccccctcga ggtcgacggt atcgataagc ttgatatcga attcctgcag cgctcatcca   60
aaaaatcgat aacta                                                    75

<210> SEQ ID NO 42
<211> LENGTH: 75
<212> TYPE: DNA
<213> ORGANISM: artificial sequence
<220> FEATURE:
<223> OTHER INFORMATION: oligonucleotide

<400> SEQUENCE: 42
cccccctcga ggtcgacggt atcgataagc ttgatatcga attcctgcag caacaaaaga   60
atgaaagaaa aaaga                                                    75

<210> SEQ ID NO 43
<211> LENGTH: 75
<212> TYPE: DNA
<213> ORGANISM: artificial sequence
<220> FEATURE:
<223> OTHER INFORMATION: oligonucleotide

<400> SEQUENCE: 43
cccccctcga ggtcgacggt atcgataagc ttgatatcga attcctgcag gaaagtcggc   60
ggcaaaaata aatgt                                                    75

<210> SEQ ID NO 44
<211> LENGTH: 75
<212> TYPE: DNA
<213> ORGANISM: artificial sequence
<220> FEATURE:
<223> OTHER INFORMATION: oligonucleotide

<400> SEQUENCE: 44

```
cccccctcga ggtcgacggt atcgataagc ttgatatcga attcctgcag ttagctgctc    60
tatttatatt tgaag                                                     75
```

<210> SEQ ID NO 45
<211> LENGTH: 75
<212> TYPE: DNA
<213> ORGANISM: artificial sequence
<220> FEATURE:
<223> OTHER INFORMATION: oligonucleotide

<400> SEQUENCE: 45

```
cccccctcga ggtcgacggt atcgataagc ttgatatcga attcctgcag tacatgaact    60
gaccgaaatt gcagc                                                     75
```

<210> SEQ ID NO 46
<211> LENGTH: 75
<212> TYPE: DNA
<213> ORGANISM: artificial sequence
<220> FEATURE:
<223> OTHER INFORMATION: oligonucleotide

<400> SEQUENCE: 46

```
cccccctcga ggtcgacggt atcgataagc ttgatatcga attcctgcag gcttcccttc    60
atccccagtt tttac                                                     75
```

<210> SEQ ID NO 47
<211> LENGTH: 75
<212> TYPE: DNA
<213> ORGANISM: artificial sequence
<220> FEATURE:
<223> OTHER INFORMATION: oligonucleotide

<400> SEQUENCE: 47

```
aaaagctgga gctccaccgc ggtggcggcc gctctagaac tagtggatcc cattgaatca    60
taataaatat gtaaa                                                     75
```

<210> SEQ ID NO 48
<211> LENGTH: 75
<212> TYPE: DNA
<213> ORGANISM: artificial sequence
<220> FEATURE:
<223> OTHER INFORMATION: oligonucleotide

<400> SEQUENCE: 48

```
aaaagctgga gctccaccgc ggtggcggcc gctctagaac tagtggatcc actaaaggcg    60
gcccatattc tgaga                                                     75
```

<210> SEQ ID NO 49
<211> LENGTH: 75
<212> TYPE: DNA
<213> ORGANISM: artificial sequence
<220> FEATURE:
<223> OTHER INFORMATION: oligonucleotide

<400> SEQUENCE: 49

```
aaaagctgga gctccaccgc ggtggcggcc gctctagaac tagtggatcc acatcttatt    60
tttatctact gaaga                                                     75
```

<210> SEQ ID NO 50
<211> LENGTH: 75
<212> TYPE: DNA
<213> ORGANISM: artificial sequence

```
<220> FEATURE:
<223> OTHER INFORMATION: oligonucleotide

<400> SEQUENCE: 50
aaaagctgga gctccaccgc ggtggcggcc gctctagaac tagtggatcc aacaagatgt    60
gctaacattt tccat                                                    75

<210> SEQ ID NO 51
<211> LENGTH: 75
<212> TYPE: DNA
<213> ORGANISM: artificial sequence
<220> FEATURE:
<223> OTHER INFORMATION: oligonucleotide

<400> SEQUENCE: 51
aaaagctgga gctccaccgc ggtggcggcc gctctagaac tagtggatcc ttagggaccg    60
ccagggacca tgatt                                                    75

<210> SEQ ID NO 52
<211> LENGTH: 75
<212> TYPE: DNA
<213> ORGANISM: artificial sequence
<220> FEATURE:
<223> OTHER INFORMATION: oligonucleotide

<400> SEQUENCE: 52
aaaagctgga gctccaccgc ggtggcggcc gctctagaac tagtggatcc agttttcgt    60 tctgaaagag atgca                                                    75

<210> SEQ ID NO 53
<211> LENGTH: 75
<212> TYPE: DNA
<213> ORGANISM: artificial sequence
<220> FEATURE:
<223> OTHER INFORMATION: oligonucleotide

<400> SEQUENCE: 53
aaaagctgga gctccaccgc ggtggcggcc gctctagaac tagtggatcc tctctatact    60
tttctttact attat                                                    75

<210> SEQ ID NO 54
<211> LENGTH: 75
<212> TYPE: DNA
<213> ORGANISM: artificial sequence
<220> FEATURE:
<223> OTHER INFORMATION: oligonucleotide

<400> SEQUENCE: 54
aaaagctgga gctccaccgc ggtggcggcc gctctagaac tagtggatcc taacgcgggg    60
atcagcggtt cgatc                                                    75

<210> SEQ ID NO 55
<211> LENGTH: 75
<212> TYPE: DNA
<213> ORGANISM: artificial sequence
<220> FEATURE:
<223> OTHER INFORMATION: oligonucleotide

<400> SEQUENCE: 55
aaaagctgga gctccaccgc ggtggcggcc gctctagaac tagtggatcc cttgaaaaaa    60
aaccaggaat acggt                                                    75
```

```
<210> SEQ ID NO 56
<211> LENGTH: 75
<212> TYPE: DNA
<213> ORGANISM: artificial sequence
<220> FEATURE:
<223> OTHER INFORMATION: oligonucleotide

<400> SEQUENCE: 56
aaaagctgga gctccaccgc ggtggcggcc gctctagaac tagtggatcc attcagttta    60
gttaaatctg ggtta                                                    75

<210> SEQ ID NO 57
<211> LENGTH: 75
<212> TYPE: DNA
<213> ORGANISM: artificial sequence
<220> FEATURE:
<223> OTHER INFORMATION: oligonucleotide

<400> SEQUENCE: 57
aaaagctgga gctccaccgc ggtggcggcc gctctagaac tagtggatcc atgatgcatg    60
tgagaactga tcacc                                                    75

<210> SEQ ID NO 58
<211> LENGTH: 75
<212> TYPE: DNA
<213> ORGANISM: artificial sequence
<220> FEATURE:
<223> OTHER INFORMATION: oligonucleotide

<400> SEQUENCE: 58
aaaagctgga gctccaccgc ggtggcggcc gctctagaac tagtggatcc tgaatttccg    60
atttccaaag ggaag                                                    75

<210> SEQ ID NO 59
<211> LENGTH: 75
<212> TYPE: DNA
<213> ORGANISM: artificial sequence
<220> FEATURE:
<223> OTHER INFORMATION: oligonucleotide

<400> SEQUENCE: 59
cccccctcga ggtcgacggt atcgataagc ttgatatcga attcctgcag agaaattata    60
tataaatata cttct                                                    75

<210> SEQ ID NO 60
<211> LENGTH: 75
<212> TYPE: DNA
<213> ORGANISM: artificial sequence
<220> FEATURE:
<223> OTHER INFORMATION: oligonucleotide

<400> SEQUENCE: 60
cccccctcga ggtcgacggt atcgataagc ttgatatcga attcctgcag cgtgtacttg    60
ctggccagct agaaa                                                    75

<210> SEQ ID NO 61
<211> LENGTH: 75
<212> TYPE: DNA
<213> ORGANISM: artificial sequence
<220> FEATURE:
<223> OTHER INFORMATION: oligonucleotide

<400> SEQUENCE: 61
```

```
cccccctcga ggtcgacggt atcgataagc ttgatatcga attcctgcag gcatctttcg    60
ataccttagc actcg                                                     75

<210> SEQ ID NO 62
<211> LENGTH: 75
<212> TYPE: DNA
<213> ORGANISM: artificial sequence
<220> FEATURE:
<223> OTHER INFORMATION: oligonucleotide

<400> SEQUENCE: 62
cccccctcga ggtcgacggt atcgataagc ttgatatcga attcctgcag cgattgttcg    60
ccggtgttat aactt                                                     75

<210> SEQ ID NO 63
<211> LENGTH: 75
<212> TYPE: DNA
<213> ORGANISM: artificial sequence
<220> FEATURE:
<223> OTHER INFORMATION: oligonucleotide

<400> SEQUENCE: 63
cccccctcga ggtcgacggt atcgataagc ttgatatcga attcctgcag ctaatccact    60
gccggcagaa tttcc                                                     75

<210> SEQ ID NO 64
<211> LENGTH: 75
<212> TYPE: DNA
<213> ORGANISM: artificial sequence
<220> FEATURE:
<223> OTHER INFORMATION: oligonucleotide

<400> SEQUENCE: 64
cccccctcga ggtcgacggt atcgataagc ttgatatcga attcctgcag cgtttgctga    60
agaactgcaa aatga                                                     75

<210> SEQ ID NO 65
<211> LENGTH: 75
<212> TYPE: DNA
<213> ORGANISM: artificial sequence
<220> FEATURE:
<223> OTHER INFORMATION: oligonucleotide

<400> SEQUENCE: 65
cccccctcga ggtcgacggt atcgataagc ttgatatcga attcctgcag gttaaagaac    60
tcttcaatat tcgtc                                                     75

<210> SEQ ID NO 66
<211> LENGTH: 75
<212> TYPE: DNA
<213> ORGANISM: artificial sequence
<220> FEATURE:
<223> OTHER INFORMATION: oligonucleotide

<400> SEQUENCE: 66
cccccctcga ggtcgacggt atcgataagc ttgatatcga attcctgcag taaggtaagg    60
catcattagc aggat                                                     75

<210> SEQ ID NO 67
<211> LENGTH: 75
<212> TYPE: DNA
```

<213> ORGANISM: artificial sequence
<220> FEATURE:
<223> OTHER INFORMATION: oligonucleotide

<400> SEQUENCE: 67
cccccctcga ggtcgacggt atcgataagc ttgatatcga attcctgcag aggtctatta      60
ccgatgggca aaaga      75

<210> SEQ ID NO 68
<211> LENGTH: 75
<212> TYPE: DNA
<213> ORGANISM: artificial sequence
<220> FEATURE:
<223> OTHER INFORMATION: oligonucleotide

<400> SEQUENCE: 68
cccccctcga ggtcgacggt atcgataagc ttgatatcga attcctgcag actgctgata      60
gtgtcaagaa catgt      75

<210> SEQ ID NO 69
<211> LENGTH: 75
<212> TYPE: DNA
<213> ORGANISM: artificial sequence
<220> FEATURE:
<223> OTHER INFORMATION: oligonucleotide

<400> SEQUENCE: 69
cccccctcga ggtcgacggt atcgataagc ttgatatcga attcctgcag tatagcaacc      60
tcgttgacat tgtga      75

<210> SEQ ID NO 70
<211> LENGTH: 75
<212> TYPE: DNA
<213> ORGANISM: artificial sequence
<220> FEATURE:
<223> OTHER INFORMATION: oligonucleotide

<400> SEQUENCE: 70
cccccctcga ggtcgacggt atcgataagc ttgatatcga attcctgcag gccgtacgtg      60
tcgtctgatc tccaa      75

<210> SEQ ID NO 71
<211> LENGTH: 75
<212> TYPE: DNA
<213> ORGANISM: artificial sequence
<220> FEATURE:
<223> OTHER INFORMATION: oligonucleotide

<400> SEQUENCE: 71
aaaagctgga gctccaccgc ggtggcggcc gctctagaac tagtggatcc aagtcattcc      60
attccattct atatc      75

<210> SEQ ID NO 72
<211> LENGTH: 75
<212> TYPE: DNA
<213> ORGANISM: artificial sequence
<220> FEATURE:
<223> OTHER INFORMATION: oligonucleotide

<400> SEQUENCE: 72
aaaagctgga gctccaccgc ggtggcggcc gctctagaac tagtggatcc gttacataag      60
gatcaacctt ttttt      75

```
<210> SEQ ID NO 73
<211> LENGTH: 75
<212> TYPE: DNA
<213> ORGANISM: artificial sequence
<220> FEATURE:
<223> OTHER INFORMATION: oligonucleotide

<400> SEQUENCE: 73
aaaagctgga gctccaccgc ggtggcggcc gctctagaac tagtggatcc tttacggtga    60
aatagcttct ctctt                                                    75

<210> SEQ ID NO 74
<211> LENGTH: 75
<212> TYPE: DNA
<213> ORGANISM: artificial sequence
<220> FEATURE:
<223> OTHER INFORMATION: oligonucleotide

<400> SEQUENCE: 74
aaaagctgga gctccaccgc ggtggcggcc gctctagaac tagtggatcc ggattgattt    60
cactaaaaat caaga                                                    75

<210> SEQ ID NO 75
<211> LENGTH: 75
<212> TYPE: DNA
<213> ORGANISM: artificial sequence
<220> FEATURE:
<223> OTHER INFORMATION: oligonucleotide

<400> SEQUENCE: 75
aaaagctgga gctccaccgc ggtggcggcc gctctagaac tagtggatcc atgctgtttt    60
ttgcttggct tctta                                                    75

<210> SEQ ID NO 76
<211> LENGTH: 75
<212> TYPE: DNA
<213> ORGANISM: artificial sequence
<220> FEATURE:
<223> OTHER INFORMATION: oligonucleotide

<400> SEQUENCE: 76
aaaagctgga gctccaccgc ggtggcggcc gctctagaac tagtggatcc catggctggt    60 ttttttctt ttttt                                                     75

<210> SEQ ID NO 77
<211> LENGTH: 75
<212> TYPE: DNA
<213> ORGANISM: artificial sequence
<220> FEATURE:
<223> OTHER INFORMATION: oligonucleotide

<400> SEQUENCE: 77
aaaagctgga gctccaccgc ggtggcggcc gctctagaac tagtggatcc aaaaatatta    60
attattgcgt cctat                                                    75

<210> SEQ ID NO 78
<211> LENGTH: 75
<212> TYPE: DNA
<213> ORGANISM: artificial sequence
<220> FEATURE:
<223> OTHER INFORMATION: oligonucleotide
```

```
<400> SEQUENCE: 78
aaaagctgga gctccaccgc ggtggcggcc gctctagaac tagtggatcc cgttaatata    60
aacttatgta tattc                                                     75

<210> SEQ ID NO 79
<211> LENGTH: 75
<212> TYPE: DNA
<213> ORGANISM: artificial sequence
<220> FEATURE:
<223> OTHER INFORMATION: oligonucleotide

<400> SEQUENCE: 79
aaaagctgga gctccaccgc ggtggcggcc gctctagaac tagtggatcc aattgaaact    60
acgtacctga aagaa                                                     75

<210> SEQ ID NO 80
<211> LENGTH: 75
<212> TYPE: DNA
<213> ORGANISM: artificial sequence
<220> FEATURE:
<223> OTHER INFORMATION: oligonucleotide

<400> SEQUENCE: 80
aaaagctgga gctccaccgc ggtggcggcc gctctagaac tagtggatcc gggaaaagcc    60
gagaattccc gatga                                                     75

<210> SEQ ID NO 81
<211> LENGTH: 75
<212> TYPE: DNA
<213> ORGANISM: artificial sequence
<220> FEATURE:
<223> OTHER INFORMATION: oligonucleotide

<400> SEQUENCE: 81
aaaagctgga gctccaccgc ggtggcggcc gctctagaac tagtggatcc aaaaaatgac    60
acaaatcatc tctgt                                                     75

<210> SEQ ID NO 82
<211> LENGTH: 75
<212> TYPE: DNA
<213> ORGANISM: artificial sequence
<220> FEATURE:
<223> OTHER INFORMATION: oligonucleotide

<400> SEQUENCE: 82
aaaagctgga gctccaccgc ggtggcggcc gctctagaac tagtggatcc ataatctaat    60
agctgagtgg aagaa                                                     75

<210> SEQ ID NO 83
<211> LENGTH: 75
<212> TYPE: DNA
<213> ORGANISM: artificial sequence
<220> FEATURE:
<223> OTHER INFORMATION: oligonucleotide

<400> SEQUENCE: 83
cccccctcga ggtcgacggt atcgataagc ttgatatcga attcctgcag ttctttgtca    60
attgcatctc tagtt                                                     75

<210> SEQ ID NO 84
<211> LENGTH: 75
```

```
<212> TYPE: DNA
<213> ORGANISM: artificial sequence
<220> FEATURE:
<223> OTHER INFORMATION: oligonucleotide

<400> SEQUENCE: 84
cccccctcga ggtcgacggt atcgataagc ttgatatcga attcctgcag agttcgatag     60
agcatctttc aatac                                                      75

<210> SEQ ID NO 85
<211> LENGTH: 75
<212> TYPE: DNA
<213> ORGANISM: artificial sequence
<220> FEATURE:
<223> OTHER INFORMATION: oligonucleotide

<400> SEQUENCE: 85
cccccctcga ggtcgacggt atcgataagc ttgatatcga attcctgcag tggacttgaa     60
cataggtgat tcttg                                                      75

<210> SEQ ID NO 86
<211> LENGTH: 75
<212> TYPE: DNA
<213> ORGANISM: artificial sequence
<220> FEATURE:
<223> OTHER INFORMATION: oligonucleotide

<400> SEQUENCE: 86
cccccctcga ggtcgacggt atcgataagc ttgatatcga attcctgcag gatgtacttc     60
ccgccataca aatat                                                      75

<210> SEQ ID NO 87
<211> LENGTH: 75
<212> TYPE: DNA
<213> ORGANISM: artificial sequence
<220> FEATURE:
<223> OTHER INFORMATION: oligonucleotide

<400> SEQUENCE: 87
cccccctcga ggtcgacggt atcgataagc ttgatatcga attcctgcag aaagatgcaa     60
gcaataatga aaatc                                                      75

<210> SEQ ID NO 88
<211> LENGTH: 75
<212> TYPE: DNA
<213> ORGANISM: artificial sequence
<220> FEATURE:
<223> OTHER INFORMATION: oligonucleotide

<400> SEQUENCE: 88
cccccctcga ggtcgacggt atcgataagc ttgatatcga attcctgcag tttctattgt     60
ttcactattc tttat                                                      75

<210> SEQ ID NO 89
<211> LENGTH: 75
<212> TYPE: DNA
<213> ORGANISM: artificial sequence
<220> FEATURE:
<223> OTHER INFORMATION: oligonucleotide

<400> SEQUENCE: 89
cccccctcga ggtcgacggt atcgataagc ttgatatcga attcctgcag attctcaccc     60
```
tgtctgcttt tattc                                                          75

<210> SEQ ID NO 90
<211> LENGTH: 75
<212> TYPE: DNA
<213> ORGANISM: artificial sequence
<220> FEATURE:
<223> OTHER INFORMATION: oligonucleotide

<400> SEQUENCE: 90 ccccccctcga ggtcgacggt atcgataagc ttgatatcga attcctgcag ttcctcatct        60
tgaatcaaat gctta                                                          75

<210> SEQ ID NO 91
<211> LENGTH: 75
<212> TYPE: DNA
<213> ORGANISM: artificial sequence
<220> FEATURE:
<223> OTHER INFORMATION: oligonucleotide

<400> SEQUENCE: 91 ccccccctcga ggtcgacggt atcgataagc ttgatatcga attcctgcag gagttcagaa        60
ccgtgacctt tattc                                                          75

<210> SEQ ID NO 92
<211> LENGTH: 75
<212> TYPE: DNA
<213> ORGANISM: artificial sequence
<220> FEATURE:
<223> OTHER INFORMATION: oligonucleotide

<400> SEQUENCE: 92 ccccccctcga ggtcgacggt atcgataagc ttgatatcga attcctgcag gttcgagtcc        60
tgcagttgtc gttat                                                          75

<210> SEQ ID NO 93
<211> LENGTH: 75
<212> TYPE: DNA
<213> ORGANISM: artificial sequence
<220> FEATURE:
<223> OTHER INFORMATION: oligonucleotide

<400> SEQUENCE: 93 ccccccctcga ggtcgacggt atcgataagc ttgatatcga attcctgcag agttctgtcc        60
atccggtggg cgacc                                                          75

<210> SEQ ID NO 94
<211> LENGTH: 75
<212> TYPE: DNA
<213> ORGANISM: artificial sequence
<220> FEATURE:
<223> OTHER INFORMATION: oligonucleotide

<400> SEQUENCE: 94 ccccccctcga ggtcgacggt atcgataagc ttgatatcga attcctgcag tgcacgatag        60
aaatcgacaa ggcga                                                          75

<210> SEQ ID NO 95
<211> LENGTH: 75
<212> TYPE: DNA
<213> ORGANISM: artificial sequence
<220> FEATURE:
<223> OTHER INFORMATION: oligonucleotide

```
<400> SEQUENCE: 95
aaaagctgga gctccaccgc ggtggcggcc gctctagaac tagtggatcc cacgaacaaa     60
ggtttattgc gcttg                                                     75

<210> SEQ ID NO 96
<211> LENGTH: 75
<212> TYPE: DNA
<213> ORGANISM: artificial sequence
<220> FEATURE:
<223> OTHER INFORMATION: oligonucleotide

<400> SEQUENCE: 96
aaaagctgga gctccaccgc ggtggcggcc gctctagaac tagtggatcc tagataatat     60
aaaagtgaca tctaa                                                     75

<210> SEQ ID NO 97
<211> LENGTH: 75
<212> TYPE: DNA
<213> ORGANISM: artificial sequence
<220> FEATURE:
<223> OTHER INFORMATION: oligonucleotide

<400> SEQUENCE: 97
aaaagctgga gctccaccgc ggtggcggcc gctctagaac tagtggatcc gcctaaagca     60
catttcataa ataaa                                                     75

<210> SEQ ID NO 98
<211> LENGTH: 75
<212> TYPE: DNA
<213> ORGANISM: artificial sequence
<220> FEATURE:
<223> OTHER INFORMATION: oligonucleotide

<400> SEQUENCE: 98
aaaagctgga gctccaccgc ggtggcggcc gctctagaac tagtggatcc taatttaacg     60
tatagttatg taaag                                                     75

<210> SEQ ID NO 99
<211> LENGTH: 75
<212> TYPE: DNA
<213> ORGANISM: artificial sequence
<220> FEATURE:
<223> OTHER INFORMATION: oligonucleotide

<400> SEQUENCE: 99
aaaagctgga gctccaccgc ggtggcggcc gctctagaac tagtggatcc ttcttgataa     60
aaaaatagct atgtg                                                     75

<210> SEQ ID NO 100
<211> LENGTH: 75
<212> TYPE: DNA
<213> ORGANISM: artificial sequence
<220> FEATURE:
<223> OTHER INFORMATION: oligonucleotide

<400> SEQUENCE: 100
aaaagctgga gctccaccgc ggtggcggcc gctctagaac tagtggatcc acttgttctt     60
atatctctgt atgta                                                     75

<210> SEQ ID NO 101
```

```
<211> LENGTH: 75
<212> TYPE: DNA
<213> ORGANISM: artificial sequence
<220> FEATURE:
<223> OTHER INFORMATION: oligonucleotide

<400> SEQUENCE: 101
aaaagctgga gctccaccgc ggtggcggcc gctctagaac tagtggatcc tgtaacggaa      60
cactcaaaag tgact                                                      75

<210> SEQ ID NO 102
<211> LENGTH: 75
<212> TYPE: DNA
<213> ORGANISM: artificial sequence
<220> FEATURE:
<223> OTHER INFORMATION: oligonucleotide

<400> SEQUENCE: 102
aaaagctgga gctccaccgc ggtggcggcc gctctagaac tagtggatcc ggtaaacgaa      60
gagaattact tcggc                                                      75

<210> SEQ ID NO 103
<211> LENGTH: 75
<212> TYPE: DNA
<213> ORGANISM: artificial sequence
<220> FEATURE:
<223> OTHER INFORMATION: oligonucleotide

<400> SEQUENCE: 103
aaaagctgga gctccaccgc ggtggcggcc gctctagaac tagtggatcc acaaatcttg      60
tcctaaatac tccca                                                      75

<210> SEQ ID NO 104
<211> LENGTH: 75
<212> TYPE: DNA
<213> ORGANISM: artificial sequence
<220> FEATURE:
<223> OTHER INFORMATION: oligonucleotide

<400> SEQUENCE: 104
aaaagctgga gctccaccgc ggtggcggcc gctctagaac tagtggatcc actggtatgt      60
cttttatcta acagt                                                      75

<210> SEQ ID NO 105
<211> LENGTH: 75
<212> TYPE: DNA
<213> ORGANISM: artificial sequence
<220> FEATURE:
<223> OTHER INFORMATION: oligonucleotide

<400> SEQUENCE: 105
aaaagctgga gctccaccgc ggtggcggcc gctctagaac tagtggatcc acctagcttt      60
attctgagcg tcgcc                                                      75

<210> SEQ ID NO 106
<211> LENGTH: 75
<212> TYPE: DNA
<213> ORGANISM: artificial sequence
<220> FEATURE:
<223> OTHER INFORMATION: oligonucleotide

<400> SEQUENCE: 106
aaaagctgga gctccaccgc ggtggcggcc gctctagaac tagtggatcc aacgatgcca      60
```

```
gatgcagttc aaaaa                                                    75

<210> SEQ ID NO 107
<211> LENGTH: 9
<212> TYPE: DNA
<213> ORGANISM: artificial sequence
<220> FEATURE:
<223> OTHER INFORMATION: SPET promoter site

<400> SEQUENCE: 107 agccgccga                                                            9

<210> SEQ ID NO 108
<211> LENGTH: 39
<212> TYPE: DNA
<213> ORGANISM: artificial sequence
<220> FEATURE:
<223> OTHER INFORMATION: Triple promoter sequence

<400> SEQUENCE: 108
agccgccgac ttcctagccg ccgattcttc agccgccga                          39
```

COMPOSITIONS AND METHODS FOR CONTROLLING MICROBIAL GROWTH

CROSS-REFERENCE TO RELATED APPLICATIONS

This application is a continuation of U.S. patent application Ser. No. 15/000,640, filed Jan. 19, 2016, which claims priority to U.S. Provisional application No. 62/105,112, filed Jan. 19, 2015, the disclosure of which is incorporated herein by reference.

STATEMENT REGARDING FEDERALLY SPONSORED RESEARCH

This invention was made with government support under contract no. N66001-12-C4020 awarded by the Defense Advanced Research Project Agency (DARPA). The government has certain rights in the invention.

SEQUENCE LISTING

The instant application contains a Sequence Listing which has been submitted in an ASCII text file and is hereby incorporated by reference in its entirety. Said .txt file is named "CON_BOE_US_NPA_ST25.txt", was created on Aug. 27, 2019, and is 28,025 bytes in size.

FIELD

The present disclosure is generally related to biocontainment and more specifically to orthogonal genetic modifications of microorganisms that impose a requirement for exogenously provided compounds to maintain viability of the microorganism, yet do not adversely affect their fitness.

BACKGROUND

The rapid development of biotechnology depends heavily on engineered microbes. In particular, the booming field of synthetic biology demonstrates the feasibility of de novo synthesis of viral genomes, bacterial genomes and eukaryotic chromosomes. The technologies underpinning synthetic biology are advanced DNA synthesis and assembly, genome editing and computational assisted designs, which are all becoming commoditized and thus increasingly available to the public. The advance of synthetic biology promises to ultimately improve human living conditions through a better understanding of fundamental sciences as well as a multitude of practical applications. However biosafety mechanisms should be carefully considered to minimize or prevent dual use. Professionals have chemically synthesized infectious virus in the absence of natural templates (Cello J, Paul A V, & Wimmer E (2002) Science 297(5583):1016-1018) and reconstitute infectious human retroviruses (Lee Y N & Bieniasz P D (2007) PLoS pathogens 3(1):e10.) and the 1918 'Spanish' influenza virus (Tumpey T M, et al. (2005) Science 310(5745):77-80). At the same time, relative amateurs are trying to engineer microbes in a Do-It-Yourself fashion (world wide web address:diybio.org). Proactive measures are warranted to minimize both bioterror (e.g. the anthrax attack the United States in 2000) and "bioerror" such as accidental environment releases or self-infection by lab-adapted microbes as in the case of a lab infection of an individual with hemochromatosis, where the victim scientist's high iron levels caused by hemochromatosis complemented the natural iron requirement of attenuated *Y. pestis* (Frank KM, et. (2011) The New England journal of medicine 364(26):2563-2564). Intrinsic biocontainment can also be used to prevent industrial espionage.

Work on biocontainment has largely focused on auxotrophic mutations or inducible lethality based on toxin-antitoxin pairs in bacteria (Bej A K, et al (1988) Applied and environmental microbiology 54(10):2472-2477; Gerdes K, et al. (1986) The EMBO journal 5(8):2023-2029; Knudsen S M & Karlstrom O H (1991) Applied and environmental microbiology 57(1):85-92; Poulsen L K, et al. Molecular microbiology 3(11):1463-1472). There is also recent work to reduce unintended plasmid propagation in bacterial (Wright O, et al., (2014) GeneGuard: A Modular Plasmid System Designed for Biosafety. ACS synthetic biology). Existing biocontainment technologies usually depend on a single cellular mechanism. Such "uniplex" approaches lack redundancy, and the leakiness of toxin genes often compromises fitness and normal behavior of the engineered microbes, reducing the likelihood that they will be accepted by researchers or industrial biotechnologists. Also, ongoing selection for the toxin gene is required. Reduced fitness has at least three undesirable features: 1) it reduces their usefulness as models for the behavior of the natural organism 2) it may reduce their "performance" in industrial applications and 3) it may increase the frequency of escape mutants (revertants able to grow in the absence of the compound). Finally, auxotrophic strains rely on supplementation of corresponding nutrients at micromolar concentrations, rendering them too costly for industrial scale-up. Thus there is an ongoing need for improved compositions and methods designed for biocontainment of microorganisms. The present disclosure meets these and other needs.

SUMMARY OF THE DISCLOSURE

In general the present disclosure relates to modified microorganisms. The microorganisms are modified such that their growth can be controlled using exogenously provided compounds. In a particular implementation the disclosure provides a modified microorganism, the growth of which can be controlled by exogenously provided first and second compounds which modulate one or more genetic alterations in the modified microorganisms. The genetic alterations in certain approaches comprise i) a promoter inducible by the first exogenously supplied compound, wherein the inducible promoter is operably linked to an RNA coding sequence. In certain approaches, expression of the RNA coding sequence is essential for growth of the microorganism. The disclosure includes the proviso that the RNA coding sequence does not encode an auxotrophic marker. The microorganisms may also be modified to comprise ii) a pair of site specific recombinase recognition sites (SSRRS) flanking or within the RNA coding sequence. The SSRS can be configured such that recombination between the SSRRS disrupts expression of the RNA coding sequence. The microorganisms may also be modified to comprise iii) a site specific recombinase (SSR) coding region, wherein the SSR is specific for the SSRS. In certain embodiments expression of the SSR is repressed by the second exogenously supplied compound.

In certain implementations, a promoter that is operably linked to an RNA coding sequence is inducible by a sub-micromolar concentration of the first compound. Likewise, in certain approaches, expression of the SSR can be repressible, or its function inhibited, by a sub-micromolar concentration of the second compound. In certain embodiments, a modified microorganism is provided with some or all of the aforementioned modifications, and the modified microorganism has the same or an enhanced growth rate relative to a microorganism of the same type that does not comprise the modifications, i.e., a control.

The modified microorganisms of this disclosure can be provided in, for example, a cell culture. The cell culture can comprise a culture medium, and the culture medium can comprises sub-micromolar concentrations of the first and/or second compounds. The disclosure further provides for the inclusion of decoy compounds in the culture medium. In particular examples the decoy compounds do not substantially affect the gene expression and/or or growth profile(s) of the modified microorganisms. In certain embodiments the decoy compounds can be included in the cell culture medium in greater than sub-micromolar concentrations.

In certain aspects the disclosure includes modified microorganisms that comprise at least one decoy RNA coding sequence, or other decoy genetic element. In general, if the decoy RNA coding sequence is present and expressed, its expression is not affected by the first or the second compound, or by decoy compounds. Likewise, the function or activity of any other decoy genetic element that may be present in the microorganism is not affected by the first or second compound, or by decoy compounds.

In another aspect a kit for use in controlling growth of modified microorganisms of this disclosure is provided. The kit can comprise a plurality of compounds. The plurality of compounds can include the first and/or second compounds, and can further comprise at least one decoy compound. The kit can also comprise a growth medium, or growth medium components, and may also comprise a microorganism or microorganism culture of this disclosure.

In another aspect the disclosure includes a method for controlling growth of a population of modified microorganisms as described herein. This method generally comprises culturing such a population of microorganisms in a culture medium that comprises a sub-micromolar concentration of the first and second compounds, and may further comprise decoy compounds. In this regard, in certain embodiments, the first and second compounds can be added to the culture medium in a composition that comprises at least one decoy compound. The decoy compound(s) can be included in a molar excess relative to the first and second compounds.

In a further aspect, the disclosure comprises a method of making a modified microorganism, the growth of which can be controlled using the aforementioned first and second compounds, such as at sub-micromolar concentration in a culture medium. In general, this approach comprises introducing into the microorganism a promoter inducible by the first compound. As described above, the inducible promoter is operably linked to an RNA coding sequence, transcription of which is essential for growth of the microorganism. The method can further comprise introducing into the microorganism a pair of SSRRS flanking or within the RNA coding sequence such that recombination between the SSRRS disrupts transcription of the RNA coding sequence. The method can further comprise introducing into the microorganism a SSR coding region which is specific for the SSRS. Expression of the SSR may be repressed by the second compound. Subsequent to the introduction of the inducible promoter and/or the SSRS, the method comprises culturing the microorganisms in a culture medium that comprises a sub-micromolar concentration of the first and second compounds. The culture medium may be supplemented with decoy compounds. The disclosure includes progeny of any of the microorganisms disclosed herein, and all polynucleotides disclosed herein.

DESCRIPTION OF THE DRAWINGS

The patent or application file contains at least one drawing executed in color. Copies of this patent or patent application publication with color drawing(s) will be provided by the Office upon request and payment of the necessary fee.

FIG. 23: Analysis of escaper mutations location. For each escaper analyzed strain that was cured from the plasmid, plasmid was transformed to the original SG strain and the cured strain was transformed with the wt plasmid (pGEVnew). Each was plated on SC–Ura+GAL, SC–Ura+ 30 nM Estradiol and SC–Ura. For each escaper, the original SG was also plated as well as the original escaper.

DETAILED DESCRIPTION

Figure 1:
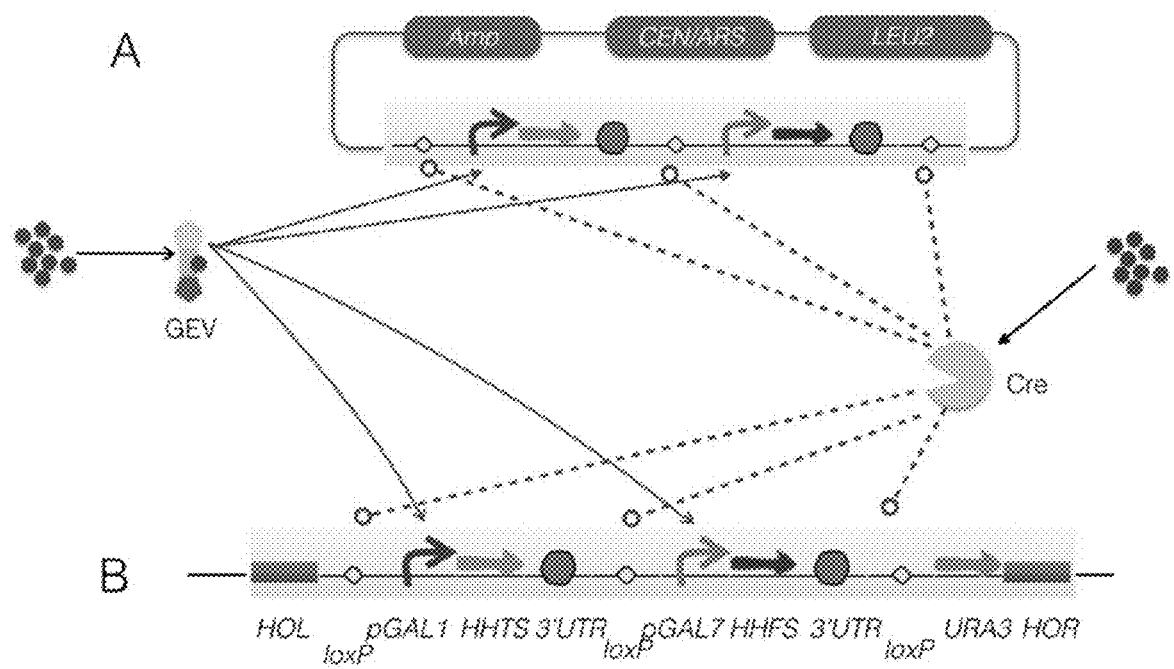
FIG. 1: The structure of triplex histone switch. Duplex integrated safeguard based on a pair of histone genes. Histone H3 gene HHTS is regulated by a galactose promoter pGAL1, and the histone H4 gene HHFS is controlled by another galactose promoter pGAL7. Each histone switch is flanked by a pair of loxP sites. The duplex histone safeguard switches can either be on a CEN/ARS plasmid (A) or integrated into a genomic locus (B). Either the native Gal4 protein or an engineered tribrid protein called GEV turns on the transcription of the histone genes in the presence of their ligands, such that the engineered yeast survives. The third level of redundancy is use of an orthogonal control mechanism, site-specific recombination. Any pair of loxP sites (yellow diamonds) on the construct will recombine and delete one or both histone genes upon Cre, activation, leading to inviability. Both proteins can be independently controlled by small molecule(s). Hooked arrows, promoters; filled arrows, histone genes, blue lozenges, standardized vector components; HOL, HOR; sequences to left and right of HO gene, where the safeguard was integrated.

The present disclosure is generally directed to modified microorganisms, the growth of which can be controlled by exogenously provided chemical compounds that affect the expression and/or integrity of an RNA coding sequence present in a chromosome or other genetic element, non-limiting examples of which include plasmids and Yeast Artificial Chromosomes (YAC) in the microorganism.

The RNA coding sequence encodes an RNA which may or may not encode a protein, but for the purpose of this disclosure it does not encode an auxotrophic marker. Those skilled in the art will appreciate that an auxotrophic marker is a gene encoding a protein that is required for the microorganism to synthesize a compound needed for growth, examples of which include but are not necessarily limited to nucleotides, amino acids, cofactors, vitamins and fatty acids. Further, the skilled artisan will be able to ascertain whether or not any particular DNA sequence encodes an auxotrophic marker based on well-known parameters.

In general the present disclosure takes advantage of the discovery that growth of microorganisms can be tightly controlled using two modes of experimentally generated dependency on exogenously provided compounds, one being transcriptional, and the other the presence/absence of the RNA coding sequence, i.e., recombinational. For ease of description an RNA coding sequence may be referred to herein as a gene, but it should be understood that in various embodiments the RNA coding sequence can encode an mRNA that is translated into a protein, such as an essential protein, or an essential non-coding RNA, such as an essential miRNA, an essential snoRNA, an essential snRNA, or any other RNA that is required for cell survival but does not encode an auxotrophic marker, and wherein the expression of the RNA is controlled by an inducible promoter as will be more fully described below. Thus, an "essential" RNA coding sequence as used herein encodes an RNA, the expression of which is required for the cell to remain living and/or to divide. In this regard, the dual-pronged approach to biocontainment that is an aspect of this disclosure is directed to at least one gene that is essential for growth of the microorganism. However, notwithstanding its essentiality, the disclosure provides for concurrent control of transcription and maintenance of the integrity of the essential gene using exogenously provided compounds without negatively impacting the fitness of the microorganism. Thus, in embodiments, a modified microorganism of this disclosure that is under strict biocontainment via the exogenously provided compounds will nevertheless be, in certain embodiments, indistinguishable from a culture of non-modified microorganisms of the same type based on fitness. In embodiments, fitness is determined by factors such as growth rate, cell size and/or morphology, and transcriptome analysis, wherein the transcription of the gene under the control of the exogenously provided compounds, as well the transcription of other genes, is the same or essentially the same as those of a positive control culture, or other suitable reference.

In certain embodiments the multiplex genome safeguards that are present in a modified microorganism of this disclosure comprise the following:

i) a promoter inducible by a first exogenously provided compound, wherein the inducible promoter is operably linked to an RNA coding sequence, expression of which is essential for growth of the microorganism, wherein the RNA coding sequence does not encode an auxotrophic marker; and ii) a pair of site specific recombinase recognition sites (SSRRS) flanking or within the RNA coding sequence such that recombination between the SSRRS disrupts expression of the RNA coding sequence; and iii) a site specific recombinase (SSR) coding region, wherein the SSR is specific for the SSRS, and wherein expression of the SSR is repressed by a second exogenously provided compound.

It will be recognized that the terms "first" and "second" compound are for ease of reference and do not specify any sequence or magnitude of importance.

As an alternative to ii) and iii), the RNA coding sequence can comprise an endonuclease recognition target site, in which case the microorganism will also encode an endonuclease (as distinct from an SSRS) that can cleave the endonuclease site with specificity, wherein expression of the endonuclease is repressed by the exogenously provided second compound. Non-limiting examples of such endonucleases include clustered regularly interspaced short palindromic repeats (CRISPR)-associated (Cas) enzymes and their associated guide RNAs, as well as zinc finger nucleases and Transcription activator-like effector nucleases (TALENs). Each of these distinct endonucleases are well known in the art, as are their DNA site-recognition requirements and therefore, given the benefit of the present disclosure, the skilled artisan can adapt these alternatives to function in the orthogonal, multiplex safeguard approaches that are encompassed by the instant disclosure. However, as an illustrative proof of principle, this disclosure utilizes the SSR-based approach to show the capability to disrupt the DNA segment that comprises the RNA coding sequence by simply ceasing the provision of the second exogenous compound to the microorganisms. Accordingly, this disclosure uses the capability to eliminate (or otherwise disrupt) the RNA coding region from the cell via a recombinatorial approach, thereby resulting in a lethal event when and if the second compound is withdrawn from the microorganism. Any suitable SSR can be used as one of the prongs of the biocontainment approach of this disclosure, and many SSRs are known in the art, as are their site specific recognition sites. In non-limiting embodiments the SSR comprises a Cre recombinase, and is therefore used with loxP sites. A Cre recombinase is useful because it can recombine DNA sequences without the need for cofactors, but other SRR and related systems can also be used and include but are not limited to Flp Recombinase which functions in the Flp/FRT system, the Dre recombinase which functions in the Dre-rox system, the Vika recombinase which functions in the Vika/vox system, Bxb1 recombinase which functions with attP and attB sites, long terminal repeat (LTR) site-specific recombinase (Tre), and other serine recombinases, such as phiC31 integrase which mediates recombination between two 34 base pair sequences termed attachment sites (att), Hin recombinase, which recognizes 26 bp imperfect inverted repeat sequences or int2-13 each of which each recognizes distinct target sites of 39-66 bp (Yang et al. Nat Methods. 2014; 11(12): 1261-1266.

Expression of the SSR could be under control of a repressor which requires persistence of an exogenously provided compound to sustain the repressed state. In embodiments, repression of SSR expression is achieved by a sub-micromolar concentration of an exogenously provided compound. As is known in the art, a repressor comprises a DNA binding protein that inhibits expression of the gene in question by binding with specificity to a DNA segment, such as an operator or a silencer, or to otherwise block the attachment of an RNA polymerase to DNA. Binding of the repressor protein requires the exogenously provided compound, and thus this arrangement comprises one non-limiting example of the multiplex switches of this disclosure. Examples of repressors include the Tet repressor, the lac repressor and the lambda repressor, the Met repressor and the Trp repressor, all from *E. coli.*

In another embodiment, the small molecule may directly influence the biochemical activity of the SSR protein. In one embodiment, the exogenously provided compound that acts directly on the SSR protein comprises a steroid hormone. In an embodiment the exogenously provided compound is an estradiol, such as β-Estradiol. In embodiment, the compound releases the SSR protein from the binding by Hsp90 protein, allowing it to transit to the cell nucleus, where it can operate on the target. Any compound that blocks either the DNA binding activity of the SSR protein directly, interferes with the cutting and joining activity of the SSR protein, or the transit of the SSR protein to the nucleus will be useful in this embodiment.

With respect to the inducible promoter, any suitable inducible promoter can be introduced into the microorganism such that it is operably linked to the essential RNA coding sequence, provided that the promoter is inducible by an exogenously provided compound at a sub-micromolar concentration. The DNA sequences of wide variety of inducible promoters for use in prokaryotic and eukaryotic microorganism sequences are known in the art, as are the agents that are capable of inducing them, and many cloning systems for introducing inducible promoters into microorganisms are commercially available and can be adapted for use with embodiments of this disclosure. In non-limiting embodiments, the promoters can be GAL1 or GAL7 promoters, the MET23 promoter, the FUS1 promoter, and the ecdysone promoter, such as for use in eukaryotic microorganisms, such as yeast. In an additional embodiment, engineered regulated promoters such as the Tet promoter TRE which is regulated by tetracycline, anhydrotetracycline or doxycline and the lad-regulated promoter ADHi, which is regulated by IPTG (isopropyl-thio-galactoside) may also be used in eukaryotic cells. In embodiments, the native lac, Tet, Ara, promoters and many others may be used in prokaryotic cells. Additional promoters will be known to those skilled in the art, such as eukaryotic promoters described in Maya et al., Biotechnol Lett. 2008 June; 30(6):979-87, Stanton et al. ACS Synth Biol. 2014; 3(12):880-91 and Ikushima et al. G3 (Bethesda). 2015; 5(10):1983-90. and prokaryotic promoters as described in Goldstein et al., Biotechnol Annu Rev. 1995; 1:105-28 and Brautaset et al., Microb Biotechnol. 2009 January; 2(1):15-30 or Stanton et al. Nat Chem Biol. 2014; 10(2):99-105.

Figure 13:
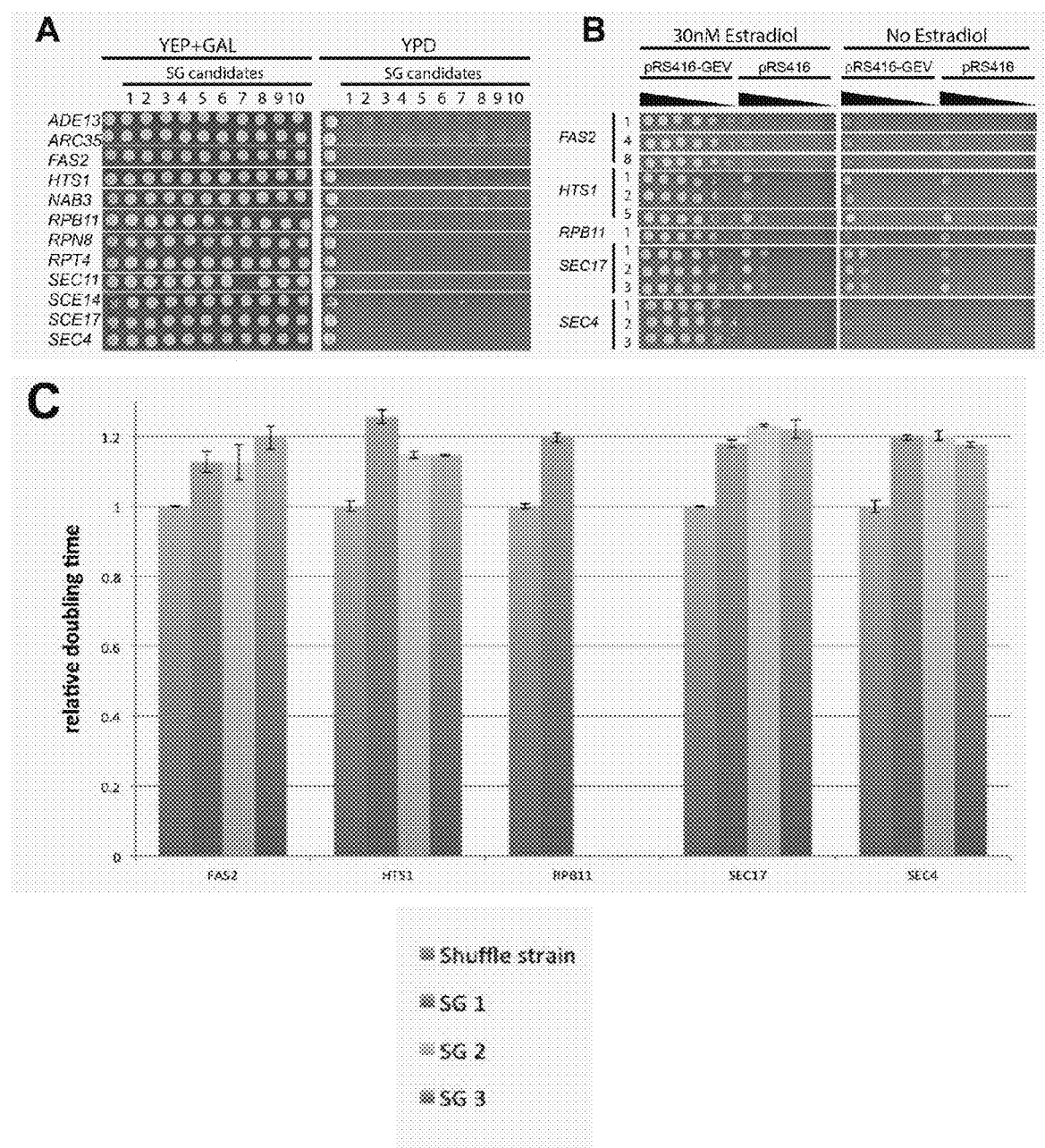
FIG. 13: Screening for best SG strain after integration of the SG construct. Following transformation into the shuffle strains, and plating on 5-Foa, 10 candidates from each essential gene were examined by plating on YEP−GAL vs. YPD. (A) 12 best performing strains, were chosen for GEV plasmid transformation. 8 isolates from each SG strain were transformed with GEV containing plasmid and analyzed using a dot assay on Dextrose without Estradiol. (B) 13 good candidates that grow well on media with estradiol and do not grow on media without estradiol were chosen for further analysis. (C) Liquid cultures were diluted and subjected to OD measurements every 10 min in a 24 hrs period. Growth curve was created and doubling time was calculated for each strain. The experiment included 3 independent cultures for each strain in order to calculate SD.

The RNA coding sequence can comprise any essential RNA/gene. In one embodiment the gene that is the subject of the multiplex controls described herein encodes a histone protein. In embodiments, the modified microorganism is a yeast, and the protein coding gene that is subject to the biocontainment controls is SUI1, HSP10 or RPC11. In another embodiment, the RNA sequence encodes an essential tRNA or the RNA subunit of RNAse P, an essential enzyme. In various embodiments the RNA coding sequence can be resident on a chromosome of the microorganism, or it can be present on an episomal element. Those skilled in the art will comprehend how to recognize and/or identify candidate RNA coding sequences that are suitable for exploiting in the orthogonal safeguard switches of this invention, including but not necessarily limited to high throughput screening methods, and testing of randomly assembled or rationally designed transcription units, which can comprise promoters, genes and 3'UTRs. In one embodiment for use in eukaryotic microorganisms such as yeast, the Yeast Golden Gate approach can be adapted to identify suitable genes for use in biocontainment according to this disclosure. In certain embodiments, any one or any combination of the 47 genes depicted in FIGS. 13 and 18 can be used. A representative and non-limiting listing of these genes, including their respective GenBank accession numbers, are presented in Table 13. The sequences associates with the GenBank accession numbers are incorporated herein by reference as they are presented in the GenBank database as of the filing date of this application or patent.

In another aspect the present disclosure comprises modified microorganisms as described above in culture, wherein the culture medium comprises the first and second exogenously provided compounds. In embodiments the culture medium comprises sub-micromolar amounts of the first and second compounds (the inducer and the repressor compound). In embodiments the culture is a liquid culture, or is a culture provided on a solid or semi-solid growth medium. In embodiments, the culture comprises an agent that is used to inhibit cellular damage by ice crystal formation, such as glycerol. In embodiments the culture is maintained as a frozen stock. In embodiments microorganisms in the culture have an escape rate (meaning viability in the absence of one or both of the first and second compounds) of at least $10^{-5}$, $10^{-6}$, $10^{-7}$, $10^{-8}$, $10^{-9}$, $10^{-10}$, or an even lower escape rate.

It is expected that the present disclosure will be adaptable for use with any microorganism, including prokaryotes and eukaryotes. In embodiments, the microorganism is pathogenic, or is capable of becoming pathogenic depending on its environment (conditionally pathogenic). In embodiments the microorganisms are human or non-human animal pathogens. In embodiments, the pathogens are selected from gram positive and gram negative bacteria. In embodiments the pathogens are obligate intracellular parasites. In embodiments the pathogens are pathogens maintained in a laboratory and are candidates for use as agents for bioterrorism. In embodiments the pathogens are members a following bacterial genus: *Bacillus, Bordetella, Borrelia, Brucella, Campylobacter, Chlamydia* and *Chlamydophila, Clostridium, Corynebacterium, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Vibrio,* and *Yersinia*. In embodiments the microorganism is a pathogenic or potentially pathogenic eukaryote, such as a yeast or other fungus. In embodiments the pathogenic fungus is a member of a following genus: *Candida, Aspergillus, Cryptococcus, Fusarium, Histoplasma, Pneumocystis,* and *Stachybotrys*.

In an effort to deter potential efforts to decrypt the genomic safeguards described herein, the culture medium can comprise one or more other compounds which are referred to herein as "decoy" compounds. Decoy compounds comprise exogenously provided compounds that may have known capabilities to alter gene expression in a microorganism, such as compounds that can induce a promoter or repress gene expression, but the present cultures are configured such that the decoy compounds do not substantially affect their gene expression or growth profiles. Thus, the first and second compounds described above for use as inducers and suppressor compounds can be considered "non-decoy" compounds for ease of reference. In embodiments the culture comprises greater molar concentrations of the decoy compounds relative to the non-decoy compounds. Thus, the decoy compounds can be included in micromolar, or millimolar, or greater concentrations. Any number of decoy compounds can be included. In embodiments, at least one, two, three, four or five decoy compounds are included. Decoy compounds known to regulate gene expression may be of heightened value. Decoy compounds suitable for use in embodiments of this disclosure include but are not limited to the following, and include all combinations of the following: IPTG (isopropyl thioglactoside), virginiamycin, gentamycin, quercetin, lincomycin, 1-Naphthaleneacetic acid, 2,4-DAPG, 3-oxo-octanoyl-L-homoserine (OAH), bepridil, catechin, choline, coumestrol, cumate, d-camphor, daidzein, doxycycline, erythromycin, estradiol, fisetin, fusaric acid, genistein, kinetin, and sodium salicylate.

In another aspect the disclosure includes modified microorganisms that include decoy genetic elements. The decoy genetic elements can comprise genes, such as toxin genes, auxotrophic markers, other RNA coding sequences, but the decoy genes are not affected by the non-decoy compounds. In embodiments, the decoy genetic elements comprise SSRRS, or one or more SSRs that are not active in the modified organisms, or an inducible promoter that is not induced by the non-decoy or the decoy compounds. It will be recognized that decoy genetic elements may affect a transcriptome analysis relative to a non-modified organism of the same type, but the decoy genetic elements are designed so as not to substantially diminish the fitness of the modified microorganisms relative to microorganisms of the same type that are not similarly modified. Additional non-limiting examples of decoy genes include the lad (lac repressor) gene, the camphor repressor, virginiamycin repressor, gentamycin repressor or any of a large collection of known Tet repressor homologs.

In another aspect the disclosure includes a kit for use in controlling growth of a modified microorganism as described above. The kit comprises a plurality of compounds, wherein the plurality of compounds includes the first and second non-decoy compounds described above, and further comprises at least one decoy compound, wherein the at least one decoy compound is included in a molar excess relative to the first and second compounds. In embodiments the kit can comprise at least 2, 3, 4 or 5 or more additional decoy compounds, wherein the additional compounds are each included in a molar excess relative to the first and second compounds. The kit can further comprise a modified microorganism described herein, including in a culture thereof. The kit can comprise separate or a single container (s) for containing the non-decoy and decoy compounds, or the culture, suitable containers being well known in the art. The kit can include one or all of the compounds in a ready-to-use solution, or combinations of the compounds can be provided for use in making a solution for adding to growth medium. The kit can include printed material that describes preparing the compounds for adding to the culture medium, or instructions for adding a composition comprising the compounds directly to the culture medium. In an embodiment, the kit includes pre-made culture media which comprises the non-decoy compounds at a sub-micromolar concentration, and the decoy compounds in a molar excess relative to the non-decoy compounds.

In one embodiment, the disclosure includes the pre-made culture as a product that is independent of the kit, and which can be sold as, for example, a powder, solution or gelatinous substrate suitable for culturing the modified microorganisms, and which includes the decoy and non-decoy compounds.

In another aspect the disclosure includes a method for controlling growth of a population of modified microorganisms described herein, comprising culturing the population of microorganisms in a culture medium that comprises a sub-micromolar concentration of the first and second non-decoy compounds described above, and which can further comprise one or more decoy compounds in a molar excess relative to the first and second compounds, and wherein the decoy compound(s) does not retard the growth of the microorganisms in the population.

In yet another aspect the disclosure includes a method of making a modified microorganism, the growth of which can be controlled using a first and second compound at sub-micromolar concentration in a culture medium as described above, the method comprising introducing into the microorganism: i) a promoter inducible by the first compound, wherein the inducible promoter is operably linked to an RNA coding sequence, transcription of which is essential for growth of the microorganism, wherein the RNA coding sequence does not encode an auxotrophic marker; ii) a pair of site specific recombinase recognition sites (SSRRS) flanking or within the RNA coding sequence such that recombination between the SSRRS disrupts transcription of the RNA coding sequence; and iii) a site specific recombinase (SSR) coding region which is specific for the SSRS, and wherein expression of the SSR is repressed by the second compound; and iv) culturing the microorganism in a culture medium that comprises a sub-micromolar concentration of the first and second compounds. As described above, alternatives to the SSRRS and SSR are available and include endonuclease coding regions and sites that are specifically recognized by the endonuclease. Decoy genes can also be introduced into the microorganism. The disclosure also includes progeny of any of the modified microorganisms described herein.

The following Examples are presented to illustrate particular embodiments of the present disclosure. They are not intended to be limiting in any manner.

Example 1

This Example provides a demonstration of plasmid based chemically regulated transcriptional switches. As a proof of principle, we first constructed a chemically regulated transcriptional switch based on two essential synthetic histone genes called HHTS and HHFS encoding histone H3 and H4 respectively; the "S" refers to the synthetic nature of the genes (described in Dai J, et al. (2008) *Cell* 134(6):1066-1078). In the safeguard strains described here, the HHTS and HHFS genes are regulated by GAL1 and GAL7 promoters, respectively, and each histone transcriptional unit is flanked by a pair of loxP sites as explained further below. Thus the transcription of the same genes can be regulated by the presence of galactose or glucose in the growth medium, or related methods, and the presence/absence of the genes can be regulated by the expression of Cre recombinase activity. This histone-based triplex safeguard was cloned into a pRS415 centromeric (episomal) vector (Sikorski R S & Hieter P (1989). *Genetics* 122(1):19-27)) to construct plasmid pPC012 (FIG. 1).

Figure 7:
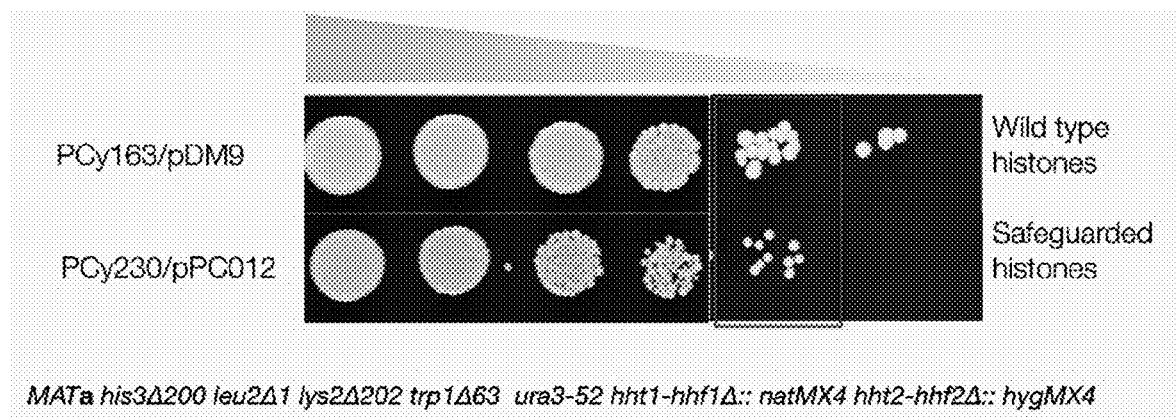
FIG. 7: PCy230 compared with PCy163. Comparison of the colony sizes of centromeric histone-switch safeguard strain PCy230 with wild-type control strain PCy163 reveals severe fitness effect.
Figure 8:
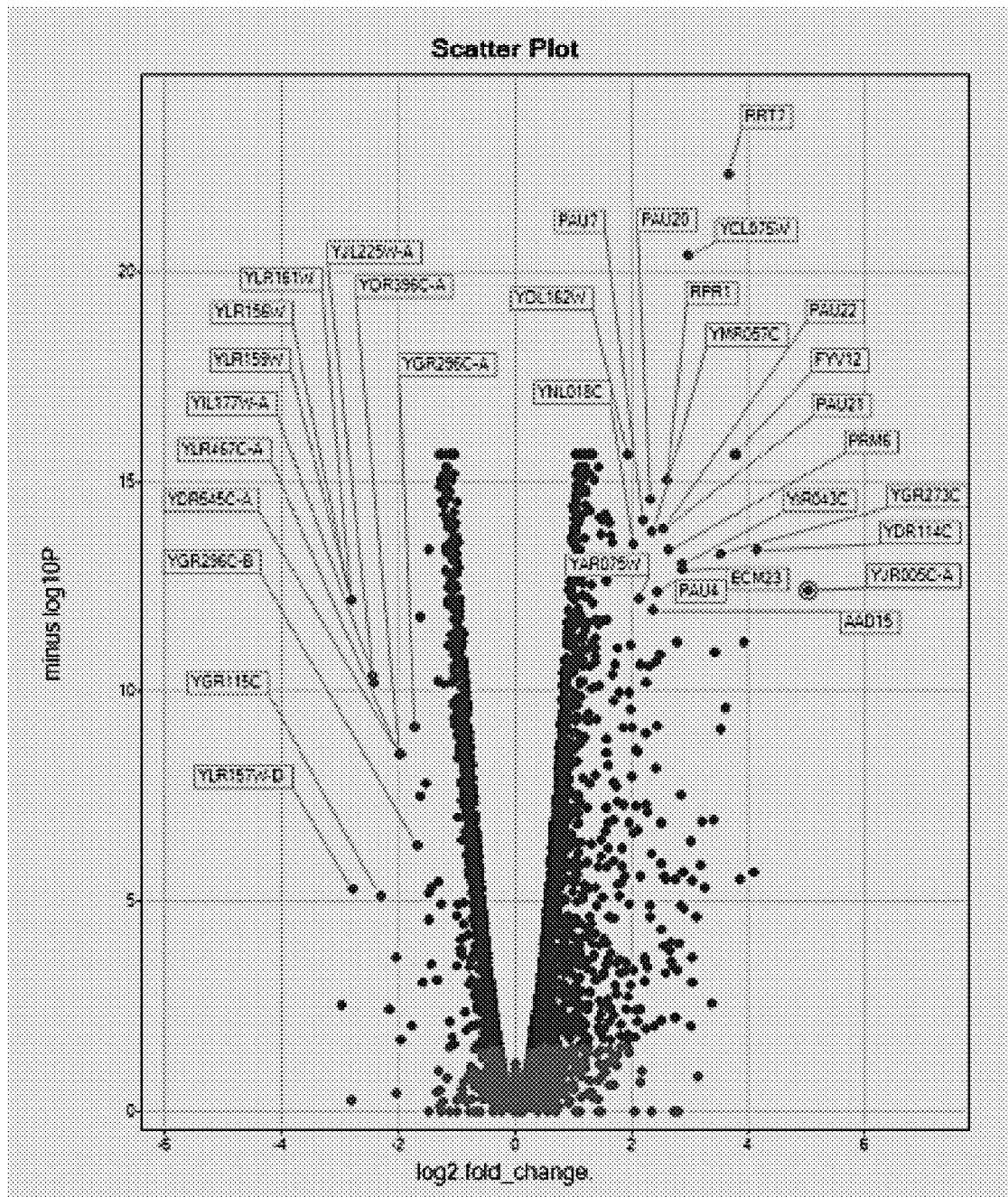
FIG. 8: RNASeq analysis of PCy230. Transcription profiling of centromeric histone-switch safeguard strain PCy230 reveals a large percentage of dysregulated gene expression. Red dots: genes with similar expression levels in the two strains; blue dots: dysregulated genes. The control strain contains pRS415 empty vector, MATa leu2Δ1 lys2Δ202 trp1Δ63 ura3-52 his3Δ200.

To evaluate ability to function as a genome safeguard, we generated yeast strain bearing the construct, PCy230 (his3Δ200 leu2Δ1 lys2Δ202 trp1Δ63 ura3-52 hht1-hhf1Δ:: natMX4 hht2-hhf2Δ:: hygMX4, [pRS415-loxPWT-HHTS-loxPWT-HHFS-loxpWT], see Methods). Strain PCy230 was subsequently plated on both permissive (galactose) and restrictive (glucose) conditions, and the escape (reversion) rate was calculated according to Luria & Delbruck fluctuation analysis using the method of the median (Lea D E & Coulson C A (1949) *Journal of genetics* 49(3):264-285) (Table 5). Although the escape rate was quite favorable at 10-7, we observed a significant fitness defect by comparing the colony size of PCy230 with that of a control strain (FIG. 7). Subsequent transcriptome profiling indicated that a large number of genes were dysregulated, possibly as a result of the combined effects of variations in plasmid copy number and the accumulation of a fraction of cells that had lost plasmid under permissive conditions (FIG. 8).

Example 2

Figure 9:
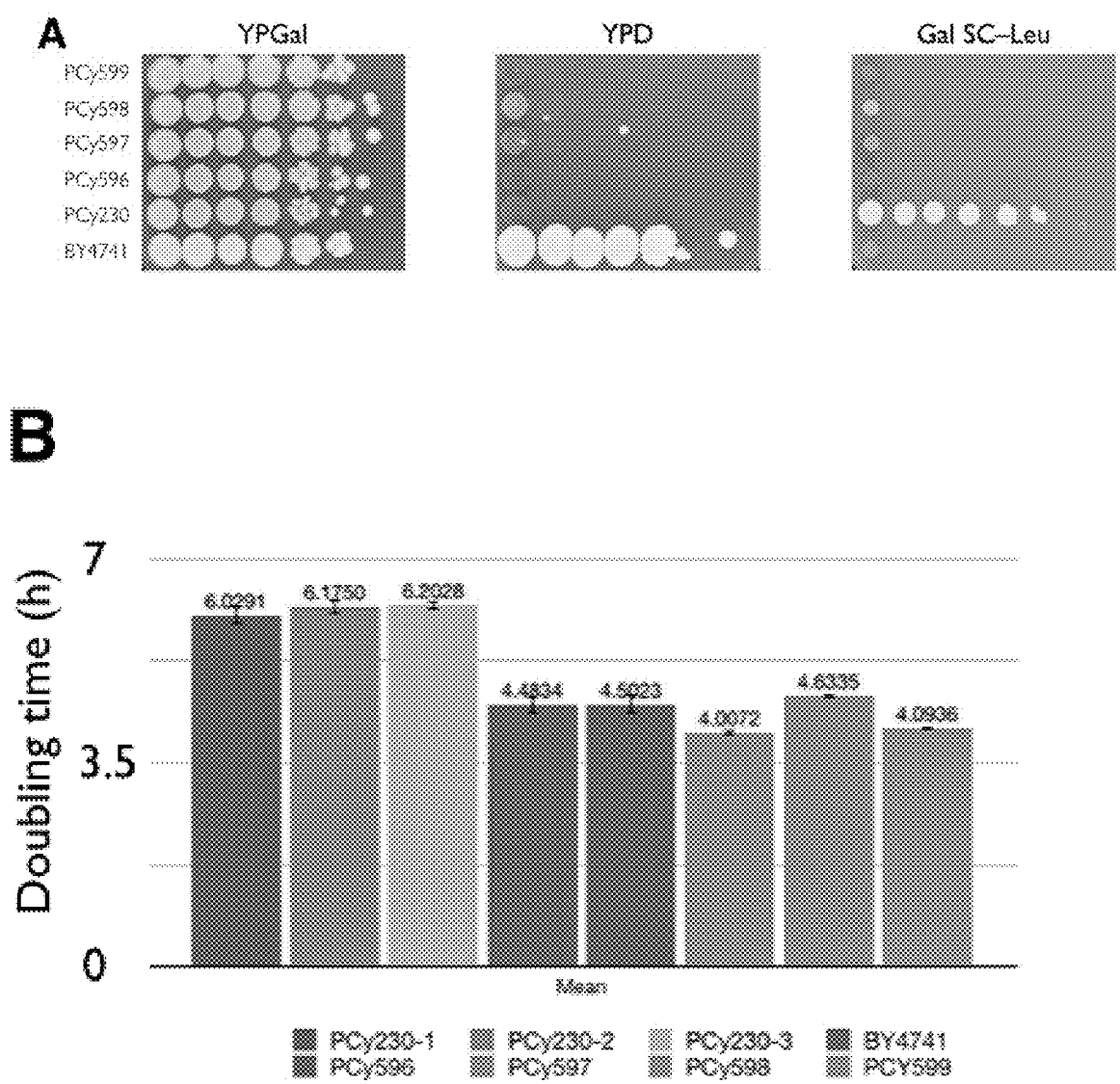
FIG. 9: Comparing SafeGuard Strains with WT BY4741. Comparing the integrated histone switch safeguard strains (PCy596-599) with centromeric histone-switch safeguard strain PCy230, and the wild-type strain BY4741. (A) Colony sizes: The colony sizes of integrated SafeGuard strains are close to the size of wild type WT BY4741, and are significantly larger than PCy230 which contains a plasmid-based SafeGuard switch. (B) Doubling time: The doubling time in galactose media of integrated SafeGuard strains are close to WT BY4741, while PCy230 takes much longer to double. (C) Transcriptome profiling: using the corresponding strain with a wild-type native promoter driving the gene of interest as the control strain, the RNASeq data of integrated Safeguard strains shows very limited changes to transcriptome profiling.

This Example demonstrates that chromosomal integration of histone switches restores fitness. It was hypothesized that the fitness decrease of PCy230 may reflect variations in histone abundance in individual cells as the copy number of centromeric plasmids can fluctuate between 1-3 copies. Alternatively, it was possible that the expression of the two histone genes would give rise to aberrant histone ratios that differed from the native situation, or deviations in expression dynamics between galactose inducible and native histone promoters. Integration of the histone based safeguard into the genome would ensure stable single copy. Thus the histone safeguard (tagged with URA3) was integrated into the HO locus of PCy230, and after spontaneous mitotic loss of the original pPC012 plasmid (tagged with LEU2) on YP-galactose medium, new integrated safeguard strains PCy596-599 were constructed. These integrated safeguard strains have similar low escape rates as PCy230 on glucose (Table 4), yet the fitness and gene expression profiles were significantly improved as determined by measuring colony sizes (FIG. 9A), doubling time (FIG. 9B) and transcriptome profiling (FIG. 9C).

Example 3

Figure 2:
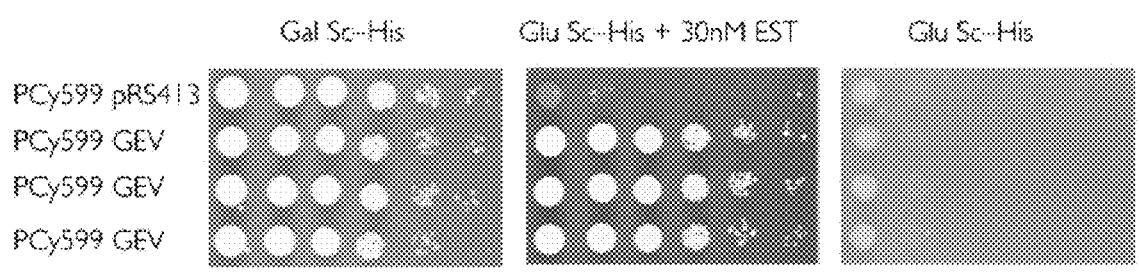
FIG. 2: Regulating histone based safeguard switches with 30 nM estradiol. The GEV regulated histone safeguard strains grow well on permissive medium and die under restrictive conditions. The histone strain PCy599 with GEV plasmid, grows well on both galactose medium and estradiol supplemented glucose medium, and cannot survive on glucose medium without estradiol.

This Example provides a demonstration of regulating transcriptional switches with 30 nM estradiol as one non-limiting example of use of a sub-micromolar concentration of an exogenously provided compound. In this regard, for many applications, a low ligand concentration, and a non-native ligand unlikely to alter cell physiology is desirable. To demonstrate ability to regulate the cell viability using non-native small molecules at nM concentration, we transformed a second plasmid pHCA/GAL4(1-93).ER.VP16 (henceforth called GEV) that produces a GAL4 DBNA binding domain-estrogen receptor-VP16 tribrid protein (GAL4DB.ER.VP16; GEV) (34), into safeguard strain PCy599 to construct strain NAy236. This safeguard strain can be regulated not only by galactose, used at mM concentrations, but also by estradiol, a small molecule non-native to yeast able to maintain viability at sub-micromolar (30 nM) concentrations. The GEV localizes into nucleus and binds to Gal4p consensus sequences to activate transcription of the targeted gene, upon induction by β-estradiol. The GEV protein is retained in the cytoplasm by Hsp90 in the absence of estradiol, resulting in fairly tight control of gene expression. The histone safeguard strains (PCy230 and PCy599) was able to be regulated with 30 nM estradiol on normal glucose-containing yeast growth medium, with an escape reversion frequency of 10-7 to 10-9 (FIG. 2, Table 4).

Example 4

Figure 3:
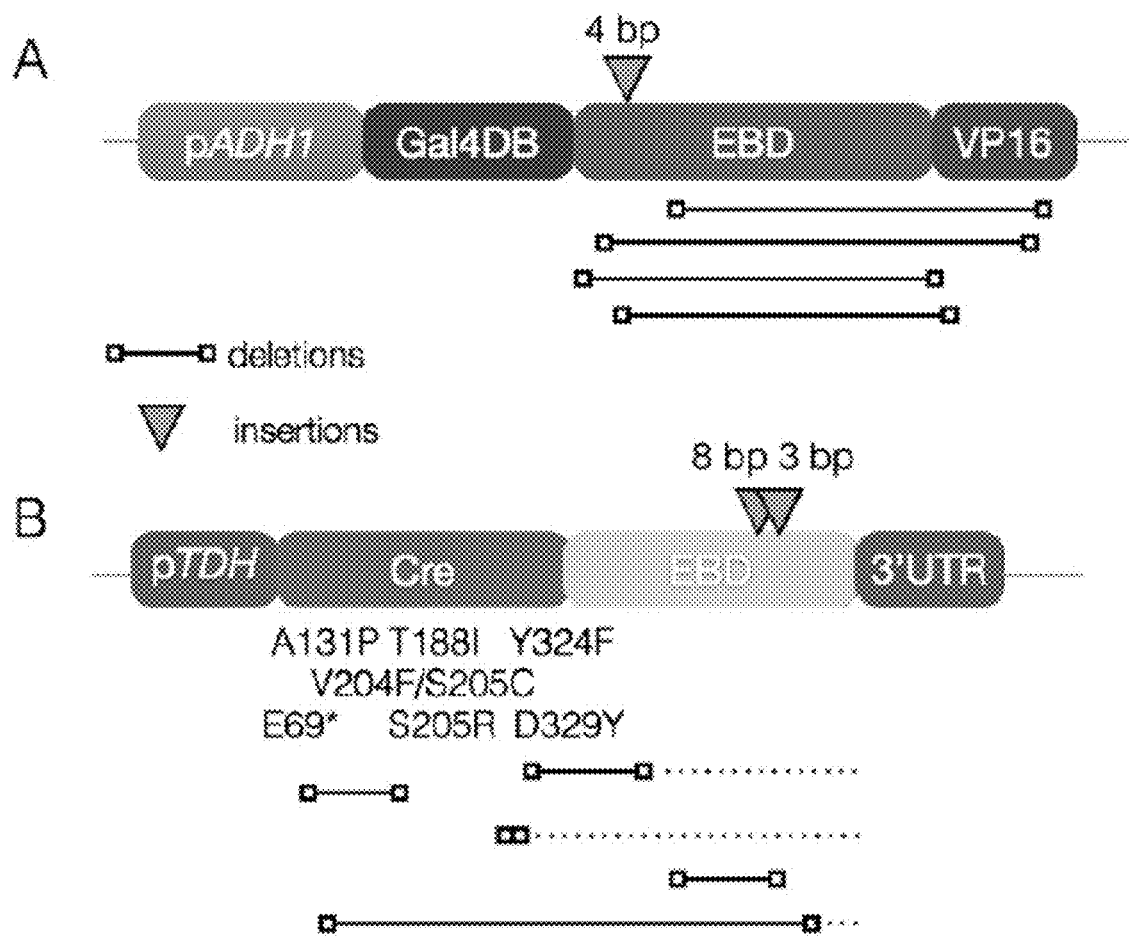
FIG. 3: Escape mutant analysis. Both GEV and Cre-EBD plasmids of escape mutants were isolated and analyzed. (A) Most of the plasmids bore in frame deletions in the hER region that retained the C-terminal VP16 activator sequence. One plasmid had a 4 bp insertion and the protein is predicted to have an out of frame C-terminal tail of 26 amino acids of which five are acidic residues, a sequence which might serve as a transcriptional activator. See Also Table 5. (B) The mutations found in the Cre-EBD constructs are mostly missense mutations in the Cre coding region or deletions (deletions that are also out of frame are indicated by a stippled line for the out of frame segment) in the Cre and/or EBD domains. See also Table 5.
Figure 11:
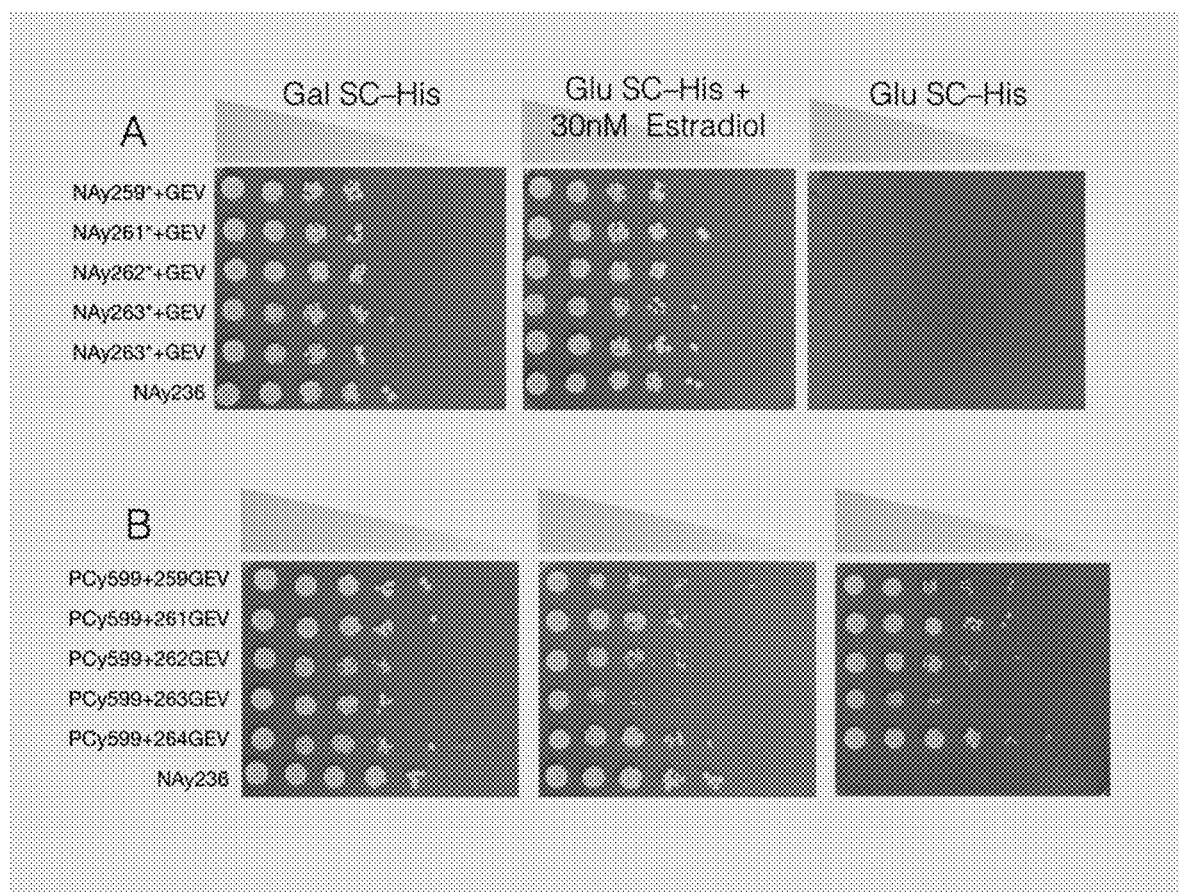
FIG. 11: (A) Restoring wild-type phenotype of GEV escape mutants by retransformation with wild type GEV plasmid. After swapping a wild-type GEV plasmid into the "GEV-less" escape mutant strains (Nay259*−264*+GEV), the phenotype is reverted to normal as the resulting strains grow well on Gal SC−His plates and Glu SC−His+30 nM estradiol plates, but die on Glu SC−His plates. (B) Transforming recovered GEV plasmids from escape mutants into parental strain PCy599 (PCy599+2XXGEV [escape mutant-derived GEV plasmid]). The resulting strains grow on the restrictive condition (Glu SC−His). Note the small colonies of the retransformed escape mutants under the permissive condition.

This Example provides an analysis of escape mutants using GEV regulated GAL-histone transcriptional safeguards as non-limiting examples of aspects of this disclosure. In performing this analysis five independent escape mutants of the GEV-regulated histone safeguard strains were isolated. These strains grow on glucose media in absence of the estradiol. The GEV plasmids from those five escapers were recovered from yeast into E. coli, transformed into the parental strain PCy599, and tested for their ability to recapitulate the "growth in absence of estradiol" phenotype (FIG. 11A), and sequenced with the same primers (Table 2). Many of the escape mutants seemingly grow less well than the parental strain in the presence of estradiol, suggesting there will be selective pressure against their accumulation (FIG. 11A). All five plasmids that recapitulated the phenotype had mutations, mostly large internal deletions in the hER (human Estrogen Receptor) domain of the gene that delete the estradiol-responsive domain but remain in frame with the downstream VP16 (FIG. 3A and Table 5). Similarly, reintroducing a fresh GEV plasmid restored estradiol dependence was also tested (FIG. 11B).

Example 5

This Example provides a demonstration of chemically regulated site specific recombination switches. A chemically regulated Cre (Gibson D G, et al. (2010). Science 329 (5987):52-56); Dymond J S, et al. (2011), Nature 477(7365): 471-476; Lindstrom D L & Gottschling D E (2009) Genetics 183(2):413-422, 411SI-413SI) was adapted and demonstrated to very effectively kill yeast with a semisynthetic genome containing numerous loxP sites flanking a number of essential genes. The specialized Cre protein from Lindstrom D L & Gottschling D E (2009) is tightly regulated both transcriptionally and post-translationally. A daughter cell specific promoter, pSCW11, ensures expression only in the daughter cell state. Furthermore, the Cre is fused to the estrogen binding domain (EBD) which is unfolded in the absence of estradiol, causing it to be retained in the cytoplasm by binding to the Hsp90 chaperone. In this Example, we induced Cre with estradiol, leading to excision of the histone gene(s) and loss of viability. Those skilled in the art will recognize, given the benefit of this disclosure, how to "reverse" this logic, so that the small molecule maintains the viability of the cell. In particular, we transformed the pSCW11-Cre-EBD plasmid into safeguard strain PCy230 to construct PCy251, and induced killing on Gal plates (galactose is required to maintain histone gene expression) with 1 µM estradiol, intended to delete the histone genes, despite their expression. However in this context the killing effect was not as complete as expected. It was hypothesized that this was due to SCW11 promoter strength/expression properties and thus a set of Cre-EBD plasmids by replacing the SCW11 promoter with various constitutive yeast promoters was constructed (see Example 9). After transforming the set of constructed Cre-EBD plasmids into PCy230, and screening on Gal-estradiol plates, pTDH3-Cre-EBD was identified as the best candidate for our approach, as it effectively killed the safeguard strain upon induction but remained inactive in the absence of estradiol. Upon estradiol induction, the Cre protein localizes into the nucleus and excises the histone transcription unit(s) residing between the three loxP sites. The reversion rate of this site-specific recombination-based safeguard was systematically measured, and is less than $10^{-6}$.

Example 6

This Example provides an analysis of escape mutants by determining CRE-EBD sensitivity of GAL-histone recombinational safeguards. In this regard, we evaluated the site-specific recombination regulation of the original GAL-histone safeguard in the presence of a CRE-EBD plasmid by studying escape mutants. We isolated 21 independent escape mutants of the safeguard strains which grew in the restrictive condition of Cre expression, which in this case is galactose containing 1 µM estradiol. The Cre-EBD plasmids were recovered and retransformed into the parent strain PCy599, and the resulting strains were found to be insensitive to estradiol induction, confirming that the responsible mutation resided on the plasmid. The Cre-EBD mutant plasmids were sequenced to identify the mutations leading to the phenotype (FIG. 3B, Table 5), and observed a wide variety of mutations predicted to lead to a loss of function. Of the 21 plasmids, 2 had insertions (of 3 and 8 bp), 7 had missense or nonsense mutations in the Cre coding region, 5 had various deletions in the Cre and/or EBD regions, and finally 7 of them complete lost the Cre-EBD insert instead containing either a single loxP site or loxP sites flanking the histone expression cassette (unlike the parental plasmid, which had none). The latter category of mutant can be explained by assuming there were two copies of the histone plasmid. Without intending to be constrained by any particular theory, it is considered that homologous recombination between one copy of the safeguard plasmid (based on pRS415-LEU2) and the pTdh-Cre-EBD plasmid (based on the largely identical pRS413-HIS3) occurred, producing a Cre-EBD-LEU2 plasmid and a Histone HIS3 plasmid. Upon Cre-EBD induction, an "empty" HIS3 plasmid containing just the loxP site would be produced at high frequency. Subsequent mitotic loss of the Cre-EBD plasmid, a frequent event, would produce the observed configurations.

Example 7

This Example demonstrates that combined escape of transcriptional and recombinational safeguard switches was not observed. To this end, a combined escape experiment was performed by plating yeast strain PCy599 carrying TDH3-Cre-EBD and growing cells permissively, and then plating nearly $10^{10}$ cells on restrictive medium (Glucose+ estradiol). Even after replica plating (i.e. two rounds of growth on restrictive medium), no escaper colonies were observed. It is estimated that the cells went through at least one doubling after hitting the selective plates, possibly more. Thus it is concluded that the reversion frequency was $<10^{-10}$, consistent with the predicted frequency of about $10^{-11}$.

Example 8

Figure 4:
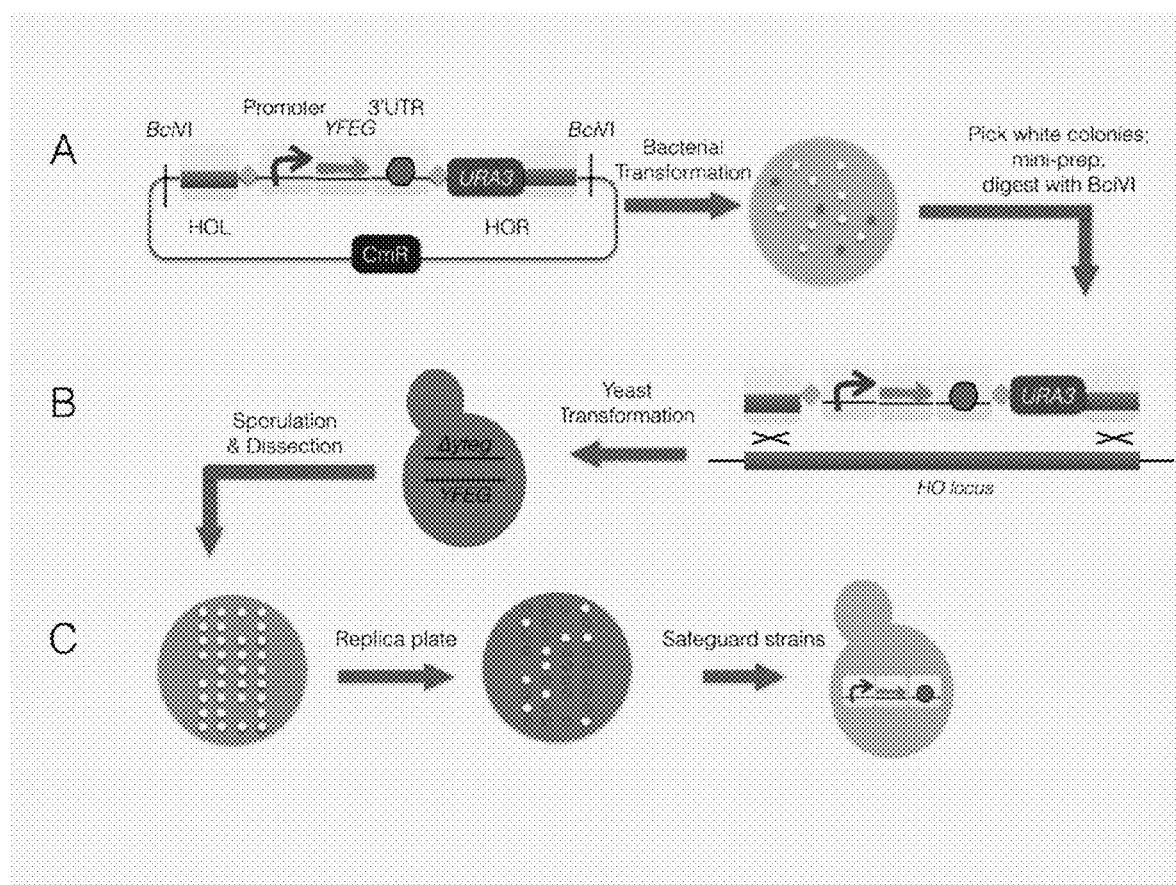
FIG. 4: Construction of multiplex integrated safeguard strains. A Golden Gate assembly based method was developed to construct various combinations of safeguards. A selected essential gene (YFEG, your favorite essential gene) can be quickly assembled with a given promoter and a 3'UTR into an acceptor vector (A, where red colonies are due to vector reassembly (they express RFP) and white colonies are the right assemblies) and integrate into the corresponding yeast mutant (B) to test the behavior of the safeguard strain under both permissive and restrictive conditions (C).

This Example provides a description of construction of additional safeguard switches. To screen for additional essential genes suitable as candidate safeguards, a variant of the Golden Gate DNA assembly method (Engler C, et al. (2009) PloS one 4(5):e5553) was used to efficiently design and construct a systematic set of safeguard switches (FIG. 4). A library of parts (promoters, genes and 3'UTRs) along with a set of acceptor vectors, was constructed and sequence verified. Using a Golden Gate reaction, we assembled 17 essential genes under three different galactose promoters (pGAL1, pGAL7 and pGAL10) respectively.

Figure 5:
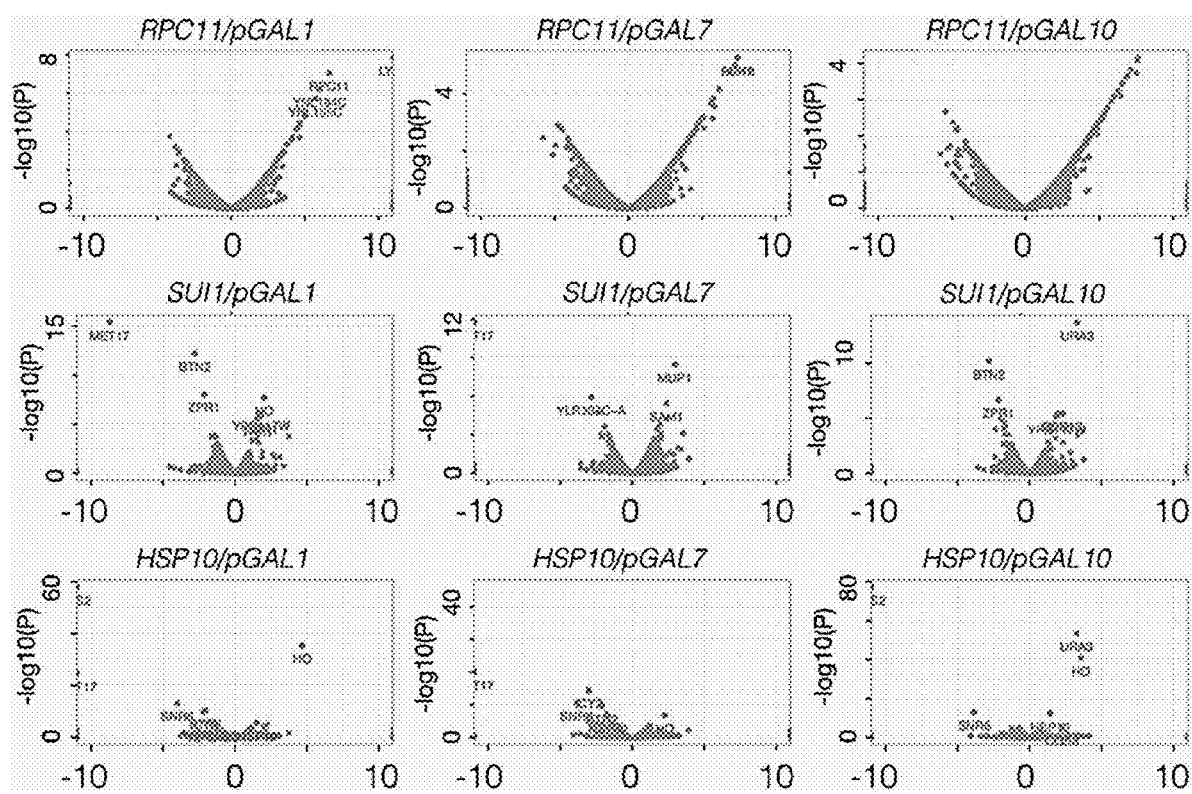
FIG. 5: Transcriptome profiling of safeguard strains. Transcriptome profiling of various safeguard strains. The graph is organized by gene/promoter pairs. Blue dots in the volcano plots represent statistically significant dysregulated genes (see Table 3 for lists of genes affected). The transcriptome profiling shows limited transcriptome changes to the safeguard strains compared with the wild type, with GAL10-RPC11 showing the best performance.
Figure 6:
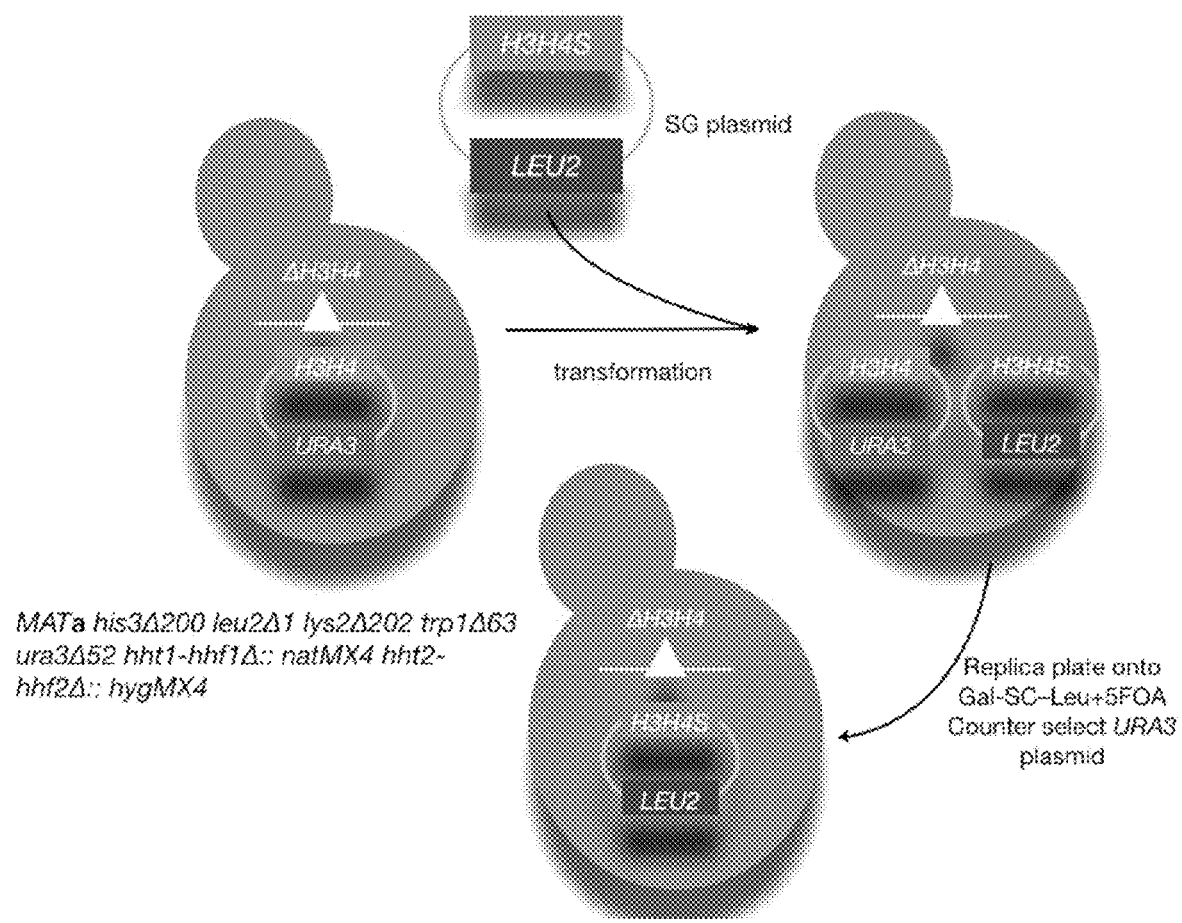
FIG. 6: Installing histone safeguards by plasmid shuffling. The parental strain is a quadruple histone deletion strain, which maintains its viability through a histone plasmid (H3H4-URA3). After transforming a safeguard plasmid which contains histone switches (H3H4-LEU2), and screening for the loss of the original plasmid on Gal SC−Leu+ 5Foa, the desired safeguard strain is obtained.

These were tested individually in the corresponding heterozygous diploid yeast deletion mutant. Diploids transformed with the appropriate test plasmid were sporulated and tetrads were dissected on permissive agar plates, and resulting haploid spore clones were replica plated onto restrictive plates to identify potential safeguard strains. Subsequently three essential genes were identified, namely SUI1, HSP10 and RPC11 as preferred gene candidates by this method. The selection criteria were: 1) the safeguard strain should grow well on the permissive medium and 2) should have a low escape rate under restrictive conditions. Transcriptome profiling was carried out on the constructed safeguard strains to identify potential fitness defects (FIG. 5). The GEV plasmid and CreEBD plasmid were separately transformed into such an RPC11 safeguard strain, to construct estradiol regulated transcriptional switch safeguard strain and site-specific recombination regulated safeguard strains respectively.

Figure 10:
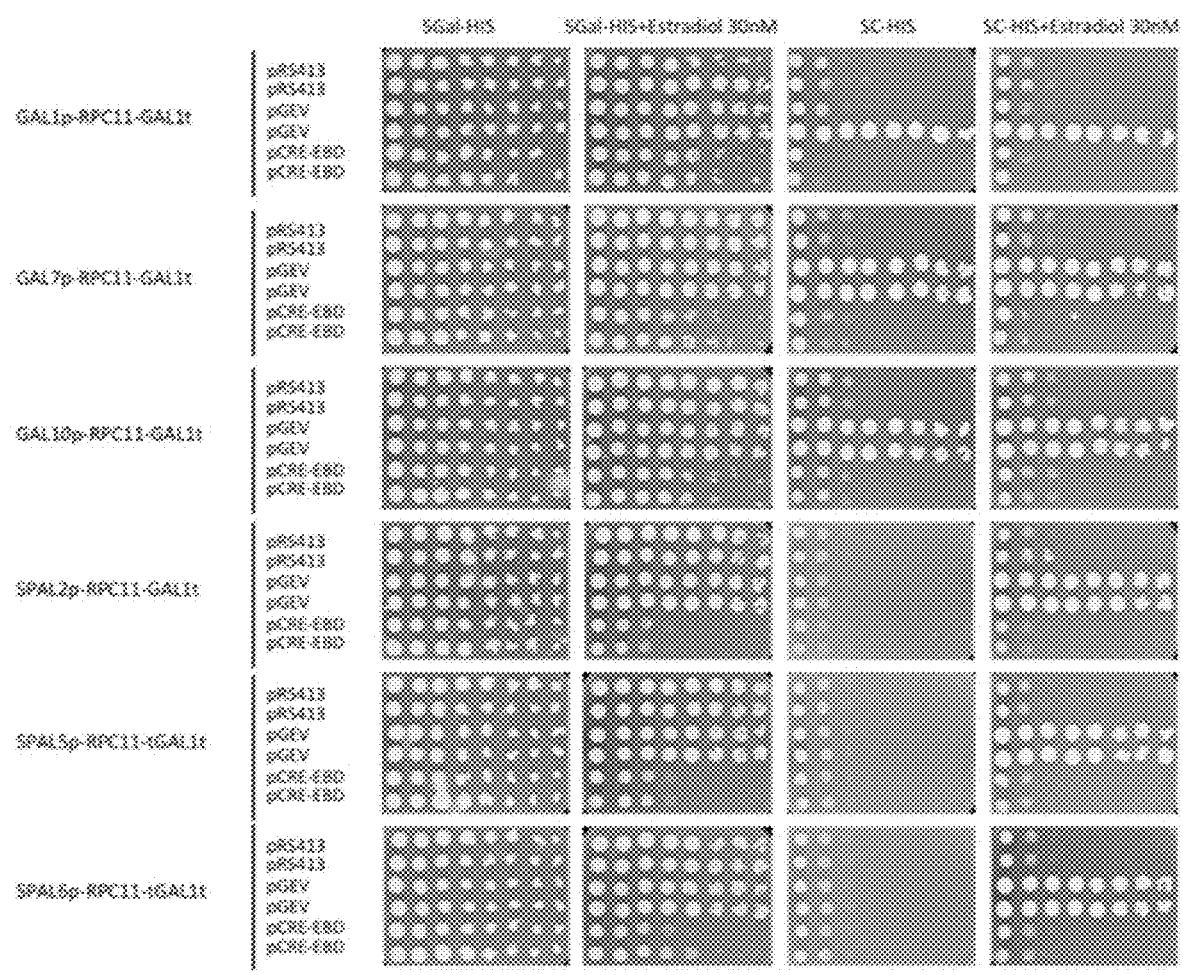
FIG. 10: SpalX promoters more tightly regulate safeguard switches. Serial dilutions of RPC11 safeguard strains expressed under the control of different promoters: GAL1, GAL7, GAL10, SPAL2, SPAL5 and SPAL6. Strains were spotted on the indicated media. In each case the strains were transformed with pRS413 (control empty vector), pGEV or pCRE-EBD. With all of the constructs driven by GAL promoters, when transformed with pGEV the strains grow both in the presence and absence of estradiol. In contrast, with the SPAL promoters, safeguard strains grow on glucose only in the presence of estradiol. All 6 safeguard strains transformed with pCRE-EBD, show slower growth on SGAL−HIS+estradiol, due to loxP recombination and excision of the Safeguard constructs; background growth is presumably the result of a preexisting pool of Rpc11 protein that must be diluted out by several rounds of growth.

This Example also demonstrates reducing leakiness of new safeGuard switches. We discovered that the non-histone based GEV-regulated safeguard strains grew under restrictive conditions, and hypothesized that this resulted from leakiness of the galactose promoters (pGAL1/pGAL7/pGAL10) in this context, where lower amounts of the protein products might be required for viability than for histone genes. Various numbers (2 to 10) of Gal4 binding sites have been fused to the SPO13 promoter, which contains a repressive URS sequence, to generate a set of tightly regulated galactose dependent promoters called SPAL promoters (SPO/GAL). We retrieved this set of promoters from strains containing such promoters (see Example 9), and used them to construct a second generation of safeguard strains based on RPC11. The resulting safeguard strains had the appropriate growth phenotypes compared to those with native galactose promoters (FIG. 10).

Example 9

The Example provides a description of the materials and methods used to obtain the results described in the foregoing Examples.

Strains, Plasmids and Oligonucleotides

Yeast strains and the plasmids contained are listed in Table 1. Oligonucleotides used are listed in Table 2.

Plasmid Shuffling

Plasmid pPC012 was transformed into a yeast strain, JDY6, from which all four genomic copies of histones H3 and H4 genes had been previously deleted with viability maintained by plasmid pDM9, a plasmid carrying the URA3 marker and wild-type histone H3 and H4 genes HHT 1 and HHF1. After introducing pPC012, a centromeric (CEN) LEU2 plasmid, into the strain by LioAc/SS/PEG transformation, plasmid shuffling on 5-fluoro-orotic acid (5Foa) 2% galactose medium was successful, indicating that the GAL promoters could successfully express the two histone genes. Such 5-FoaR strains were unable to grow on glucose, consistent with effective shutoff of histone gene expression.

Golden Gate DNA Assembly

The golden gate assembly protocol is described in Engler C, et al. (2009) *PloS one* 4(5):e5553. Specifically, a 15 µl golden gate reaction containing 1.5 µl 10× T4 DNA ligase reaction buffer (New England Biolabs, Ipswich, Mass.), 0.15 µl 100× Bovine Serum Albumin (BSA, New England Biolabs, Ipswich, Mass.), 1 µL 600 units/µL T4 DNA ligase (Enzymatics, Beverly, Mass.), 10 µl H2O, 1 µl acceptor vector DNA (~100 ng/µl) and 0.5 µl insert DNA (~100 ng/µl). The following temperature cycles were used: 1 hour at 37° C., 5 min at 50° C., 5 min at 80° C. followed by incubation at 4° C. 1 µl of the finished golden gate reaction was transformed into 100 µl Top10/DH5α chemical competent cells.

Plasmid Recovery from Yeast

Plasmid recovery from yeast was carried out using a Zymoprep yeast plasmid miniprep kit (Zymo Research, Irvine, Calif.) following the manufacturer's instructions.

Cloning and Sequencing of SPALX Promoters 12 yeast MAV strains (Vidal M, et al. (1996) *Proceedings of the National Academy of Sciences of the United States of America* 93 (19): 10315-10320) containing various numbers of Gal4 binding sites were used as template to clone out SPAL promoters with varying numbers of Gal4 binding sites. Genomic DNAs of these yeast strains were extracted using phenol/chloroform isolation method. Two rounds of PCR were used to amplify the SPALX promoters from gDNA: first, F primer PC_oligo379 and Ura3 R primer PC_oligo380 were used; then the PCR product was diluted 1000 fold. Primers PC_oligo401 and PC_oligo324 were used to amplify the SPAL promoter fragments with appropriate Golden Gate overhangs. The PCR products were cloned using a Zero Blunt Topo kit (Life Technologies, Grand Island, N.Y.). The resulting plasmids were sequenced to identify the exact number of Gal4 binding sites. These promoters were used in subsequent assembly of safeguard switches to identify tighter constructs.

β-Estradiol Induction of Cre Expression

Safeguard strains were grown up on appropriate selective growth medium, then either plated or spotted on appropriate selective solid medium containing 1 µM β-estradiol, and incubated at 30° C. for 2-3 days.

β-Estradiol Induction of GEV System

Safeguard strains were grown up in appropriate glucose selective growth medium containing 30 nM β-estradiol, then either plated or spotted on appropriate glucose selective solid medium containing 30 nM β-estradiol (or restrictive plates lacking estradiol), and incubated at 30° C. for 2-3 days.

Reversion Rate Measurement and Colony Picking for Sequencing

Escape rates were calculated using the method of the median (Lea D E & Coulson C A (1949) 49(3):264-285, the disclosure of which is incorporated herein by reference). For measurement rates in the 10-5 to 10-9 range, 5-12 independent cultures (each grown from a single parent colony) were inoculated into 20 mL SC–His supplemented with 2% galactose in liquid cultures. 108 and 107 cells were plated on restrictive medium. Viable titer was determined by plating 100 µL of a 5-6 serial 10-fold dilution on permissive medium. The reversion frequency was obtained by dividing cfus (colony forming units) on restrictive plates by cfus on permissive plates. The median reversion frequency was then used to calculate the rate using the method of the median.

For each safeguard strain to be measured, 5 "escaper" revertant colonies were picked from independently grown cultures and grown up in 10 mL permissive liquid culture (with plasmid selection if applicable), for 48 hours at 30° C. 10 fold serial dilutions were plated on restrictive and permissive agar plates, and incubated at 30° C. for 2-3 days until single colonies appeared. One colony was chosen per culture to assure independence.

RNASeq

A single colony was picked and grown up in 10 mL permissive liquid medium, and incubated at 30° C. until the A600 was between 0.8 and 1.2 and RNA was isolated as described using a Qiagen RNAEasy kit using the manufacturer's protocol. We performed RNA-seq of strains integrating the histone, RPC11, SUI1 and HSP10 safeguards. mRNA was sequenced using an Illumina HiSeq and standard TruSeq preparation kits. For each strain we obtained approximately 12 million 50 bp single end reads. Reads were mapped using TOPHAT to the reference *S. cerevisiae* genome (S288c). Approximately 95% of the reads were mapped. For each gene, read counts were computed using HTSEQ and analyzed for differential expression using DESEQ, with standard parameters and following the no replicates scenario. For each gene, a raw p-value was obtained and an adjusted p-value using the standard Benjamini-Hochberg procedure (Benjamini Y & Hochberg Y (1995) *Journal of the Royal Statistical Society. Series B (Methodological)* 57(1):289-300). The 1% False Discovery Rate (adjusted p-value≤0.01) was used to identify genes that are significantly differentially expressed. Differentially expressed genes are reported in Table 3.

Example 10

As will be apparent from the foregoing, Examples 1-9 demonstrate engineering of a yeast strain carrying multiplex biocontainment combining transcriptional and recombinational based safeguards, reaching an escape rate of less than $10^{-10}$. This was achieved with transcription control of a single essential gene with an escape rate of $10^{-6}$; however, this could potentially be lower with modifications of the safeguard construct that will be apparent to those skilled in the art, given the benefit of the present disclosure. This and the following Examples provide aspects of this disclosure that comprise such modifications. In particular, this and the following Examples describe efforts to determine what are believed to be the best acting transcriptional safeguard for yeast cells, and a construct(s) achieving the following criteria were sought: fitness approaching the wild type in permissive conditions, lowest possible escape rate under restrictive conditions and essential growth supplement in a nanomolar scale. This and the following Examples describe analysis of a library of essential genes to, without intending to be bound by any particular theory, find the best candidates. Combinatorial assembly was used to screen for what is believed to be the best acting regulatory elements, and genetic engineering was used to modify and improve the safeguard constructs. In addition, an analysis was performed of possible regulators and decoy compounds for use in growth media masking the proprietary components, which permit growth of the safeguarded strain, but do not themselves affect fitness.

Figure 18:
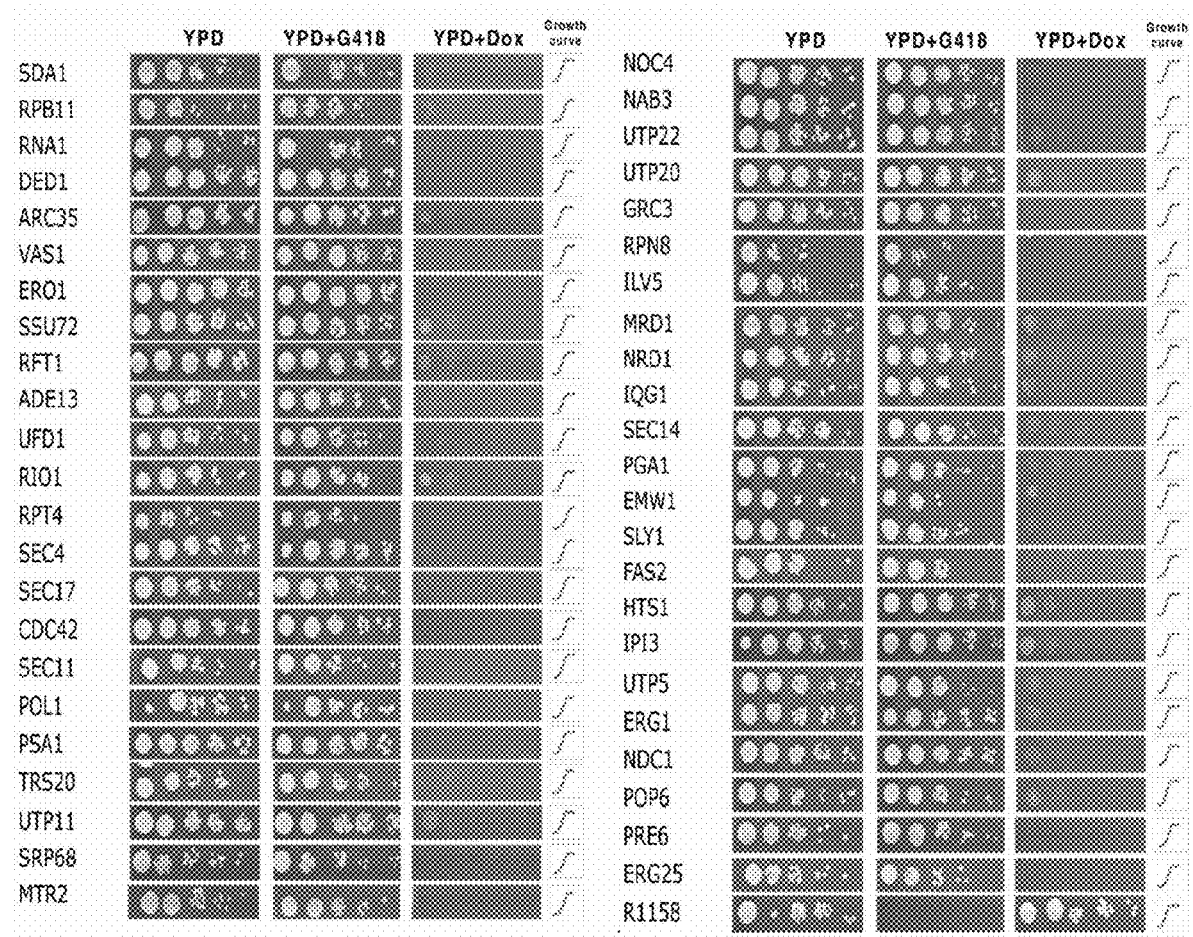
FIG. 18: Fitness analysis of the 47 strains chosen from the Yeast Tet-Promoters Hughes Collection. Serial dilutions of cells on YPD, YPD+G418 and YPD+10 μg/mL Doxycycline. The right row shows graphic representation of the strain growth curve measured in YPD medium. WT strain is marked as R1158.

The transcriptionally regulated safeguards as described in Examples 1-9 above comprise a promoter regulated by an externally supplied ligand, driving the expression of one or more essential genes. To meet the requirements of robust growth in the presence of the ligand and essentially complete failure to grow or loss of viability in the absence of ligand, the genes believed to be best adapted to the purpose were sought, as described in this and the following Examples. Such genes are expected to tolerate a certain variation in their expression without a fitness penalty, but stop growing entirely, or lose viability when expression falls below a certain threshold—i.e. they should not display leaky growth when minimally expressed. To identify potential safeguard essential genes, 250 strains from the Yeast Tet-Promoters Hughes Collection (yTHC) annotated as having a "Severe" or "Very Severe" phenotype on Doxycycline in a "Tet-OFF" strain background (Mnaimneh S, et al. (2004) *Cell* 118(1):31-44) were selected. These 250 strains as well as a WT control (Strain R1158) were grown in YPD medium, diluted serially and plated on YPD, YPD+G418 (validating for the presence of the integrated tet promoter cassette) and YPD+10 μg/mL Doxycycline. All strains grew as expected both on YPD and on YPD+G418, but, showed various colony sizes (fitness) in the presence of doxycycline. In addition, the different strains also showed various fitness levels in the presence of doxycycline. From the 250 strains initially chosen for this analysis 47 strains were selected for further analysis, all of which showed high fitness (similar to WT) on YPD, and low fitness in the presence of Doxycycline (FIG. 18).

Example 11

This Example provides a description of building shuffle strains for combinatorial screening of SG strains. Because the safeguard strategy relies at least in part on using essential genes, the safeguards (SGs) transcription units (TUs) are introduced into a yeast strain that already expresses the gene of interest. Having the unguarded copy of the gene on a URA3 shuffle plasmid allows quick and efficient spontaneous plasmid loss in the presence of ligand, leaving only the safeguarded copy. Thus 49 haploid shuffle strains were constructed, each carrying a deletion of each essential gene as well as a shuffle plasmid with a wild type copy of the essential gene and a URA3 marker, enabling its loss using 5-Foa counter selection.

Figure 12:
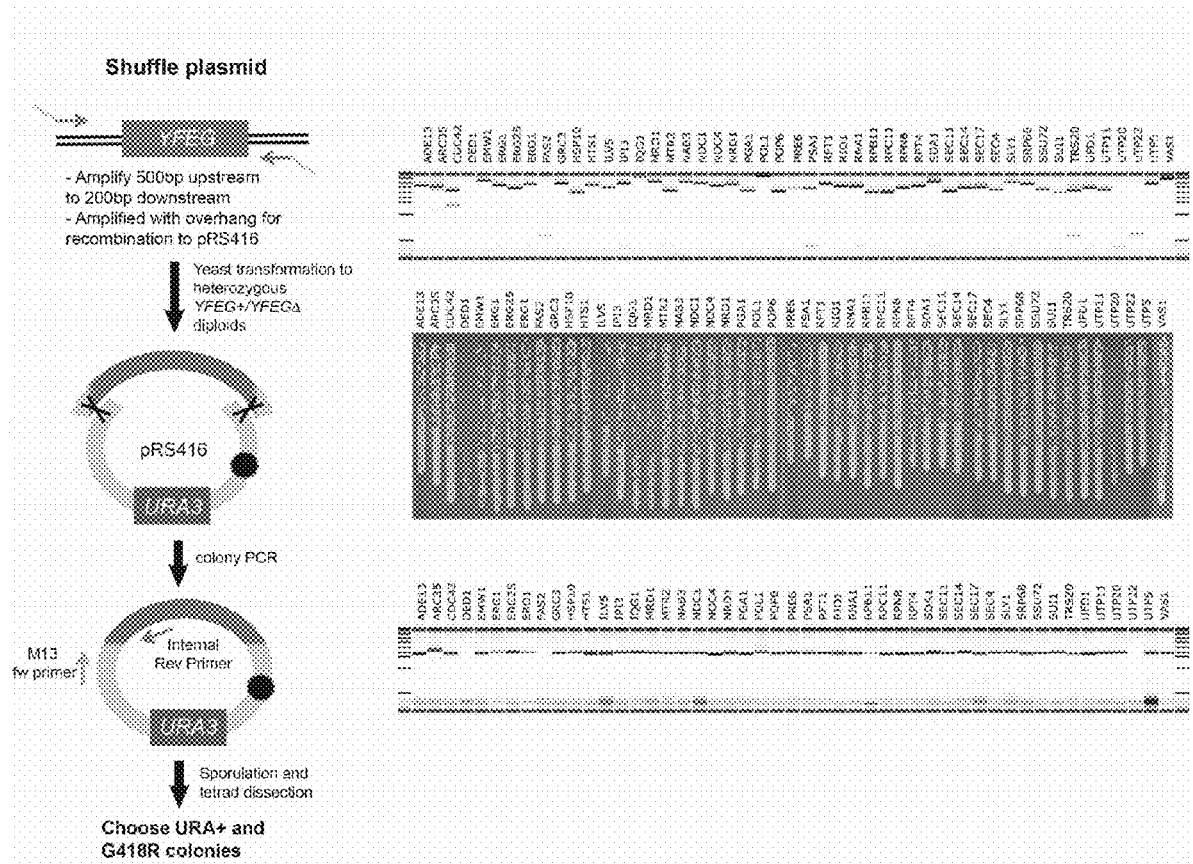
FIG. 12: Outline of steps to create shuffle strains. Genes were amplified from the yeast genome with 500 bp upstream and 200 bp downstream as well as 50 bp in each end for recombination with the pRS416 vector. SmaI digested pRS416 and each amplified gene were transformed into the appropriate heterozygous diploid strain. Transformations (30 μL) were dripped onto Omnitrays and single colonies were picked. Shuffle plasmid cloning was verified using plasmid primers and a gene internal primer. Following plasmid verification all strains were sporulated and G418 resistant Ura+ colonies were saved (both MATa and MATalpha strains were saved).

To create shuffle plasmids for each candidate gene we amplified the corresponding CDS from the genome with 500 bp upstream and 200 bp downstream sequences, to include the native promoter and terminator sequences. The primers used for the genome amplification include 50 bp overhangs, which served as recombination sites with pRS416 (FIG. 12). Each PCR product was transformed with linearized pRS416 (CEN, URA3) into a diploid strain heterozygous for the corresponding essential gene. Homologous recombination between the PCR product and the vector facilitated construction of a shuffle plasmid containing URA3 and the essential gene in vivo (FIG. 12). These Ura$^+$ diploids were sporulated and dissected to isolate "shuffle strains": haploids containing the shuffle plasmid and with the essential gene of interest deleted from the genome. Out of the 49 candidates, shuffle strains for 45 potential SG strains were successfully constructed.

Example 12

This Example provides a description of combinatorial yGG assembly of safeguard constructs and screening for candidate SG strains. Having the ability to combinatorially assemble transcription units (TUs) provides many more variants for testing than could be made one at a time. Thus, assembly of the SG constructs was carried out using a combinatorial yeast Golden Gate (yGG) assembly to screen the best candidates in yeast. All the parts (promoters, essential genes CDSs and terminators) were amplified with the proper yGG overhangs from the yeast genome. For each essential gene a one pot yGG assembly was performed, adding 6 distinct galactose-regulated promoters [GAL1, GAL7, GAL10, SPAL2, SPAL5 and SPAL6 (Vidal M, et al. (1996) *Proceedings of the National Academy of Sciences of the United States of America* 93(19):10315-10320], GAL1 terminator and acceptor vector (pAV10.HO5.loxP). Following yGG assembly, the reaction mix was transformed into bacteria and grown in liquid medium for a bulk plasmid prep which was digested to evaluate assembly efficiency.

Figure 19:
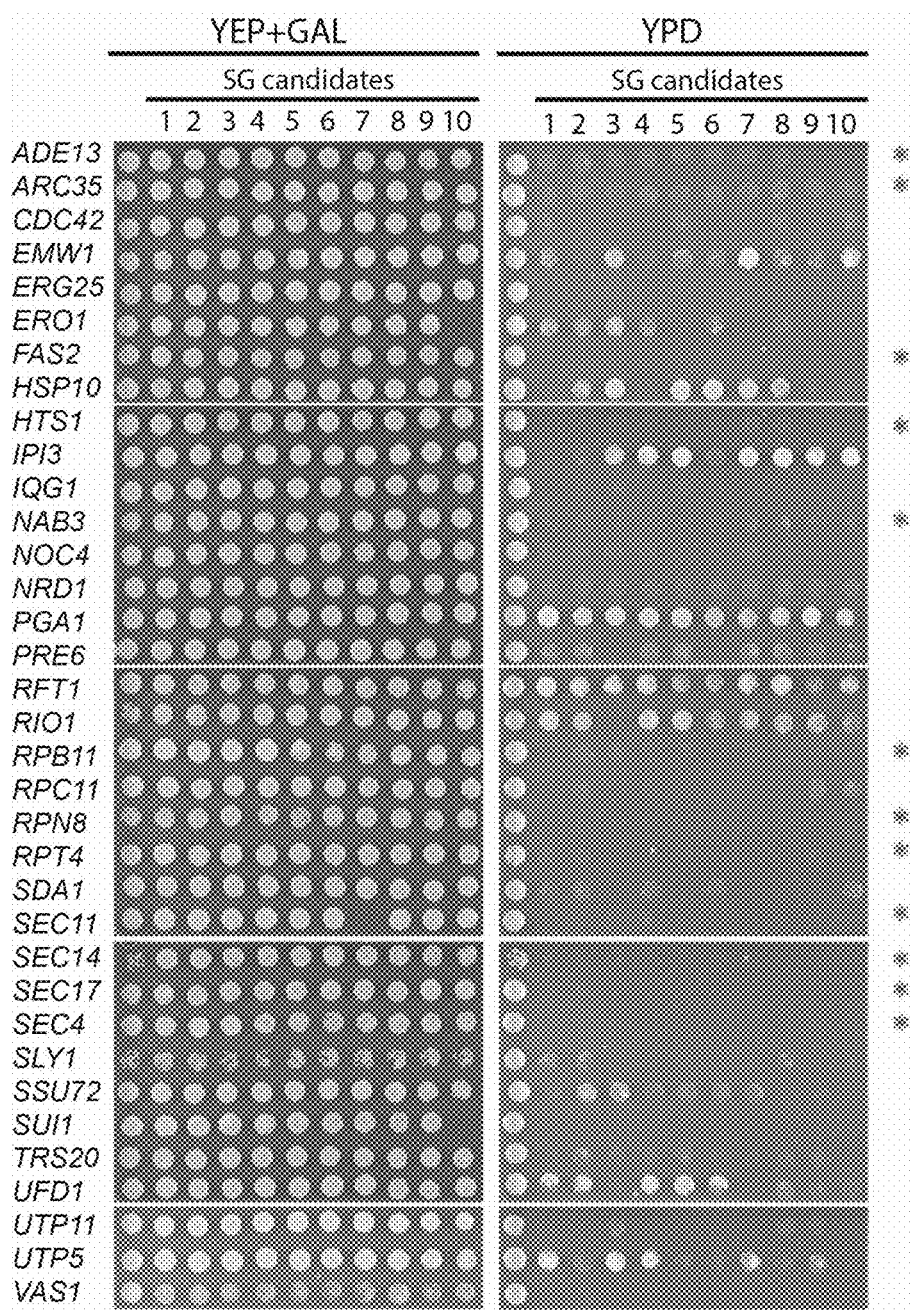
FIG. 19: Screening for the best SG strain after integration of the SG construct. Following transformation into the shuffle strains, and plating on 5FOA, 10 isolates from each essential gene were examined by plating on YEP–GAL vs. YPD. 12 best performing strains (marked by asterisk), were chosen for GEV plasmid transformation.
Figure 20:
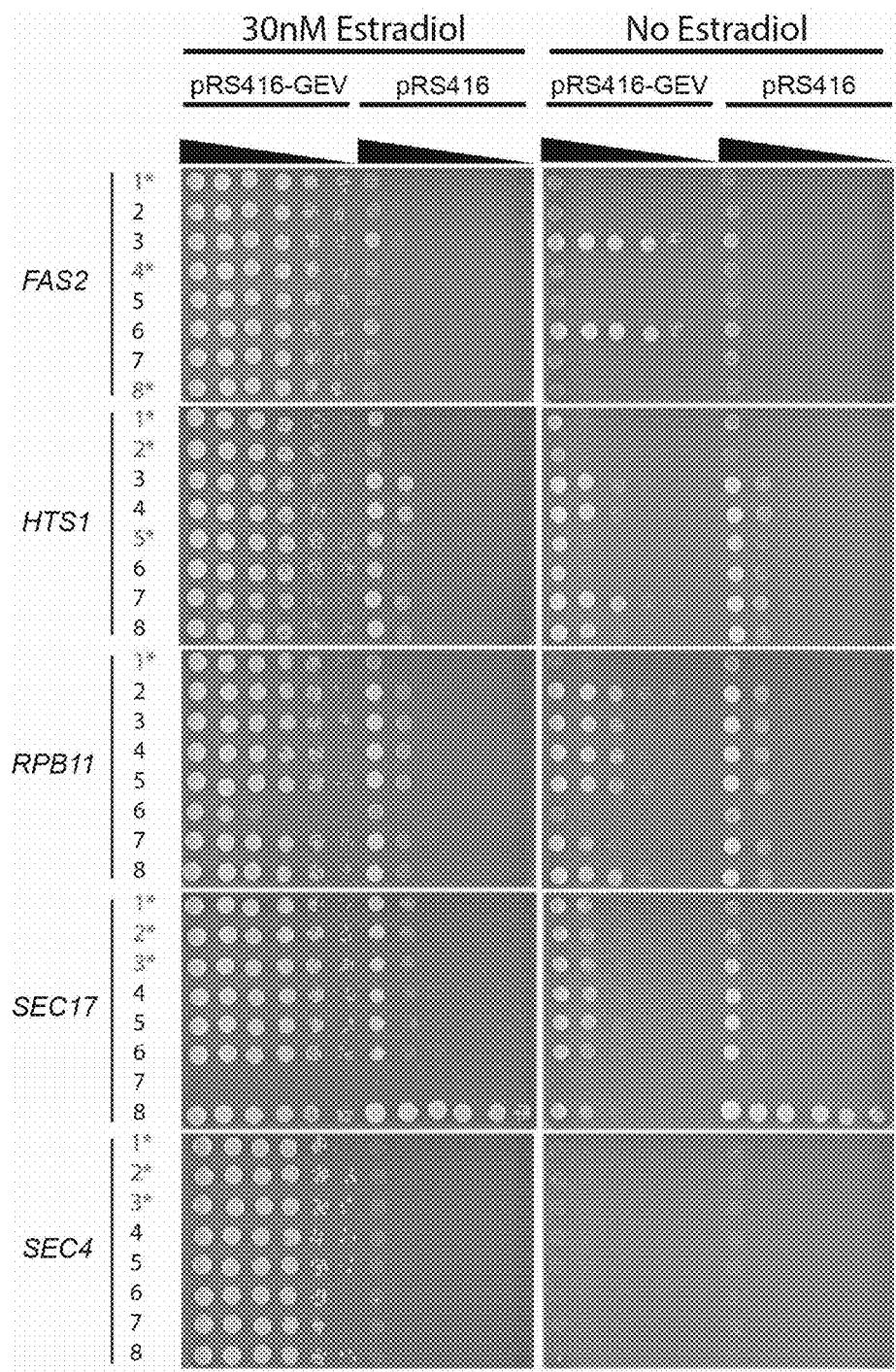
FIG. 20: Growth of safeguard strains. 8 isolates from each SG strain were transformed with GEV containing plasmid and analyzed using a dot assay on Dextrose without Estradiol. Good candidates are marked with asterisk and the candidates that were chosen for further analysis are marked in red.

Following combinatorial yGG assembly and verification, each assembly was transformed into its corresponding yeast shuffle strain. Transformations were plated on SGal−Leu to allow expression of the promoters and to enable loss of the shuffle plasmid. Transformation plated were then replica plated to SC+5-Foa 2% galactose plates. In most cases the majority of the colonies were 5-Foa resistant. 10 isolates were chosen from each gene and were plated on YPD and YEP−GAL to assess their ability to serve as a safeguard strain (FIG. 19). There are differences between genes as well as between candidates of the same gene, presumably reflecting different promoter properties. The 12 candidate genes were chosen that perform best (grow well on YEP+GAL and show low background growth on YPD) (FIG. 13A). 8 isolates from each of the 12 essential genes were chosen, and were subsequently transformed with pRS416-GEV which expresses the GAL4-estrogen binding domain-VP16 transcriptional activator, which is activated by low concentrations of estradiol (McIsaac R S, et al. (2011) Molecular biology of the cell 22(22):4447-4459). Transformation was performed and each strain was transformed with empty vector as a negative control. The optimal SG candidates as determined in this manner should grow well with Estradiol and should show a very low or no growth on Dextrose without Estradiol. FIG. 13B shows the best 5 strains out of the 12 essential genes plated on dextrose supplemented with 30 nM Estradiol vs. Dextrose without estradiol. As shown in FIG. 20, there were a large number of good candidates strains to choose from. 3 strains were selected from each of the 5 SG shown in FIG. 20 (Except for RPB11 that had only one good strain).

All 13 strains were examined for their doubling time in dextrose supplemented with 30 nM Estradiol. They were all compared to their corresponding shuffle strain (FIG. 13C). Similarly to the Histone SG strain described above, all SG strains show a slight increase in doubling time compared to the shuffle strain. Out of the 13 one SG strain was selected for each essential gene to follow up with an escape (reversion) rate experiment, as a test for optimality, and identification of the promoters.

Example 13

This Example describes measuring fitness of SG strains. Due to the fact that these strains were created in a combinatorial assembly strategy and chosen from a pool of safeguards, we decided to evaluate performance in both a MATa and MATα backgrounds. This was done using yeast Golden-Gate (yGG) assembly and transformed into yeast as described above. Candidates were plated on media with or without 30 nM Estradiol for verification. The results were similar to the counterparts made using combinatorial assembly (Data not shown) in both mating types. To evaluate fitness of the strains we measured their growth rate and calculated their doubling time compared to WT strain carrying the GEV plasmid (FIG. 14A). Growth rate in all three safeguard strains shows only a very modest difference from the control strain.

Figure 14:
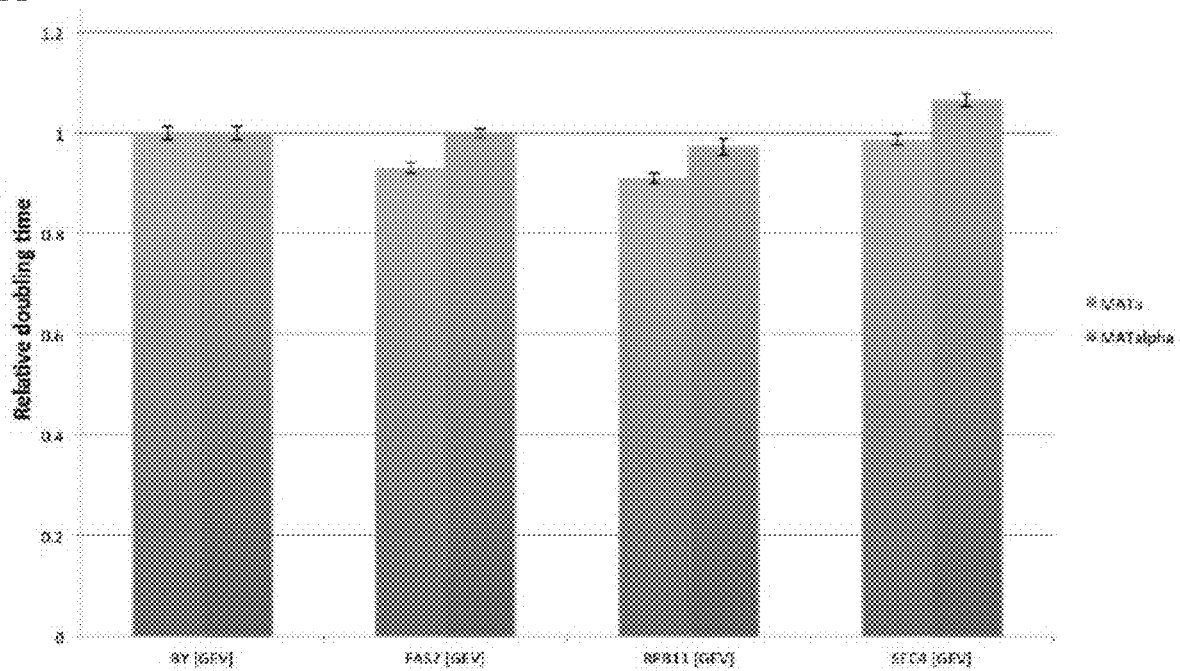
FIG. 14: MATa and MATα SG strains compared to WT strain with GEV plasmid. (A) Graphic representation of relative doubling time of SG strains compare to WT with GEV plasmid. Liquid cultures were diluted and subjected to OD measurements every 10 min in a 24 hrs period. Growth curve was created and doubling time was calculated for each strain. The experiment included 3 independent cultures for each strain in order to calculate SD. (B) Transcriptome profiling of the various safeguard strains. The graph is organized by gene/promoter pairs. Red dots in the volcano plots represent statistically significant dysregulated genes (see Table 7 for lists of genes affected). Blue labeled dot represents SG gene in each sample. The transcriptome profiling shows limited transcriptome changes to the safeguard strains compared with the wild type. (C) Metabolomics analysis presented as a hit-map of the fold change from each metabolite analyzed. MATa Safeguard strains: NAy407 (FAS2), NAy409 (RPB11) and NAy411 (SEC4), MATa control—NAy461. MATα Safeguard strains: NAy408 (FAS2), NAy410 (RPB11) and NAy412 (SEC4), MATα control—NAy462.

In order to examine the difference between safeguard strains and control we preformed transcriptome and metabolomics profiling (FIG. 14 and Table 7). Transcriptome analysis showed that in most of the SG strains there are 0-7 genes, which show a significant change in transcript level (Table 7). Only one SG strain, RPB11 MATa, showed a larger number of transcripts that changed significantly compared to the control strain.

For metabolomics profiling each strain was compared to a WT strain carrying the GEV plasmid. FIG. 14C shows a hit-map of the different metabolites and their fold difference compared to their control. In all strain (both MATa and MATα) there is almost no detectable difference compared to the control stain. In agreement with the transcriptome and growth rate analysis these safeguard strains show no significant differences from the control strain.

Fitness was measured compared to a control carrying the GEV expression plasmid. This was done based in part on the observation that expression of the GEV construct causes a global activation of Gal-UAS regulated genes and thus reduces growth rate of the strain (McIsaac R S, et al. (2013) Nucleic acids research 41(4):e57). This is addressed further below. In addition, the escape rate of an SG strain was measured; all 5 SG strains were less than $10^{-7}$ escapers per cell division (Table 6).

Example 14

Figure 21:
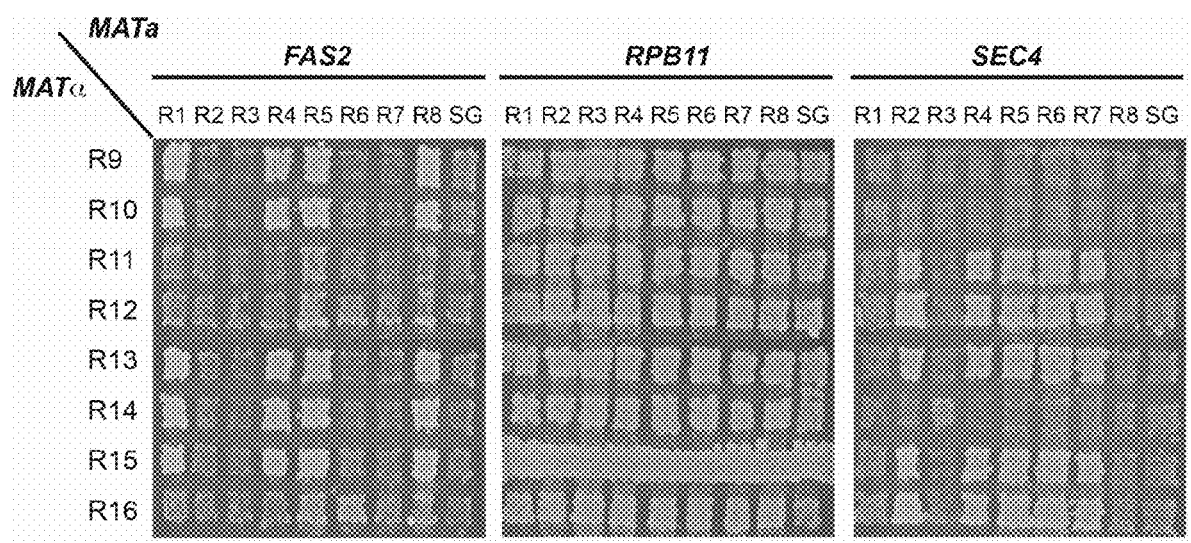
FIG. 21: Escaper complementation groups analysis. 16 escapers (MATa R1-R8 and 8 MATα R9-R16) from each SG were picked and crisscrossed on SC-Ura with 30 nM Estradiol. Diploid were selected by replica plating to SC-Met-Lys-Ura with Estradiol and replica plated to SC-Ura to check for complementation groups. The last row in each plate was the original SG to check for dominance.

This Example provides a description of analysis of escapers. Escape rate experiments were performed on the presently described safeguard strains; 16 independent escapers were isolated from each strain (8 MATa and 8 MATα). For complementation group analysis, strains were replica plated in crisscross to allow for mating at the junctions (FIG. 21). Mating was done in permissive medium containing estradiol, and then replica plated to restrictive medium selecting for diploids with estradiol and finally replica plated to medium lacking estradiol for analysis of complementation groups. Escapers that originated due to a recessive mutation in the same gene will not complement and thus grow on medium lacking estradiol. In contrast, escapers that originated from recessive mutants in different genes will complement and will fail to grow on media lacking estradiol. In addition, crosses to the original SG strain will indicate whether the mutation is recessive or dominant. Table 8 summarizes the complementation analysis. 8 complementation groups for FAS2 SG escapers and 7 complementation groups for SEC4 SG escapers were isolated. For RPB11, complementation groups could not be determined because all escapers were dominant. One candidate from each complementation group was selected for further analysis.

Figure 22:
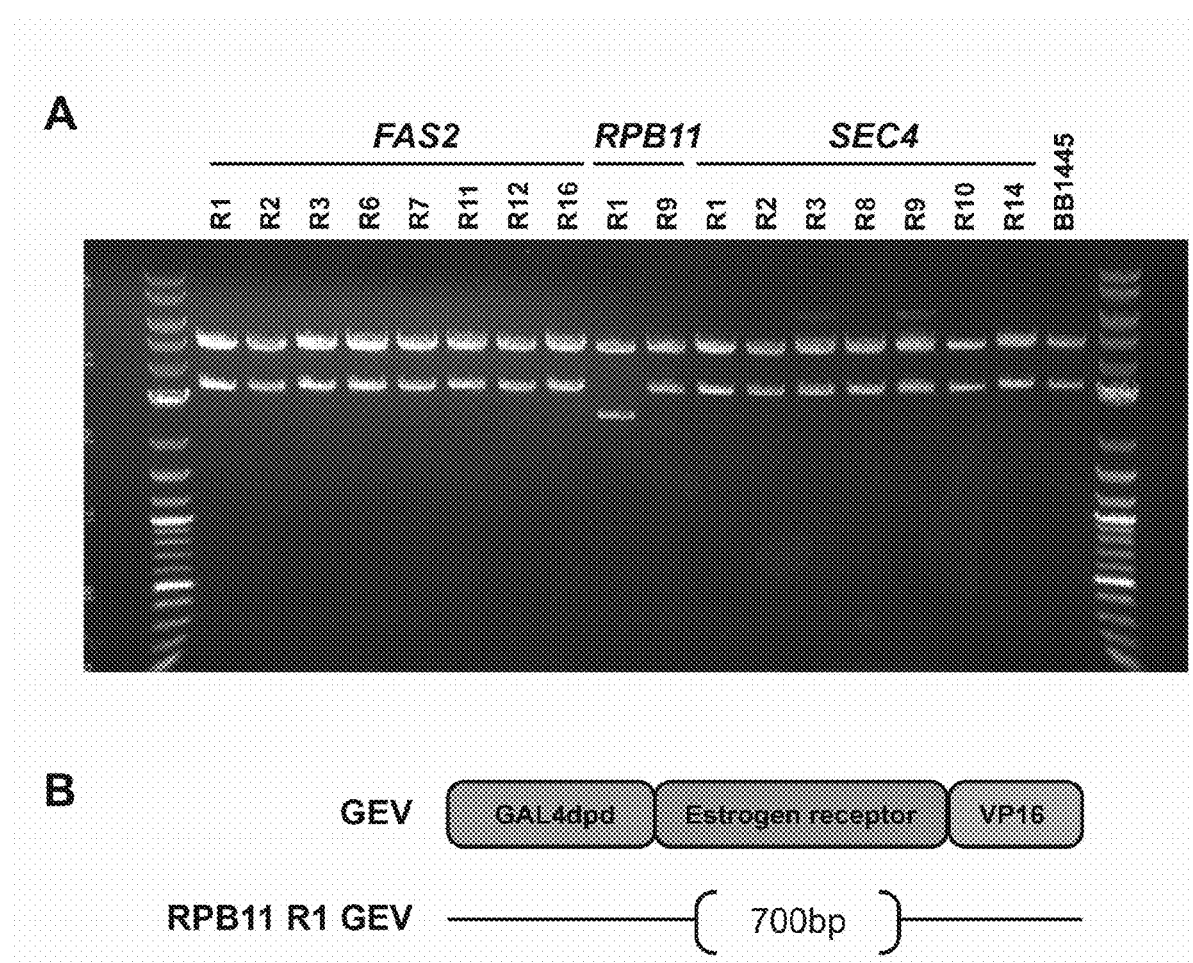
FIG. 22: SG Escapers plasmid analysis. (A) Plasmids were isolated from escapers strains and transformed into bacteria cells. Plasmid DNA was digested with BssHII to analyze any changes compare to wt plasmid (pGEV). Only RPB11 MATa R1 plasmid showed digest pattern different from wt plasmid. (B) Schematic representation of the GEV protein indicating the deletion found in RPB11 R1 strain.

In order to analyze the location (GEV plasmid or genome) of the mutation in each escaper, the plasmid from each escaper strain was isolated and transformed into bacteria for sequence analysis. Digestion of plasmid DNA revealed that all but one (RPB11 MATa R1) showed a similar plasmid digest pattern as the original plasmid (FIG. 22). Sequencing of the plasmid isolated from RPB11 MATa R1 showed a 684 bp deletion in the Estrogen Binding domain (EBD). Without intending to be bound by any particular theory, it is believed this explains both the growth in the absence of estradiol due to constitutive localization in the nucleus and well as the escaper's dominant phenotype. To locate the mutations in the remaining escapers the following was performed: (1) Cured each escaper of its plasmid; (2) transformed the isolated plasmids into the original corresponding safeguard strain; (3) transformed a WT plasmid (pRS416-GEV) to the cured escaper (step 1).

Figure 23:
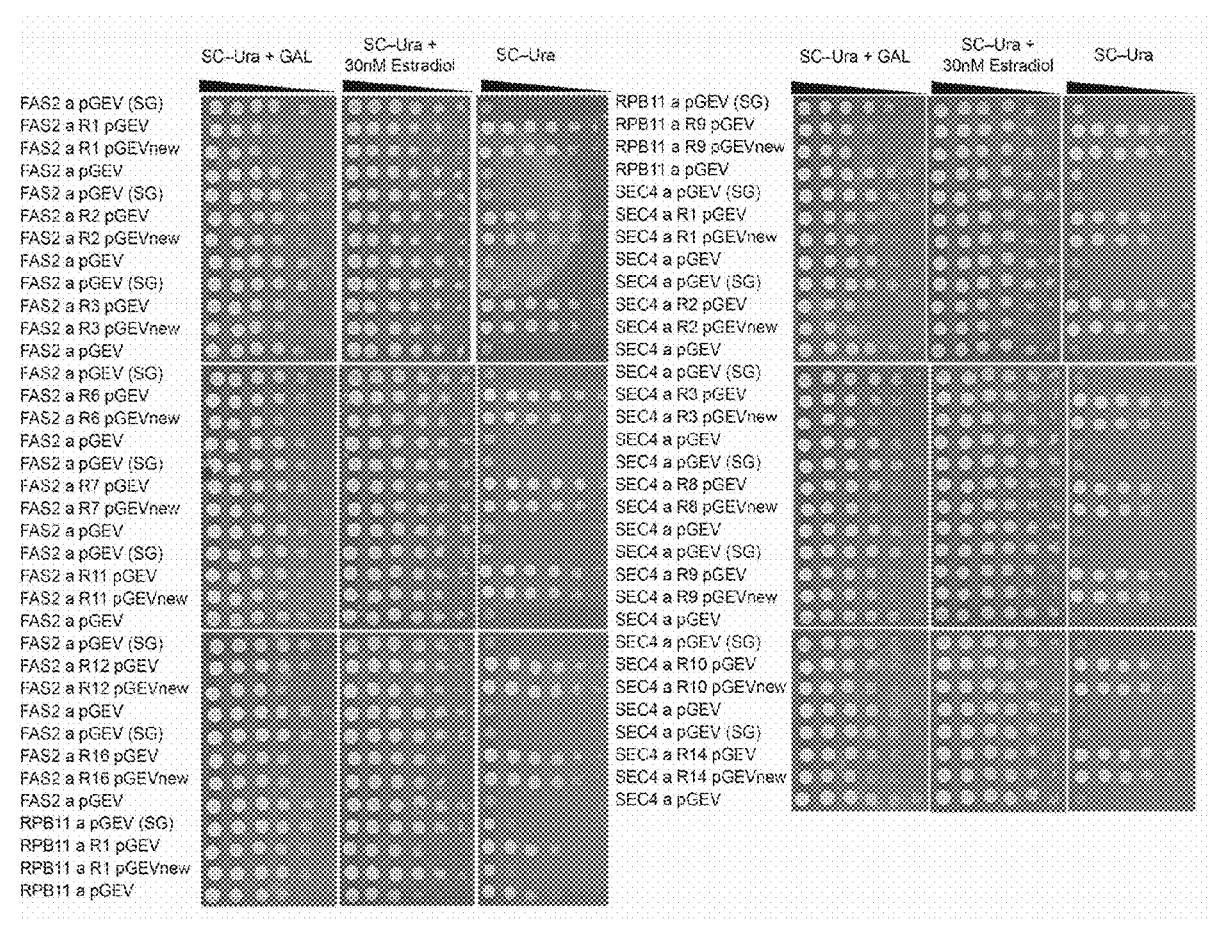

All of these were plated in serial dilution on SC-Ura supplemented with 2% Galactose, SC-Ura+30 nM Estradiol and SC-Ura (FIG. 23). In all but one strain (RPB11 MATa R1), the mutation is in the genome, as transforming the isolated plasmid from the escapers did not render the original SG strain the capability to grow in without estradiol, however, the cured strain transformed with the original WT plasmid (pGEVnew) did reconstitute the escaper phenotype.

Figure 24:
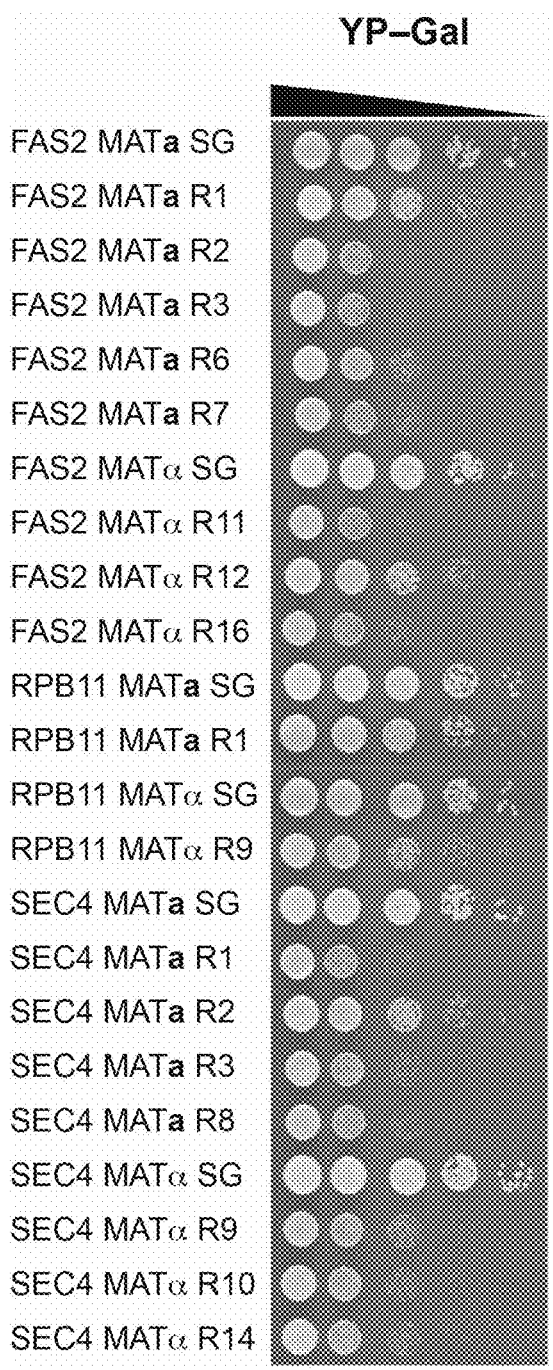
FIG. 24: Drop assay from plasmid-cured escapers. Escapers were cured of their GEV plasmid and plated as serial dilutions on YP-GAL. All escapers show significant slower growth compared to the original SG strain.

The escapers cured of the plasmid were analyzed on YP-GAL medium (FIG. 24). All escapers show significantly slower growth rate in YP-Gal compared to the original SG, which will give them a fitness disadvantage compared to the original SG strains. This was also observed (to a lesser extent) when escapers were plated on SC-Ura+30 nM Estradiol (FIG. 23), which will give them a fitness disadvantage compared to the original SG strains.

In order to locate the genomic mutations that caused the occurrence of these escapers genome sequencing of the escapers (one from each complementation group) was performed. This revealed mutations in four different components of the Rpd3L complex (Table 9). This complex represses transcription of URS1 containing genes by hypoacetylation of histone H3 and H4 (Keogh et al. (2005) Cell 123(4):593-605). Due to the fact that the SG constructs have a SPALX promoter (Vidal M, Bet al. (1996) Proceedings of the National Academy of Sciences of the United States of America 93(19):10315-10320) that contains the URS1 sequence (Sumrada R A & Cooper T G (1987) Proceedings of the National Academy of Sciences of the United States of America 84(12):3997-4001), mutations in genes encoding the components of the Rpd3L complex will alleviate the repression and cause expression of the SG gene even in the absence of estradiol. Since 100% of the mutations isolated as described herein in SEC4 and FAS2 SG strains are recessive, it is expected that the escape rate can be lowered substantially by use of diploid strains.

Figure 15:
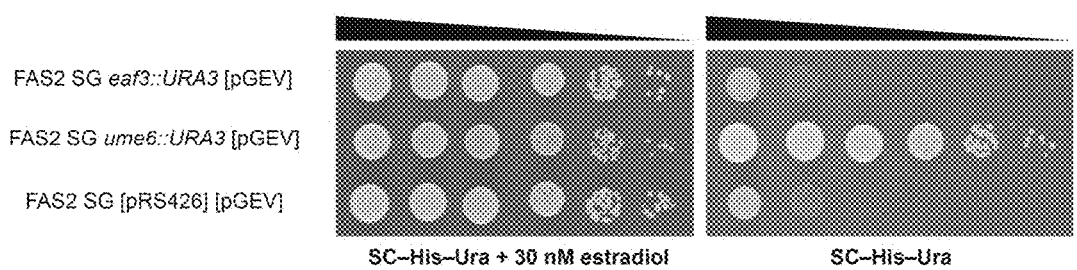
FIG. 15: Reconstitution of escaper phenotype. Genome sequencing revealed that all escapers carry a mutation in genes encoding subunits of the Rpd3L complex. In order to reconstitute the escaper phenotype in our SG strains we deleted ume6 in the FAS2 MATa SG strain. Serial dilution of FAS2 SG deleted for ume6, eaf3 and carrying a pRS416 plasmid were plated appropriate media with and without estradiol. Cell deleted for ume6 completely recapitulated the escapers phenotype.

To verify the effect that mutations in Rpd3L component genes has on our SG strain, UME6 was deleted in all FAS2 MATa SG strain. As a control a member of the Rpd3 S complex, EAF3 was deleted. As seen in FIG. 15, deletion of ume6 completely recapitulated the escaper phenotype, including a slight growth defect in medium with estradiol.

Example 15

This Example and other Examples herein provide a description of non-limiting improvements to SG strains. In a system known as the ZEV system the transcription factor (VP16) is fused to an Estrogen-Binding-Domain (EBD) and a Zinc-finger binding domain recognizing a 9 bp sequence was cloned into a minimal GAL1 promoter (McIsaac R S, et al. (2013) Nucleic acids research 41(4):e57). The ZEV system was shown to have no effect on growth rate in yeast cells. In the present disclosure the Z4 array was cloned into the SPAL promoter, replacing the GAL4 binding sites (FIG. 16A). This promoter is expected to be as tight as the SPAL promoter due to its URS1 sequence (transcribing only in the presence of estradiol and the Z4EV transducer) and as specific as the Z4EV system (no off-target effect). This novel chimeric promoter is referred to herein from time to time as the "SPAZ4" promoter. Following the synthesis of the SPAZ4 promoter the yGG approach was used to clone it with the 3 best acting SGs genes (FAS2, RPB11 and SEC4). Serial dilutions on media with or without 1 μM estradiol have shown that in all three cases growth with estradiol is indistinguishable from that of the shuffle strain. There was a significant reduction in viability (death) on plates without estradiol (FIG. 16B). In addition, growth rate analysis has shown that in YPD medium supplemented with 30 nM estradiol all three SPAZ4 SG strains show growth similar to the BY4741 wild-type strain (FIG. 16C). Metabolomics analyses showed no significant change in any of the metabolites examined compared to a WT strain.

Example 16

Figure 17:
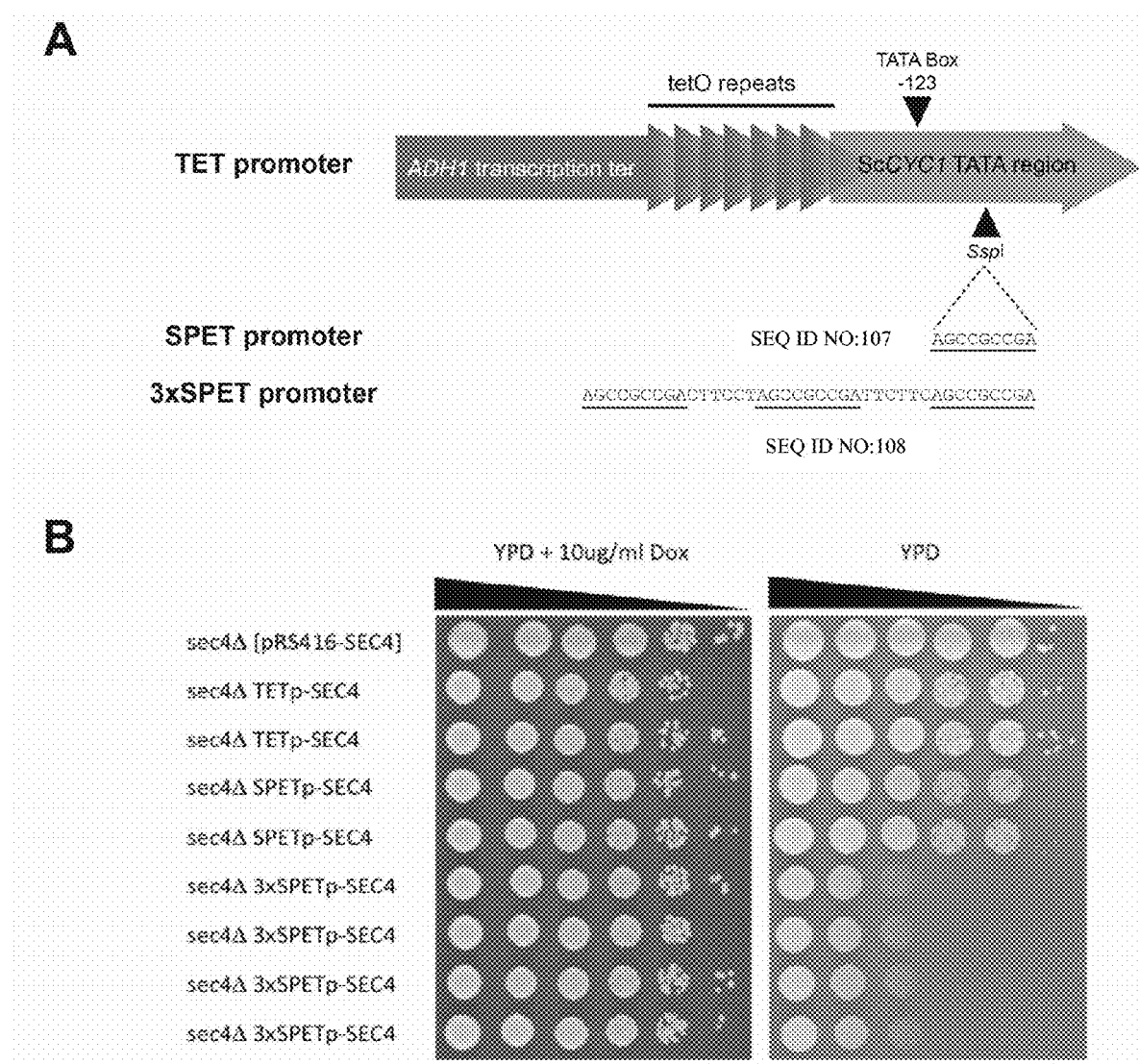
FIG. 17: (A) Schematic representation of the TET, SPET and 3xSPET with ADH1 transcription terminator sequence (purple box), the tetO repeats (blue triangles) and CYC1 TATA region (green arrow), arrow heads indicate TATA box location and SspI restriction site. For the SPET promoter a single URS1 sequence was cloned into the SspI site. for 3xSPET three repeats of the URS1 sequence (with linkers) were cloned to the SspI site. (B) The TET (2 isolates), SPET (2 isolates) and 3xSPAT (4 isolates) promoters used to drive the SEC4 gene. Serial dilutions of all strains compared to the shuffle strain were plated on YPD media with or without 10 mg/ml Doxycycline. The SPET promoter sequence AGCCGCCGA is SEQ ID NO:107. The 3xSPET promoter sequence AGCCGCCGACTTCCTAGCCGCCGAT-TCTTCAGCCGCCGA is SEQ ID NO:108.

This example provides a description of one approach to engineering a yeast TET promoter. In addition to the GALx promoters and their derivatives, other known switches are based on the TET system, which has been used in yeast (Gari E, Pet al. (1997) Yeast 13(9):837-848) as well as in other organisms. In the present disclosure it was an objective to construct a TET-based SG strain. In one approach a TET system was too leaky and thus showed no significant reduction in growth without Doxycycline for all of 44 essential genes SG. Therefore, based on success with the SPAL and SPAZ promoters, a promoter referred to herein as the "SPET" promoter was constructed. This promoter is based on an embodiment of a TET promoter (FIG. 17A) with a URS1 sequence inserted downstream of the TATA box and upstream of the estimated transcription start site (FIG. 17A). To produce this, first, a single URS1 (SPET) or 3 repeats of the URS1 sequence (3×SPAT) was cloned into the TET promoter. These promoters were then cloned into an acceptor vector for safeguard gene integration. For examining the function of the SPET promoter we cloned one of our candidate essential genes, SEC4, under the control of the TET, SPET or 3×SPET promoters and analyzed the expression with or without Doxycycline (FIG. 17B), compared to a strain carrying a WT copy of SEC4. The 3×SPET promoter showed almost 4-fold reduction in growth without doxycycline (YPD) compared to both the SPET and the TET promoters. However, although very slight, all three SPET promoters show a growth defect compared to WT expression of the SG gene. Thus, it is demonstrated herein that a modified TET promoter could also serve as a SG switch.

Example 17

This Example provides a description of analysis of a library of representative decoy compounds.

In certain embodiments, an aspect of using a safeguard strain to guard proprietary elements is having the ability to prevent outside sources from propagating the strains without previous knowledge of the specific medium requirements of a given SG strain. In addition to enabling growth in very low concentrations of the required compound the identity of that compound could be masked using an array of different but inert decoy compounds, as discussed above in Examples 1-9. An aspect of such decoy molecules is that they should not by themselves have any deleterious effect on the growth of the yeast strain. This should also be true of ligands used to activate the SG. To this end, the transcriptome of yeast cells (BY4741) in the presence of 22 compounds (Table 10) was analyzed, at two concentrations each. They were separated into three groups depending on their solvent (Water, DMSO or Ethanol) and the metabolomes were compared to a solvent control.

Figure 25:
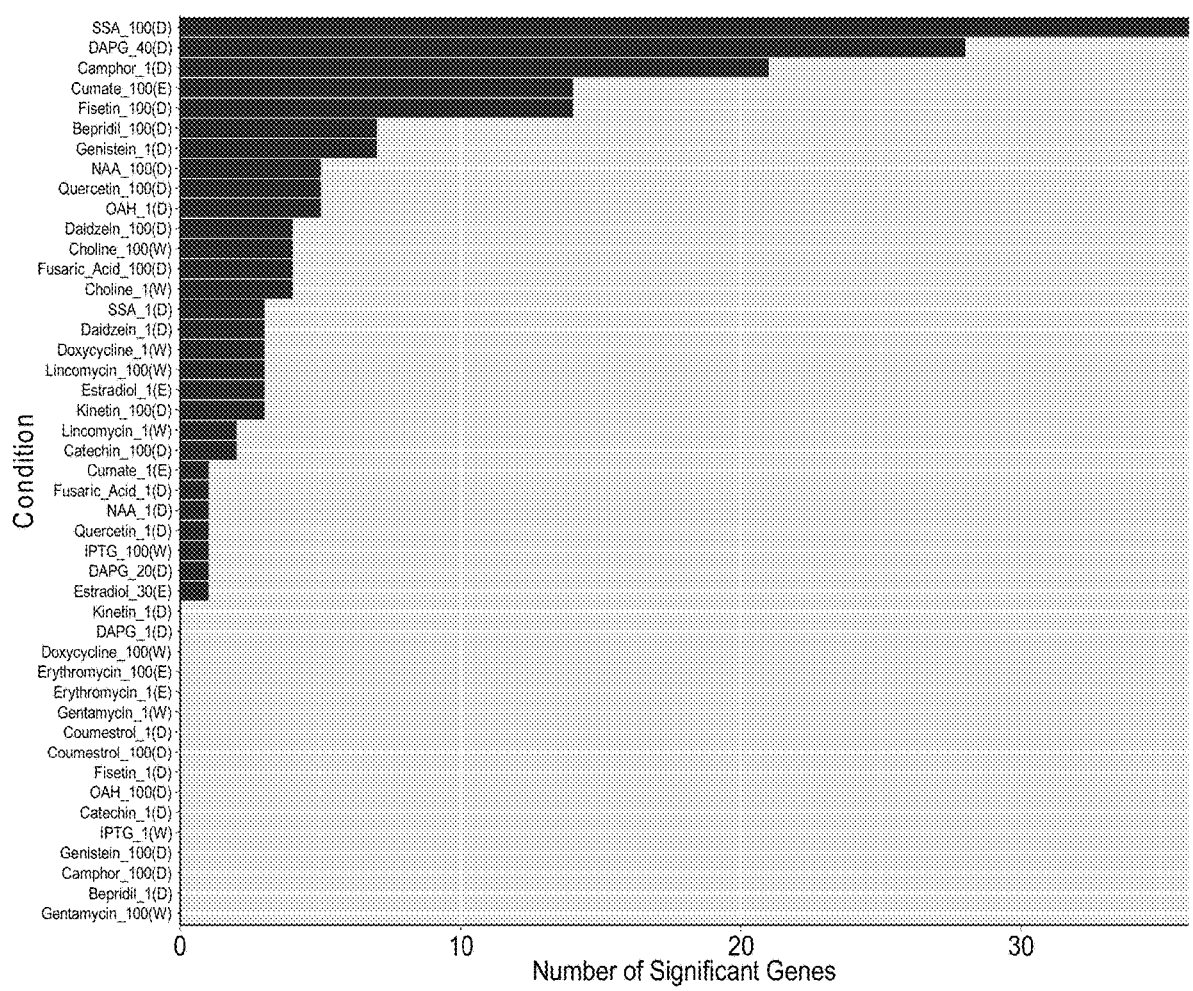
FIG. 25: Decoy molecules' effect on transcription. Graphic representation of the number of transcripts/genes changed in response to each specific candidate decoy compound and concentration. BY4741 WT cells were grown in liquid culture in the presence of each candidate decoy molecule and subjected to transcriptome analysis.

Analysis of the transcriptome of cells exposed to the compounds revealed that in many cases there is a strong effect on transcription (FIG. 25). However, several compounds produce only minor changes (1-3 genes) or even no change at all (FIG. 25). The latter group are the best candidates as ligands for future gene regulatory systems for Safeguards.

It will be recognized from the foregoing that the present disclosure describes a process of screening a library of 250 essential genes selecting what are believed to be the three best acting genes (FAS2, RPB11 and SEC4) under estradiol induction. In the present screen what is believed to be the best acting promoter for each gene was selected out of 6 possible candidates. Constructs that showed what is believed to be the lowest possible escape rate with the least measurable effect on growth were compared to a control strain. This analysis facilitated achieving an escape rate of $10^{-8}$ with only a single essential gene; compared to $10^{-6}$ demonstrated in Examples 1-9 for a single gene; and closer to $10^{-9}$ that was observed for two histone genes.

Figure 16:
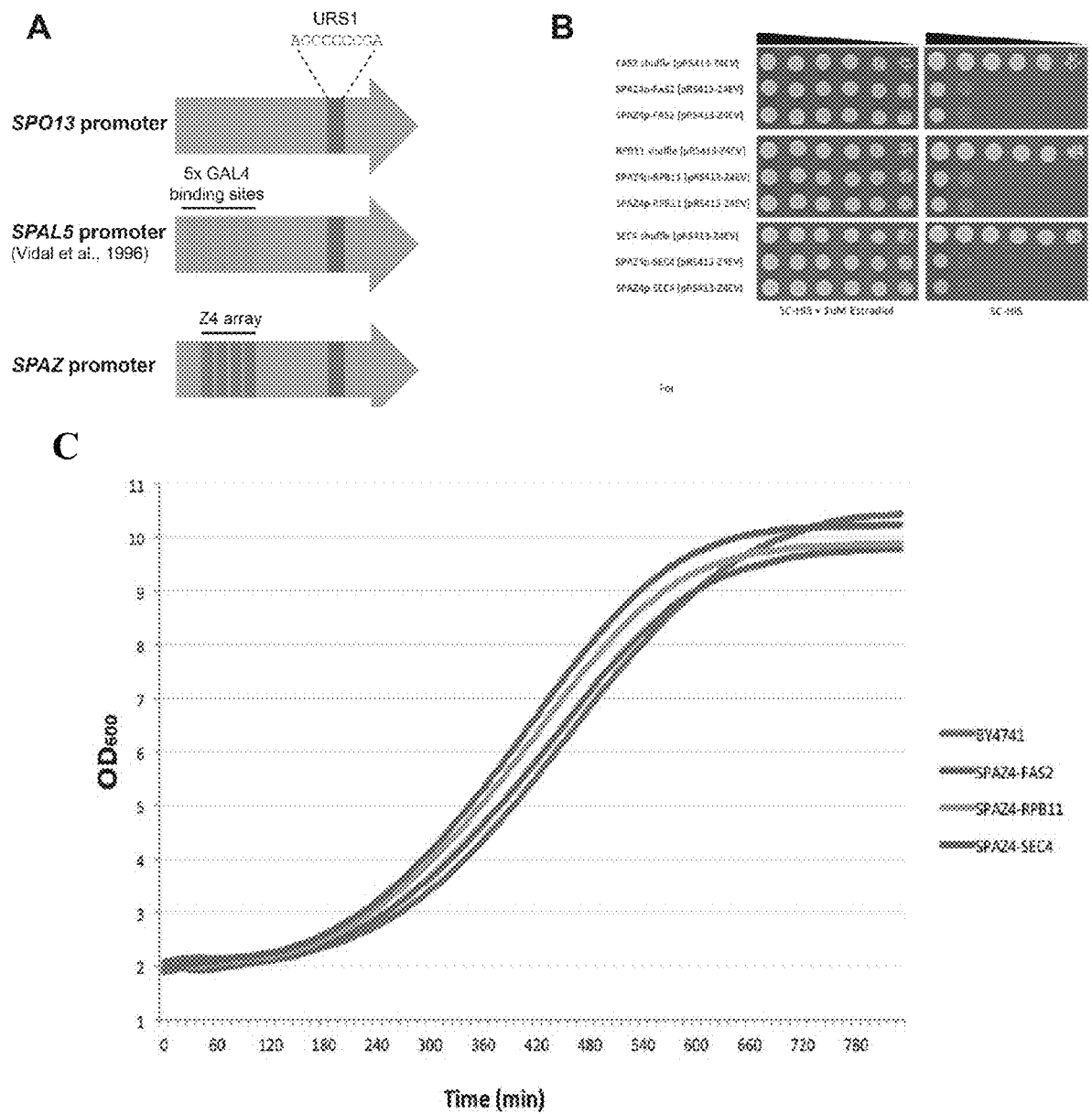
FIG. 16: The SPAZ4 promoter. (A) Schematic representation of the SPO13 promoter with URS1 sequence (purple box), the SPAL5 promoter with 5 GAL4 binding sites (turquoise boxes) and the SPAZ4 promoter with the 4 repeats of the Z4 array binding site (orange boxes). (B) The SPAZ promoter used to drive our 3 top safeguard genes: FAS2, RPB11 and SEC4. Serial dilutions of all strains compared to their shuffle strains containing the ZEV expressing plasmid were plated on YPD media with or without 1 μM estradiol. (C) Growth of all three SPAZ safeguard strains was measured compared to BY4741 wild type strain in YPD medium containing 30 nM estradiol. (D) Metabolomics analysis presented as a hit-map of the fold change from each metabolite analyzed. Safeguard strains: NAy484 (FAS2), NAy486 (RPB11) and NAy488 (SEC4), control—NAy497.

It is also demonstrated herein that using promoter engineering can decrease the genome wide effect of the GAL promoter using a synthetically designed zinc-finger while improving promoter leakiness using a natural URS sequence (FIG. 16). In addition, a similar strategy to engineer the TET promoter, decreasing leakiness under restrictive conditions by inserting multiple URS sequences, is also shown.

Thus it is demonstrated herein that two systems (ZEV and TET) when combined may decrease escape rate to below detectable levels.

Example 18

This Example provides a description of the material and methods used to obtain the results discussed in Examples 10-17.

Strains, plasmids, oligonucleotides and mediaYeast strains and the plasmids contained are listed in Table 11. Oligonucleotides used to amplify essential genes for shuffle plasmid construction are listed in Table 12. Media used were as follows. Yeast strains were cultured in YPD medium or SD-based medium supplemented with appropriate amino acids; fully supplemented medium containing all amino acids plus uracil and adenine is referred to as SC. ☐Estradiol was purchased from Sigma-Aldrich (St. Louis, Mo.), and 5-fluoroorotic acid (5-FOA) was from US Biological (Massachusetts, Mass.). Doxycycline (Dox) was obtained from Clontech laboratories (Mountain View, Calif.). *Escherichia coli* was grown in Luria Broth (LB) media. To select strains with drug-resistant genes, carbenicillin (Sigma-Aldrich) or kanamycin (Sigma-Aldrich) were added at final concentrations of 75 µg/ml and 50 µg/ml respectively. Agar was added to 2% for preparing solid media. Final concentrations of compounds and their solvents are listed in Table 10, 1000× stock solution was prepared for all compounds.

Plasmid Recovery from Yeast

Plasmid recovery from yeast was carried out using a Zymoprep yeast plasmid miniprep kit (Zymo Research, Irvine, Calif.) following the manufacturer's instructions.

Safeguard Promoter Identification

For each strain, genomic DNA was extracted and the promoter region was amplified using the vector forward primer and a reverse primer 100 bp downstream of the ATG. Each PCR fragment was sent for sequencing using the same primers. The results of the sequencing are summarized in Table 6.

Escape Rate Measurement

Escape rates were calculated using the method of the median (Lea D E & Coulson C A (1949) Journal of genetics 49(3):264-285). For measurement rates in the $10^{-5}$ to $10^{-9}$ range, 5-12 independent cultures (each grown from a single parent colony) were inoculated into 20 mL of media supplemented with 30 nM estradiol in liquid cultures. In total, $10^8$ and $10^{-7}$ cells were plated on restrictive medium. Viable titer was determined by plating 100 µL of a five to six serial 10-fold dilution on permissive medium. The reversion frequency was obtained by dividing colony-forming units on restrictive plates by colony-forming units on permissive plates. The median reversion frequency was then used to calculate the rate using the method of the median.

For each SG strain to be measured, 8 "escaper" escaper colonies were picked from independently grown cultures and grown up in 10 mL of permissive liquid culture (with plasmid selection if applicable), for 48 h at 30° C. Tenfold serial dilutions were plated on restrictive and permissive agar plates, and incubated at 30° C. for 2-3 d until single colonies appeared. One colony was chosen per culture to assure independence.

RNASeq

A single colony was picked and grown up in 10 mL of permissive liquid medium, and incubated at 30° C. until the A600 was between 0.8 and 1.2, and RNA was isolated as described using a Qiagen RNAEasy kit using the manufacturer's protocol. We performed RNASeq of strains integrating the histone, RPC11, SUI1, and HSP10 safeguards. mRNA was sequenced using an Illumina HiSeq and standard TruSeq preparation kits. For each strain, we obtained ~12 million 50-bp single-end reads. Reads were mapped using TOPHAT (Kim D, et al. (2013) Genome biology 14(4): R36)) to the reference *S. cerevisiae* genome (S288c). Approximately 95% of the reads were mapped. For each gene, read counts were computed using HTSEQ (Anders S, et al. (2015) Bioinformatics 31(2):166-169) and analyzed for differential expression using DESEQ (Anders S & Huber W (2010) Genome biology 11(10):R106), with standard parameters and following the no-replicates scenario. For each gene, a raw P value was obtained and an adjusted P value using the standard Benjamini-Hochberg procedure (Benjamini Y & Hochberg Y (1995) J R Stat Soc B (57 (1)):289-300). A 1% false-discovery rate (adjusted P value≤0.01) to identify genes that are significantly differentially expressed was used.

Creating Parts for Combinatorial Yeast Golden-Gate (yGG)

In addition to the 47 strains chosen from the TET-off library three additional genes (HSP10, RPC11 and SUI1) were added based on Examples 1-9 where they were shown to function as safeguard genes. All 50 genes were to be potentially cloned downstream of 7 different promoters: GAL1, GAL10, GAL7, SPAL2, SPAL10, SPAL7. They were assembled with the GAL1 terminator and into an acceptor vectors with integration cassettes. All combinations were examined for their ability to serve as potential safeguards. All 50 genes, 6 promoters and terminator were amplified with the appropriate overhangs for yGG from the yeast genome Agmon N, et al. (2015) *ACS synthetic biology*), cloned into a pCR-Blunt II-TOPO vector (Invitrogen) and sequence verified. Most genes were amplified as one part genes, however, some were either too large to amplify as one part or had an internal BsaI site, which is incompatible with yGG assembly and thus were amplified as multiple gene parts compatible with yGG assembly. All but one gene, PSA1, failed at this step, the successful 49 genes were further analyzed. In total 67 gene parts, 6 promoter parts and one terminator part were synthesized for the yGG assembly. As an acceptor vector pAV10.HO5.loxP, an integrating vector was selected, with the LEU2 marker for integration into the HO locus.

DNAseq

Pair-end whole genome sequencing of escapers was performed using an IlluminaHiSeq using TruSeq preparations kits. Totally 20 samples were sequenced with 19.5M-33.5M paired reads generated per sample. The length of read is 101 base pairs. Quality control was performed using software FastQC version 0.11.2 All the reads in FASTQ format were aligned to Yeast reference genome constructed starting with the sequence for control strains (*S. cerevisiae* strain BY4741 genome sequence and *S. cerevisiae* strain BY4742 genome sequence) using BWA version 0.7.8 with -P-M-R parameter settings. Approximately 86%-93% reads were aligned to the corresponding reference genome. Software SAMtools version 0.1.19 was used to call variants with mpileup -A -uf and bcftools view -bvcg parameter settings. The results were subjected to a set of post-processing filters requiring (i) a minimum of 10× coverage per variant site; (ii) wild-type reads in <10% of the total reads per site; (iii) Reads supporting the variant of the control sample in <5%.

The following Tables are pertinent to those discussed above.

TABLE 1

Yeast Strains

| Strain | MAT | Parent | Plasmid | Genotype | Plasmid Type | Marker |
|---|---|---|---|---|---|---|
| PCy068 | a | BY385 | pRS415 | his3Δ200 leu2Δ1 lys2Δ202 trp1Δ63 ura3-52 | pRS415 | LEU2 |
| PCy163 | a | JDY6 | pDM9 | his3Δ200 leu2Δ1 lys2Δ202 trp1Δ63 ura3-52 hht1-hhf1Δ::natMX4 hht2-hhf2Δ::hygMX4 | HHT1 HHF1 URA3 CEN | URA3 |
| PCy230 | a | PCy163 | pPC012 | his3Δ200 leu2Δ1 lys2Δ202 trp1Δ63 ura3-52 hht1-hhf1Δ::natMX4 hht2-hhf2Δ::hygMX4 | loxP-HHTS-loxP HHFS loxP LEU2 CEN | LEU2 |
| PCy251 | a | PCy230 | PCy012; SCW11-CreEBD | his3Δ200 leu2Δ1 lys2Δ202 trp1Δ63 ura3-52 hht1-hhf1Δ::natMX4 hht2-hhf2Δ::hygMX4 | pGal1-HHT SpGal7-HHFS CEN LEU2 | LEU2; HIS3 |
| PCy426 | a | MM diploid collection RPC11Δ | | ura3Δ0, leu2Δ0, his3Δ1, can1D:: LEU2+-MFA1pr-His3, RPC11::KanMX HO::pGAL1_RPC11_Gal1 3'UTR-URA3 | | URA3 |
| PCy437 | a | MM diploid collection SUI1Δ | | ura3Δ0, leu2Δ0, his3Δ1, can1D:: LEU2+-MFA1pr-His3, SUI1::KanMX HO::pGAL1_SUI1_Gal1 3'UTR-URA3 | | URA3 |
| PCy448 | a | MM diploid collection HSP10Δ | | ura3Δ0, leu2Δ0, his3Δ1, can1D::LEU2+-MFA1pr-His3, HSP10::KanMX HO::pGal1_HSP10_Gal1 3'UTR-URA3 | | URA3 |
| PCy599 | a | PCy230 | | his3Δ200 leu2Δ1 lys2Δ202 trp1Δ63 ura3-52 hht1-hhf1Δ:: natMX4 hht2-hhf2Δ:: hygMX4 HO::loxPWT-HHTS-loxPWT-HHFS-loxPWT-URA3 | | URA3 |
| PCy636 | a | PCy599 | Tdh3-CreEBD-HIS3 | his3Δ200 leu2Δ1 lys2Δ202 trp1Δ63 ura3-52 hht1-hhf1Δ:: natMX4 hht2-hhf2Δ:: hygMX4 HO::loxPWT-HHTS-loxPWT-HHFS-loxPWT-URA3 | Tdh3-CreEBD-HIS3 | PCy636 |
| NAy236 | a | PCy599 | pGal4-ER-VP16-HIS3 | his3Δ200 leu2Δ1 lys2Δ202 trp1Δ63 ura3-52 hht1-hhf1Δ:: natMX4 hht2-hhf2Δ:: hygMX4 HO::loxPWT-HHTS-loxPWT-HHFS-loxPWT-URA3 | pGal4-ER-VP16-HIS3 | HIS3 |
| NAy460 | a | Yeast Het-dip deletion collection | pRS416-RPC11 | leu2Δ0 met15Δ0 ura3Δ0 his3Δ1 RPC11::KanMX | pRS416-RPC11 | URA3 |
| | | | | | | URA3 HIS3 |
| AZy0010 | a | RPC11 shuffle strain | Tdh3-CreEBD-HIS3 | leu2Δ0 met15Δ0 ura3Δ0 his3Δ1 RPC11::KanMX HO::GAL1p-RPC11-GAL1t::LEU2 | Tdh3-CreEBD-HIS3 | LEU2 HIS3 |
| AZy0011 | a | RPC11 shuffle strain | pGal4-ER-VP16-HIS3 | leu2Δ0 met15Δ0 ura3Δ0 his3Δ1 RPC11::KanMX HO::GAL1p-RPC11-GAL1t::LEU2 | pGal4-ER-VP16-HIS3 | LEU2 HIS3 |
| AZy0012 | a | RPC11 shuffle strain | pRS413 | leu2Δ0 met15Δ0 ura3Δ0 his3Δ1 RPC11::KanMX HO::GAL1p-RPC11-GAL1t::LEU2 | pRS413 | LEU2 HIS3 |
| AZy0013 | a | RPC11 shuffle strain | Tdh3-CreEBD-HIS3 | leu2Δ0 met15Δ0 ura3Δ0 his3Δ1 RPC11::KanMX HO::GAL7p-RPC11-GAL1t::LEU2 | Tdh3-CreEBD-HIS3 | LEU2 HIS3 |
| AZy0014 | a | RPC11 shuffle strain | pGal4-ER-VP16-HIS3 | leu2Δ0 met15Δ0 ura3Δ0 his3Δ1 RPC11::KanMX HO::GAL7p-RPC11-GAL1t::LEU2 | pGal4-ER-VP16-HIS3 | LEU2 HIS3 |
| AZy0015 | a | RPC11 shuffle strain | pRS413 | leu2Δ0 met15Δ0 ura3Δ0 his3Δ1 RPC11::KanMX HO::GAL7p-RPC11-GAL1t::LEU2 | pRS413 | LEU2 HIS3 |
| AZy0016 | a | RPC11 shuffle strain | Tdh3-CreEBD-HIS3 | leu2Δ0 met15Δ0 ura3Δ0 his3Δ1 RPC11::KanMX HO::GAL10p-RPC11-GAL1t::LEU2 | Tdh3-CreEBD-HIS3 | LEU2 HIS3 |
| AZy0017 | a | RPC11 shuffle strain | pGal4-ER-VP16-HIS3 | leu2Δ0 met15Δ0 ura3Δ0 his3Δ1 RPC11::KanMX HO::GAL10p-RPC11-GAL1t::LEU2 | pGal4-ER-VP16-HIS3 | LEU2 HIS3 |
| AZy0018 | a | RPC11 shuffle strain | pRS413 | leu2Δ0 met15Δ0 ura3Δ0 his3Δ1 RPC11::KanMX HO::GAL10p-RPC11-GAL1t::LEU2 | pRS413 | LEU2 HIS3 |
| AZy0019 | a | RPC11 shuffle strain | Tdh3-CreEBD-HIS3 | leu2Δ0 met15Δ0 ura3Δ0 his3Δ1 RPC11::KanMX HO::SPAL2p-RPC11-GAL1t::LEU2 | Tdh3-CreEBD-HIS3 | LEU2 HIS3 |
| NAy390 | a | RPC11 shuffle strain | pGal4-ER-VP16-HIS3 | leu2Δ0 met15Δ0 ura3Δ0 his3Δ1 RPC11::KanMX HO::SPAL2p-RPC11-GAL1t::LEU2 | pGal4-ER-VP16-HIS3 | LEU2 HIS3 |

TABLE 1-continued

Yeast Strains

| Strain | MAT | Parent | Plasmid | Genotype | Plasmid Type | Marker |
|---|---|---|---|---|---|---|
| AZy0021 | a | RPC11 shuffle strain | pRS413 | leu2Δ0 met15Δ0 ura3Δ0 his3Δ1 RPC11::KanMX HO::SPAL2p-RPC11-GAL1t::LEU2 | pRS413 | LEU2 HIS3 |
| AZy0022 | a | RPC11 shuffle strain | Tdh3-CreEBD-HIS3 | leu2Δ0 met15Δ0 ura3Δ0 his3Δ1 RPC11::KanMX HO::SPAL5p-RPC11-GAL1t::LEU2 | Tdh3-CreEBD-HIS3 | LEU2 HIS3 |
| NAy391 | a | RPC11 shuffle strain | pGal4-ER-VP16-HIS3 | leu2Δ0 met15Δ0 ura3Δ0 his3Δ1 RPC11::KanMX HO::SPAL5p-RPC11-GAL1t::LEU2 | pGal4-ER-VP16-HIS3 | LEU2 HIS3 |
| AZy0024 | a | RPC11 shuffle strain | pRS413 | leu2Δ0 met15Δ0 ura3Δ0 his3Δ1 RPC11::KanMX HO::SPAL5p-RPC11-GAL1t::LEU2 | pRS413 | LEU2 HIS3 |
| AZy0025 | a | RPC11 shuffle strain | Tdh3-CreEBD-HIS3 | leu2Δ0 met15Δ0 ura3Δ0 his3Δ1 RPC11::KanMX HO::SPAL6p-RPC11-GAL1t::LEU2 | Tdh3-CreEBD-HIS3 | LEU2 HIS3 |
| NAy392 | a | RPC11 shuffle strain | pGal4-ER-VP16-HIS3 | leu2Δ0 met15Δ0 ura3Δ0 his3Δ1 RPC11::KanMX HO::SPAL6p-RPC11-GAL1t::LEU2 | pGal4-ER-VP16-HIS3 | LEU2 HIS3 |
| AZy0027 | a | RPC11 shuffle strain | pRS413 | leu2Δ0 met15Δ0 ura3Δ0 his3Δ1 RPC11::KanMX HO::SPAL6p-RPC11-GAL1t::LEU2 | pRS413 | LEU2 HIS3 |

TABLE 2

Primers used Examples 1-9.

| Name | Sequence | Purpose |
|---|---|---|
| M13F | GTAAAACGACGGCCAG (SEQ ID NO: 1) | GEV sequencing |
| M13R | CAGGAAACAGCTATGAC (SEQ ID NO: 2) | GEV sequencing |
| PC_oligo379 | GAAGGTTAATGTGGCTGTGGTTTCAGGGTCCATAAAGCTTGTCCTGGAAGTCTCATGGAG (SEQ ID NO: 3) | SPALX PCR |
| PC_oligo380 | TCAGGATCCCTAGGTTCCTTTGTTACTTCTTCCG (SEQ ID NO: 4) | SPALX PCR |
| PC_oligo401 | ggtctcacagtGAAGGTTAATGTGGCTGTGGTTTCA (SEQ ID NO: 5) | SPALX PCR |
| PC_oligo324 | ggtctcacattATTATTCTCGACTCAACT (SEQ ID NO: 6) | SPALX PCR |
| GEVF2 | GTACAGATGCTCCATGCCTT (SEQ ID NO: 7) | GEV sequencing |
| GEVR2 | AAGAATGAGCCAAGACTTGC (SEQ ID NO: 8) | GEV sequencing |
| GEVF3 | GGATCATACTCGGAATAGAGT (SEQ ID NO: 9) | GEV sequencing |
| GEVR3 | CGAACTAATACTGTAGCCCT (SEQ ID NO: 10) | GEV sequencing |

TABLE 3

Differentially expressed genes in safeguard switches

| Safe-guard | Pro-moter | Gene | Log2Fold Change | P-value | Adjusted P-value |
|---|---|---|---|---|---|
| RPC11 | GAL1 | LYS2 | Inf | $1.424 \cdot 10^{-08}$ | $9.573 \cdot 10^{-05}$ |
| | | RPC1 | 6.660 | $9.017 \cdot 10^{-08}$ | $3.031 \cdot 10^{-04}$ |
| | | YNL194C | 6.004 | $6.146 \cdot 10^{-07}$ | 0.001 |
| | | YNL195C | 5.712 | $1.924 \cdot 10^{-06}$ | 0.003 |

TABLE 3-continued

Differentially expressed genes in safeguard switches

| Safeguard | Promoter | Gene | Log2Fold Change | P-value | Adjusted P-value |
|---|---|---|---|---|---|
| | GAL7 | — | — | — | — |
| | GAL10 | — | — | — | — |
| SUI1 | GAL1 | MET17 | -8.725 | $4.184 \cdot 10^{-16}$ | $2.786 \cdot 10^{-12}$ |
| | | BTN2 | -2.792 | $5.591 \cdot 10^{-13}$ | $1.861 \cdot 10^{-09}$ |
| | | ZPR1 | -2.148 | $8.326 \cdot 10^{-09}$ | $1.848 \cdot 10^{-05}$ |
| | | HO | 2.027 | $1.909 \cdot 10^{-08}$ | $3.177 \cdot 10^{-05}$ |
| | | YPR117W | 1.818 | $6.437 \cdot 10^{-07}$ | $8.572 \cdot 10^{-04}$ |
| | | IRA1 | 1.646 | $1.107 \cdot 10^{-06}$ | 0.001 |
| | | GCN1 | 1.795 | $1.350 \cdot 10^{-06}$ | 0.001 |
| | | TRA1 | 1.549 | $2.632 \cdot 10^{-06}$ | 0.002 |
| | GAL7 | MET17 | -Inf | $1.812 \cdot 10^{-12}$ | $1.202 \cdot 10^{-08}$ |
| | | MUP1 | 2.946 | $3.404 \cdot 10^{-09}$ | $1.129 \cdot 10^{-05}$ |
| | | YLR307C-A | -2.859 | $1.112 \cdot 10^{-06}$ | 0.002 |
| | | SAM1 | 2.371 | $3.818 \cdot 10^{-06}$ | 0.006 |
| | GAL10 | URA3 | 3.305 | $1.888 \cdot 10^{-14}$ | $1.252 \cdot 10^{-10}$ |

TABLE 3-continued

Differentially expressed genes in safeguard switches

| Safeguard | Promoter | Gene | Log2Fold Change | P-value | Adjusted P-value |
|---|---|---|---|---|---|
| | GAL7 | LYS2 | -10.438 | $1.085 \cdot 10^{-46}$ | $7.199 \cdot 10^{-43}$ |
| | | MET17 | -Inf | $1.098 \cdot 10^{-20}$ | $3.644 \cdot 10^{-17}$ |
| | | ICY2 | -3.025 | $3.510 \cdot 10^{-15}$ | $3.510 \cdot 10^{-15}$ |
| | | SNR6 | -3.879 | $2.320 \cdot 10^{-11}$ | $3.850 \cdot 10^{-08}$ |
| | | BTN2 | -2.124 | $2.334 \cdot 10^{-10}$ | $3.098 \cdot 10^{-07}$ |
| | | PDR5 | -1.795 | $4.080 \cdot 10^{-08}$ | $4.513 \cdot 10^{-05}$ |
| | | ZPR1 | -1.772 | $8.424 \cdot 10^{-08}$ | $7.988 \cdot 10^{-05}$ |
| | | HO | 2.265 | $1.430 \cdot 10^{-07}$ | $1.187 \cdot 10^{-04}$ |
| | | HSP42 | -1.684 | $2.392 \cdot 10^{-07}$ | $1.764 \cdot 10^{-04}$ |
| | GAL10 | LYS2 | -Inf | $5.175 \cdot 10^{-78}$ | $3.433 \cdot 10^{-74}$ |
| | | URA3 | 3.270 | $1.030 \cdot 10^{-50}$ | $1.030 \cdot 10^{-50}$ |
| | | HO | 3.576 | $1.568 \cdot 10^{-41}$ | $3.469 \cdot 10^{-38}$ |
| | | SNR6 | -3.849 | $7.327 \cdot 10^{-14}$ | $1.215 \cdot 10^{10}$ |
| | | HSP10 | 1.425 | $5.730 \cdot 10^{-13}$ | $7.604 \cdot 10^{-10}$ |
| | | COS8 | 2.246 | $3.920 \cdot 10^{-06}$ | 0.004 |
| | | KRI1 | -0.747 | $8.536 \cdot 10^{-06}$ | 0.008 |

TABLE 4

Escape frequencies of safeguard strains

| Strain name | Genotype | Reversion rate (n)* |
|---|---|---|
| PCy426 | ura3Δ0, leu2Δ0, his3Δ1, can1D:Leu2+-MFA1pr-His3, RPC11::KanMX HO::PGal1_RPC11_Gal1 3'UTR | 2.49E-07 (5) |
| PCy437 | ura3Δ0, leu2Δ0, his3Δ1, can1D:Leu2+-MFA1pr-His3, SUI1::KanMX HO:pGal1_SUI1_Gal1 3'UTR | 2.00E-06 (5) |
| PCy448 | ura3Δ0, leu2Δ0, his3Δ1, can1D::Leu2+-MFA1pr-His3, HSP10::KanMX HO:pGal1_HSP10_Gal1 3'UTR | 1.33E-05 (5) |
| PCy599 | his3Δ200 leu2Δ1 lys2Δ202 trp1Δ63 ura3-52 hht1-hhf1Δ:: natMX4 hht2-hhf2Δ:: hygMX4 HO::loxPWT-HHTS-loxPWT-HHFS-lopWT-URA3 | <1.16E-07 (5) |
| PCy230 | his3Δ200 leu2Δ1 lys2Δ202 trp1Δ63 ura3-52 hht1-hhf1Δ:: natMX4 hht2-hhf2Δ:: hygMX4 [PRS415-loxPWT-HHTS-loxPWT-HHFS-lopWT] | <2.56E-0.7 (5) |
| NAy236 | His3Δ200 leu2Δ1 lys2Δ202 trp1Δ63 ura3-52 hht1-hhf1Δ:: natMX4 hht2-hhf2Δ:: hygMX4 HO::loxPWT-HHTS-loxPWT-HHFS-lopWT-URA3 | <1.6E-07 (5) |
| NAy390 | leu2Δ0 met15Δ0 ura3Δ0 his3Δ1 RPC11::KanMX HO:SPAL2p-RPC11-GAL1t:LEU2 [pRS413-GEV] | 6.11E-06 (12) |
| NAy391 | leu2Δ0 met15Δ0 ura3Δ0 his3Δ1 RPC11::KanMX HO:SPAL5p-RPC11-GAL1t:LEU2 [pRS413-GEV] | 6.39E-06 (12) |
| NAy392 | leu2Δ0 met15Δ0 ura3Δ0 his3Δ1 RPC11::KanMX HO:SPAL6p-RPC11-GAL1t ::LEU2 [pRS413-GEV] | 8.57E-06 (12) |

*Mean reversion rate; n, Number of replicate experiments (in parentheses)

TABLE 3-continued

Differentially expressed genes in safeguard switches

| Safeguard | Promoter | Gene | Log2Fold Change | P-value | Adjusted P-value |
|---|---|---|---|---|---|
| | | BTN2 | -2.812 | $6.603 \cdot 10^{-11}$ | $2.190 \cdot 10^{-07}$ |
| | | ZPR1 | -2.168 | $2.056 \cdot 10^{-07}$ | $4.547 \cdot 10^{-04}$ |
| | | PDR12 | 2.271 | $3.575 \cdot 10^{06}$ | 0.005 |
| | | GCN1 | 1.945 | $3.843 \cdot 10^{-06}$ | 0.005 |
| | | YPR117W | 1.878 | $6.911 \cdot 10^{-06}$ | 0.008 |
| | | YKL031W | -2.026 | $1.006 \cdot 10^{-05}$ | 0.010 |
| HSP10 | GAL1 | LYS2 | -Inf | $1.005 \cdot 10^{-58}$ | $6.697 \cdot 10^{-55}$ |
| | | HO | 4.666 | $2.974 \cdot 10^{-36}$ | $9.914 \cdot 10^{-33}$ |
| | | MET17 | -Inf | $1.735 \cdot 10^{-25}$ | $3.856 \cdot 10^{-22}$ |
| | | SNR6 | -4.019 | $5.451 \cdot 10^{-14}$ | $9.084 \cdot 10^{-11}$ |
| | | BTN2 | -2.063 | $3.586 \cdot 10^{-11}$ | $4.781 \cdot 10^{-08}$ |
| | | ICY2 | -2.196 | $1.106 \cdot 10^{-10}$ | $1.228 \cdot 10^{-07}$ |
| | | PDR5 | -1.506 | $6.577 \cdot 10^{-07}$ | $6.263 \cdot 10^{-04}$ |
| | | YGR035C | -1.773 | $7.848 \cdot 10^{-07}$ | $6.539 \cdot 10^{-04}$ |
| | | HSP10 | 1.529 | $1.927 \cdot 10^{-06}$ | 0.001 |
| | | YLR346C | -1.560 | $6.564 \cdot 10^{-06}$ | 0.004 |
| | | COS8 | 2.258 | $9.962 \cdot 10^{-06}$ | 0.006 |
| | | ZPR1 | -1.327 | $1.316 \cdot 10^{-05}$ | 0.007 |

TABLE 5

GEV and Cre-EBD escape mutant analysis summary

| Revertant name | Escape mutant Type | Summary |
|---|---|---|
| NAy259 | GEV | A 831 bp in frame deletion in the hER and VP16 regions (between 2120 bp and 2950 bp); GAGC microhomology mediated; retains 14aa of VP16 |
| NAy261 | GEV | 528 bp deletion between 1967 bp and 2497 bp (hER region) GAGC microhomology mediated |
| NAy262 | GEV | 780 bp deletion between 1947 bp and 2726 bp (hER). |
| NAy263 | GEV | 4 bp insertion at 1078 bp: TACT (hER). Frameshift creates a C-terminus with several acidic residues |
| NAy264 | GEV | 807 bp deletion from 2001 bp to 2807 bp (hER) |
| R250-1* | Cre-EBD | Insertion of a TCC codon, increasing number of Leucine codons from L4 to L5 at aa571 |
| R250-3 | Cre-EBD | D329Y |
| R250-4 | Cre-EBD | Δ1437-1749 |

TABLE 5-continued

GEV and Cre-EBD escape mutant analysis summary

| Revertant name | Escape mutant Type | Summary |
|---|---|---|
| R250-10 | Cre-EBD | Δ514-819 |
| R250-25 | Cre-EBD | Insertion of 8 bp CAGTAGC at bp 2506 |
| R250-27 | Cre-EBD | Nonsense; E69(TAA) |
| R250-29 | Cre-EBD | Δ1390-1405 |
| R250-30 | Cre-EBD | S205R |
| R250-32 | Cre-EBD | 1792-2085 |
| R250-39 | Cre-EBD | T188I |

TABLE 6

SG strains promoters and escape rates.

| Essential Gene | Promoter | Escape rate* |
|---|---|---|
| FAS2 | SPAL5 | 6.6E−08 |
| HTS1 | SPAL6 | 7.0E−08 |
| RPB11 | SPAL5 | 1.9E−08 |
| SEC17 | SPAL2 | 8.8E−08 |
| SEC4 | SPAL2 | 6.5E−08 |

*Escape rates were calculated according to method of the median

TABLE 7

Transcript changes in SG strains.

| GS strain | Gene name | P-value | log2Fold Change | GS strain | Gene name | P-value | log2Fold Change |
|---|---|---|---|---|---|---|---|
| FAS2 MATa | ND | NA | NA | | PXA1 | 5.68E−28 | 2.4 |
| | | | | | ROG3 | 3.68E−27 | −2.36 |
| FAS2 MATα | RTN2 | 1.71E−84 | 2.24 | | BIO5 | 1.30E−26 | 2.33 |
| | FAS2 | 5.19E−76 | 2.09 | | PNS1 | 8.58E−26 | 2.3 |
| RPB11 MATa | SPS100 | 3.31E−61 | 3.86 | | ECI1 | 1.13E−25 | 2.29 |
| | RGI2 | 7.88E−41 | 3.01 | | YER121W | 4.16E−25 | 2.29 |
| | SPG1 | 7.86E−39 | 2.92 | | PHO89 | 2.57E−24 | 2.21 |
| | ADH2 | 1.57E−38 | 2.9 | | BOP2 | 1.09E−23 | 2.18 |
| | ADY2 | 2.18E−38 | 2.89 | | ARO10 | 2.79E−23 | 2.16 |
| | DCI1 | 3.79E−36 | 2.82 | | RPI1 | 4.56E−23 | 2.18 |
| | CYB2 | 1.33E−33 | 2.67 | | DMC1 | 5.98E−23 | 2.15 |
| | POX1 | 1.52E−33 | 2.68 | | STP4 | 8.70E−23 | −2.14 |
| | CTA1 | 4.07E−33 | 2.65 | | PUN1 | 3.26E−21 | 2.04 |
| | YKL065W-A | 1.26E−32 | 2.67 | | YAR029W | 4.40E−21 | −2.19 |
| | CIT3 | 8.30E−32 | 2.59 | | SLZ1 | 6.22E−21 | 2.04 |
| | tV(AAC) E2 | 2.84E−31 | −3.89 | | CYC7 | 6.69E−21 | −2.03 |
| | | | | | ENA1 | 7.01E−21 | 2.03 |
| | PHM7 | 4.12E−29 | 2.46 | | PX42 | 8.45E−21 | 2.02 |
| | CSM4 | 3.33E−28 | 2.44 | | TPO2 | 1.81E−20 | −2.01 |
| | RMA1 | 7.18E−20 | −2.06 | | RRT7 | 6.12E−06 | −2.87 |
| | YAR030C | 1.23E−17 | −2 | SEC4 MATa | ND | NA | NA |
| | RRT5 | 3.37E−12 | −2.32 | | | | |
| | PAU19 | 4.42E−08 | −2.41 | SEC4 MATα | RTN2 | 3.29E−70 | 2.51 |
| | SUF17 | 2.74E−06 | −3.13 | | HBT1 | 2.18E−61 | 2.32 |
| | SLZ1 | 6.22E−21 | 3.86 | | PFK27 | 6.22E−61 | −2.37 |
| | CYC7 | 6.69E−21 | 3.01 | | COM2 | 1.89E−50 | −2.09 |
| | ENA1 | 7.01E−21 | 2.92 | | HSP12 | 5.94E−50 | 2.06 |
| | PXA2 | 8.45E−21 | 2.9 | | TKL2 | 1.63E−49 | 2.06 |
| | TPO2 | 1.81E−20 | 2.89 | | CTT1 | 6.69E−49 | 2.04 |
| | RMA1 | 7.18E−20 | 2.82 | | | | |
| | YAR030C | 1.23E−17 | 2.67 | | | | |
| | RRT5 | 3.37E−12 | 2.68 | | | | |
| | PAU19 | 4.42E−08 | 2.65 | | | | |
| | SUF17 | 2.74E−06 | 2.67 | | | | |
| RPB11 MATα | OYE3 | 4.27E−70 | 2.42 | | | | |
| | GAL2 | 3.08E−62 | 2.05 | | | | |
| | YHR054C | 7.44E−08 | −2.41 | | | | |

TABLE 5-continued

GEV and Cre-EBD escape mutant analysis summary

| Revertant name | Escape mutant Type | Summary |
|---|---|---|
| R250-44 | Cre-EBD | 1313-2412 |
| R250-46 | Cre-EBD | Y324F |
| 250-47 | Cre-EBD | V204F/S205C |
| 250-48 | Cre-EBD | A131P |

TABLE 8

Escaper complementation group analysis

| GENE | | R/D* |
|---|---|---|
| FAS2 | Group 1: MATa (R1, R4, R5, R8) and MAT-α (R9, R10, R13, R14, R15) | R |
| | Group 2: MATa R2 | R |
| | Group 3: MAT a R3 | R |
| | Group 4: MATa R6 | R |
| | Group 5: MATa R7 | R |
| | Group 6: MATα R11 | R |
| | Group 7: MATα R12 | R |
| | Group 8: MATα R16 | R |
| RPB11 | Could not be determined | D |
| SEC4 | Group 1: MATa (R2, R4, R5, R6, R7) and | R |

TABLE 8-continued

Escaper complementation group analysis

| GENE | R/D* |
|---|---|
| MATα (R11, R12, R13, R15, R16) | |
| Group 2: MATa R1 | R |
| Group 3: MATa R3 | R |
| Group 4: MATa R8 | R |
| Group 5: MATα R9 | R |
| Group 6: MATα R10Group | R |
| Group 7: MATα R15 | R |
| | R |

*R = recessive, D = Dominant

TABLE 9

Genomic mutations found in escapers by DNAseq

| SG | Escaper | Gene | Mutation |
|---|---|---|---|
| FAS2 | R1 | UME6 | E75* |
| FAS2 | R2 | RPD3 | M1V |
| FAS2 | R3 | RPD3 | G312D |
| FAS2 | R6 | DEP1 | Y236* |
| FAS2 | R7 | YTA12 | T971A& |
| | | SDS3 | E71* |
| FAS2 | R11 | RHO1 | D129N& |
| | | SIN3 | 3061insT† |
| FAS2 | R12 | SIN3 | Y630* |
| FAS2 | R16 | DEP1 | Y242* |
| RPB11 | R9 | UME6 | C165* |
| SEC4 | R1 | RPD3 | G309C |
| SEC4 | R2 | UBP13 | L67M& |
| | | UME6 | Q113* |
| SEC4 | R3 | SDS3 | Q65* |
| SEC4 | R9 | SRL2 | K74L& |
| | | DEP1 | E222* |
| SEC4 | R10 | DEP1 | 512insC† |
| SEC4 | R14 | UME6 | W368* |

*Indicates premature stop codon;
†indicates frameshift;
&indicates assumed secondary mutation

TABLE 10

Decoy molecule properties

| Compound | Solvent | Conc. 1 | Conc. 2 |
|---|---|---|---|
| 1-Naphthaleneacetic acid | DMSO | 100 μM | 1 μM |
| 2,4-DAPG | DMSO | 20 μM | 1 μM |
| 3-oxo-octanoyl-L-homoserine (OAH) | DMSO | 100 μM | 1 μM |
| Bepridil | DMSO | 100 μM | 1 μM |
| Catechin | DMSO | 100 μM | 1 μM |
| Choline | Water | 100 μM | 1 μM |
| Coumestrol | DMSO | 100 μM | 1 μM |
| Cumate | Ethanol | 100 μM | 1 μM |
| D-camphor | DMSO | 100 μM | 1 μM |
| Daidzein | DMSO | 100 μM | 1 μM |
| Doxycycline | Water | 100 μM | 1 μM |
| Erythromycin | Ethanol | 100 μM | 1 μM |
| Estradiol | Ethanol | 30 μM | 1 μM |
| Fisetin | DMSO | 100 μM | 1 μM |
| Fusaric Acid | DMSO | 100 μM | 1 μM |
| Genistein | DMSO | 100 μM | 1 μM |
| Gentamycin | Water | 100 μM | 1 μM |
| IPTG | Water | 100 μM | 1 μM |
| kinetin | DMSO | 100 μM | 1 μM |
| Lincomycin | Water | 100 μM | 1 μM |
| Quercetin | DMSO | 100 μM | 1 μM |
| Sodium Salicylate | DMSO | 100 μM | 1 μM |

TABLE 11

Strain list

| Strain # | genotype | Origin |
|---|---|---|
| BY4741 | MATa leu2Δ0 met15Δ0 ura3Δ0 his3Δ1 | Brachmann et al., 1998 |
| BY4742 | MATα leu2Δ0 lys2Δ0 ura3Δ0 his3Δ1 | Brachmann et al., 1998 |
| BY4743 | MATa/MATα leu2Δ0/leu2Δ0 ura3Δ0/ura3Δ0 his3Δ1/his3Δ1 lys2Δ0/LYS MET15/met15Δ0 | Brachmann et al., 1998 |
| R1158 | MATa URA3::CMV-tTA MATa his3-1 leu2-0 met15-0 | Mnaimneh et al., 2004 |
| NAy395 | MATa leu2Δ0ura3Δ0 his3Δ1 lys2Δ0 FAS2::KanMX [pRS416-FAS2] | This disclosure |
| NAy396 | MATα leu2Δ0 lys2Δ0 ura3Δ0 his3Δ1 FAS2::KanMX [pRS416-FAS2] | This disclosure |
| NAy397 | MATa leu2Δ0 met15Δ0 ura3Δ0 his3Δ1 RPB11::KanMX [pRS416-RPB11] | This disclosure |
| NAy398 | MATα leu2Δ0 lys2Δ0 ura3Δ0 his3Δ1RPB11::KanMX [pRS416-RPB11] | This disclosure |
| NAy399 | MATa leu2Δ0 met15Δ0 ura3Δ0 his3Δ1 SEC4::KanMX [pRS416-SEC4] | This disclosure |
| NAy400 | MATα leu2Δ0 lys2Δ0 ura3Δ0 his3Δ1 SEC4::KanMX [pRS416-SEC4] | This disclosure |
| NAy407 | MATa leu2Δ0 met15Δ0 ura3Δ0 his3Δ1 FAS2::KanMX HO::SPAL5p-FAS2-GAL1t::LEU2 [pRS416-GEV] | This disclosure |
| NAy408 | MATα leu2Δ0 lys2Δ0 ura3Δ0 his3Δ1 FAS2::KanMX HO::SPAL5p-FAS2-GAL1t::LEU2 [pRS416-GEV] | This disclosure |
| NAy409 | MATa leu2Δ0 met15Δ0 ura3Δ0 his3Δ1 RPB11::KanMX HO::SPAL5p-RPB11-GAL1t::LEU2 [pRS416-GEV] | This disclosure |
| NAy410 | MATα leu2Δ0 lys2Δ0 ura3Δ0 his3Δ1 RPB11::KanMX HO::SPAL5p-RPB11-GAL1t::LEU2 [pRS416-GEV] | This disclosure |
| NAy411 | MATa leu2Δ0 met15Δ0 ura3Δ0 his3Δ1 SEC4::KanMX HO::SPAL2p-SEC4-GAL1t::LEU2 [pRS416-GEV] | This disclosure |

TABLE 11-continued

Strain list

| Strain # | genotype | Origin |
|---|---|---|
| NAy412 | MATα leu2Δ0 lys2Δ0 ura3Δ0 his3Δ1 SEC4::KanMX HO::SPAL2p-SEC4-GAL1t::LEU2 [pRS416-GEV] | This disclosure |
| NAy484 | MATa leu2Δ0 met15Δ0 ura3Δ0 his3Δ1 FAS2::KanMX HO::SPAZ4p-FAS2-GAL1t-LEU2[pRS413-Z4EV] | This disclosure |
| NAy486 | MATa leu2Δ0 met15Δ0 ura3Δ0 his3Δ1RPB11::KanMX HO::SPAZ4p-RPB11-GAL1t-LEU2[pRS413-Z4EV] | This disclosure |
| NAy488 | MATa leu2Δ0 met15Δ0 ura3Δ0 his3Δ1SEC4::KanMX HO::SPAZ4p-SEC4-GAL1t-LEU2[pRS413-Z4EV] | This disclosure |
| NAy497 | MATa leu2Δ0 met15Δ0 ura3Δ0 his3Δ1 HO::RFP-LEU2 [pRS413] | This disclosure |
| NAy471 | MATa leu2Δ0ura3Δ0 his3Δ1 lys2Δ0 SEC4::KanMX ChVI::SpHIS5-TETp-SEC4-GSH1t-CMVp-rtTA-STR1t | This disclosure |
| NAy472 | MATa leu2Δ0ura3Δ0 his3Δ1 lys2Δ0 SEC4::KanMX ChVI::SpHIS5-SPETp-SEC4-GSH1t-CMVp-rtTA-STR1t | This disclosure |
| NAy473 | MATa leu2Δ0ura3Δ0 his3Δ1 lys2Δ0 SEC4::KanMX ChVI::SpHIS5-3xSPETp-SEC4-GSH1t-CMVp-rtTA-STR1t | This disclosure |
| NAy474 | MATa leu2Δ0ura3Δ0 his3Δ1 lys2Δ0 SEC4::KanMX ChVI::SpHIS5-3xSPETp-SEC4-GSH1t-CMVp-rtTA-STR1t | This disclosure |

TABLE 12

Oligo list

| Oligo name | sequence | SEQ ID NO: |
|---|---|---|
| ADE13_TU_F | cccccctcgaggtcgacggtatcgataagcttgatatcgaattcctgcagTGGTTTACCACTAACAAGAAAAGAA | 11 |
| ARC35_TU_F | cccccctcgaggtcgacggtatcgataagcttgatatcgaattcctgcagTGCATATATACCGGGTGAGGGCCAC | 12 |
| CDC42_TU_F | cccccctcgaggtcgacggtatcgataagcttgatatcgaattcctgcagTTTTTAAAAAAGTTGCATTATTTC | 13 |
| DED1_TU_F | cccccctcgaggtcgacggtatcgataagcttgatatcgaattcctgcagTCTTGCGAGATGATCCCGCATTTTC | 14 |
| EMW1_TU_F | cccccctcgaggtcgacggtatcgataagcttgatatcgaattcctgcagGTCACAGGTGTCAAGGTGTTAACTC | 15 |
| ERG1_TU_F | cccccctcgaggtcgacggtatcgataagcttgatatcgaattcctgcagTGAGCGTGGTTCAGGGCACTCTACG | 16 |
| ERG25_TU_F | cccccctcgaggtcgacggtatcgataagcttgatatcgaattcctgcagACTACCACTGCCTCCCTTCGTATAC | 17 |
| ERO1_TU_F | cccccctcgaggtcgacggtatcgataagcttgatatcgaattcctgcagACGAGATCATTTTCTTATCTATCTA | 18 |
| FAS2_TU_F | cccccctcgaggtcgacggtatcgataagcttgatatcgaattcctgcagAACTATTTTCTATATTTCTATTCTA | 19 |
| GRC3_TU_F | cccccctcgaggtcgacggtatcgataagcttgatatcgaattcctgcagTTGTTGCGCACTAGGTACGATTTCC | 20 |
| HSP10_TU_F | cccccctcgaggtcgacggtatcgataagcttgatatcgaattcctgcagTATTTTATTACGGTTCAGCAAAGGC | 21 |
| HTS1_TU_F | cccccctcgaggtcgacggtatcgataagcttgatatcgaattcctgcagACAGATCCTTTATAATGTAGTAATT | 22 |
| ADE13_TU_R | aaaagctggagctccaccgcggtggcggccgctctagaactagtggatccAAAATCCGTAAGCCAAAAAAACAAG | 23 |
| ARC35_TU_R | aaaagctggagctccaccgcggtggcggccgctctagaactagtggatccAGAGAGGGCGTTGTTCCTCCTGTAG | 24 |
| CDC42_TU_R | aaaagctggagctccaccgcggtggcggccgctctagaactagtggatccGAACGTTTGGGGCTTGACGGCTCGA | 25 |
| DED1_TU_R | aaaagctggagctccaccgcggtggcggccgctctagaactagtggatccTAAAAAATAAGAGTGGAAAAAAGT | 26 |
| EMW1_TU_R | aaaagctggagctccaccgcggtggcggccgctctagaactagtggatccTAAAGAAAAGGCAAGAAGATTTTGA | 27 |
| ERG1_TU_R | aaaagctggagctccaccgcggtggcggccgctctagaactagtggatccAAAGTATAAAACACTTCGGTTAATA | 28 |
| ERG25_TU_R | aaaagctggagctccaccgcggtggcggccgctctagaactagtggatccATATAGTTTTTAGAATTAACCTGAA | 29 |
| ERO1_TU_R | aaaagctggagctccaccgcggtggcggccgctctagaactagtggatccCAATGAGGAGTGATTTTACACAAAA | 30 |
| FAS2_TU_R | aaaagctggagctccaccgcggtggcggccgctctagaactagtggatccTGTGGGCCGACCAAATAGAAGAATT | 31 |
| GRC3_TU_R | aaaagctggagctccaccgcggtggcggccgctctagaactagtggatccGGGTTTAACGGAGGAGATGAAGGAT | 32 |
| HSP10_TU_R | aaaagctggagctccaccgcggtggcggccgctctagaactagtggatccATAGTTTGTACACATAGTGTCCCTA | 33 |

TABLE 12-continued

Oligo list

| Oligo name | sequence | SEQ ID NO: |
|---|---|---|
| HTS1_TU_R | aaaagctggagctccaccgcggtggcggccgctctagaactagtggatccTGAGCAGACTGGAAAAGATGTAATG | 34 |
| ILV5_TU_F | ccccccctcgaggtcgacggtatcgataagcttgatatcgaattcctgcagCGCTGTCACTGAACTAAAACAATAA | 35 |
| IPI3_TU_F | ccccccctcgaggtcgacggtatcgataagcttgatatcgaattcctgcagCTTTGATAAATTAATACGGTAAGAT | 36 |
| IQG1_TU_F | ccccccctcgaggtcgacggtatcgataagcttgatatcgaattcctgcagGAAAAATTGCAAAATTTTGATAGAG | 37 |
| MRD1_TU_F | ccccccctcgaggtcgacggtatcgataagcttgatatcgaattcctgcagGTAGACATGATGTACTATACAACCA | 38 |
| MTR2_TU_F | ccccccctcgaggtcgacggtatcgataagcttgatatcgaattcctgcagTTCTTTTCTTAGAAGAGGTTTTGTT | 39 |
| NAB3_TU_F | ccccccctcgaggtcgacggtatcgataagcttgatatcgaattcctgcagTAATCTTCGCTACTTCAAGTTTCAT | 40 |
| NDC1_TU_F | ccccccctcgaggtcgacggtatcgataagcttgatatcgaattcctgcagCGCTCATCCAAAAAATCGATAACTA | 41 |
| NOC4_TU_F | ccccccctcgaggtcgacggtatcgataagcttgatatcgaattcctgcagCAACAAAAGAATGAAAGAAAAAAGA | 42 |
| NRD1_TU_F | ccccccctcgaggtcgacggtatcgataagcttgatatcgaattcctgcagGAAAGTCGGCGGCAAAAATAAATGT | 43 |
| PGA1_TU_F | ccccccctcgaggtcgacggtatcgataagcttgatatcgaattcctgcagTTAGCTGCTCTATTTATATTTGAAG | 44 |
| POL1_TU_F | ccccccctcgaggtcgacggtatcgataagcttgatatcgaattcctgcagTACATGAACTGACCGAAATTGCAGC | 45 |
| POP6_TU_F | ccccccctcgaggtcgacggtatcgataagcttgatatcgaattcctgcagGCTTCCCTTCATCCCCAGTTTTTAC | 46 |
| ILV5_TU_R | aaaagctggagctccaccgcggtggcggccgctctagaactagtggatccCATTGAATCATAATAAATATGTAAA | 47 |
| IPI3_TU_R | aaaagctggagctccaccgcggtggcggccgctctagaactagtggatccACTAAAGGCGGCCCATATTCTGAGA | 48 |
| IQG1_TU_R | aaaagctggagctccaccgcggtggcggccgctctagaactagtggatccACATCTTATTTTTATCTACTGAAGA | 49 |
| MRD1_TU_R | aaaagctggagctccaccgcggtggcggccgctctagaactagtggatccAACAAGATGTGCTAACATTTTCCAT | 50 |
| MTR2_TU_R | aaaagctggagctccaccgcggtggcggccgctctagaactagtggatccTTAGGGACCGCCAGGGACCATGATT | 51 |
| NAB3_TU_R | aaaagctggagctccaccgcggtggcggccgctctagaactagtggatccAGTTTTTCGTTCTGAAAGAGATGCA | 52 |
| NDC1_TU_R | aaaagctggagctccaccgcggtggcggccgctctagaactagtggatccTCTCTATACTTTTCTTTACTATTAT | 53 |
| NOC4_TU_R | aaaagctggagctccaccgcggtggcggccgctctagaactagtggatccTAACGCGGGGATCAGCGGTTCGATC | 54 |
| NRD1_TU_R | aaaagctggagctccaccgcggtggcggccgctctagaactagtggatccCTTGAAAAAAAACCAGGAATACGGT | 55 |
| PGA1_TU_R | aaaagctggagctccaccgcggtggcggccgctctagaactagtggatccATTCAGTTTAGTTAAATCTGGGTTA | 56 |
| POL1_TU_R | aaaagctggagctccaccgcggtggcggccgctctagaactagtggatccATGATGCATGTGAGAACTGATCACC | 57 |
| POP6_TU_R | aaaagctggagctccaccgcggtggcggccgctctagaactagtggatccTGAATTTCCGATTTCCAAAGGGAAG | 58 |
| PRE6_TU_F | ccccccctcgaggtcgacggtatcgataagcttgatatcgaattcctgcagAGAAATTATATATAAATATACTTCT | 59 |
| PSA1_TU_F | ccccccctcgaggtcgacggtatcgataagcttgatatcgaattcctgcagCGTGTACTTGCTGGCCAGCTAGAAA | 60 |
| RFT1_TU_F | ccccccctcgaggtcgacggtatcgataagcttgatatcgaattcctgcagGCATCTTTCGATACCTTAGCACTCG | 61 |
| RIO1_TU_F | ccccccctcgaggtcgacggtatcgataagcttgatatcgaattcctgcagCGATTGTTCGCCGGTGTTATAACTT | 62 |
| RNA1_TU_F | ccccccctcgaggtcgacggtatcgataagcttgatatcgaattcctgcagCTAATCCACTGCCGGCAGAATTTCC | 63 |
| RPB11_TU_F | ccccccctcgaggtcgacggtatcgataagcttgatatcgaattcctgcagCGTTTGCTGAAGAACTGCAAAATGA | 64 |
| RPC11_TU_F | ccccccctcgaggtcgacggtatcgataagcttgatatcgaattcctgcagGTTAAAGAACTCTTCAATATTCGTC | 65 |
| RPN8_TU_F | ccccccctcgaggtcgacggtatcgataagcttgatatcgaattcctgcagTAAGGTAAGGCATCATTAGCAGGAT | 66 |
| RPT4_TU_F | ccccccctcgaggtcgacggtatcgataagcttgatatcgaattcctgcagAGGTCTATTACCGATGGGCAAAAGA | 67 |
| SDA1_TU_F | ccccccctcgaggtcgacggtatcgataagcttgatatcgaattcctgcagACTGCTGATAGTGTCAAGAACATGT | 68 |
| SEC11_TU_F | ccccccctcgaggtcgacggtatcgataagcttgatatcgaattcctgcagTATAGCAACCTCGTTGACATTGTGA | 69 |
| SEC14_TU_F | ccccccctcgaggtcgacggtatcgataagcttgatatcgaattcctgcagGCCGTACGTGTCGTCTGATCTCCAA | 70 |

TABLE 12-continued

Oligo list

| Oligo name | sequence | SEQ ID NO: |
|---|---|---|
| PRE6_TU_R | aaaagctggagctccaccgcggtggcggccgctctagaactagtggatccAAGTCATTCCATTCCATTCTATATC | 71 |
| PSA1_TU_R | aaaagctggagctccaccgcggtggcggccgctctagaactagtggatccGTTACATAAGGATCAACCTTTTTTT | 72 |
| RFT1_TU_R | aaaagctggagctccaccgcggtggcggccgctctagaactagtggatccTTTACGGTGAAATAGCTTCTCTCTT | 73 |
| RIO1_TU_R | aaaagctggagctccaccgcggtggcggccgctctagaactagtggatccGGATTGATTTCACTAAAAATCAAGA | 74 |
| RNA1_TU_R | aaaagctggagctccaccgcggtggcggccgctctagaactagtggatccATGCTGTTTTTGCTTGGCTTCTTA | 75 |
| RPB11_TU_R | aaaagctggagctccaccgcggtggcggccgctctagaactagtggatccCATGGCTGGTTTTTTTCTTTTTTT | 76 |
| RPC11_TU_R | aaaagctggagctccaccgcggtggcggccgctctagaactagtggatccAAAAATATTAATTATTGCGTCCTAT | 77 |
| RPN8_TU_R | aaaagctggagctccaccgcggtggcggccgctctagaactagtggatccCGTTAATATAAACTTATGTATATTC | 78 |
| RPT4_TU_R | aaaagctggagctccaccgcggtggcggccgctctagaactagtggatccAATTGAAACTACGTACCTGAAAGAA | 79 |
| SDA1_TU_R | aaaagctggagctccaccgcggtggcggccgctctagaactagtggatccGGGAAAAGCCGAGAATTCCCGATGA | 80 |
| SEC11_TU_R | aaaagctggagctccaccgcggtggcggccgctctagaactagtggatccAAAAAATGACACAAATCATCTCTGT | 81 |
| SEC14_TU_R | aaaagctggagctccaccgcggtggcggccgctctagaactagtggatccATAATCTAATAGCTGAGTGGAAGAA | 82 |
| SEC17_TU_F | ccccccctcgaggtcgacggtatcgataagcttgatatcgaattcctgcagTTCTTTGTCAATTGCATCTCTAGTT | 83 |
| SEC4_TU_F | ccccccctcgaggtcgacggtatcgataagcttgatatcgaattcctgcagAGTTCGATAGAGCATCTTTCAATAC | 84 |
| SLY1_TU_F | ccccccctcgaggtcgacggtatcgataagcttgatatcgaattcctgcagTGGACTTGAACATAGGTGATTCTTG | 85 |
| SRP68_TU_F | ccccccctcgaggtcgacggtatcgataagcttgatatcgaattcctgcagGATGTACTTCCCGCCATACAAATAT | 86 |
| SSU72_TU_F | ccccccctcgaggtcgacggtatcgataagcttgatatcgaattcctgcagAAAGATGCAAGCAATAATGAAAATC | 87 |
| SU11_TU_F | ccccccctcgaggtcgacggtatcgataagcttgatatcgaattcctgcagTTTCTATTGTTTCACTATTCTTTAT | 88 |
| TRS20_TU_F | ccccccctcgaggtcgacggtatcgataagcttgatatcgaattcctgcagATTCTCACCCTGTCTGCTTTTATTC | 89 |
| UFD1_TU_F | ccccccctcgaggtcgacggtatcgataagcttgatatcgaattcctgcagTTCCTCATCTTGAATCAAATGCTTA | 90 |
| UTP11_TU_F | ccccccctcgaggtcgacggtatcgataagcttgatatcgaattcctgcagGAGTTCAGAACCGTGACCTTTATTC | 91 |
| UTP20_TU_F | ccccccctcgaggtcgacggtatcgataagcttgatatcgaattcctgcagGTTCGAGTCCTGCAGTTGTCGTTAT | 92 |
| UTP22_TU_F | ccccccctcgaggtcgacggtatcgataagcttgatatcgaattcctgcagAGTTCTGTCCATCCGGTGGGCGACC | 93 |
| UTP5_TU_F | ccccccctcgaggtcgacggtatcgataagcttgatatcgaattcctgcagTGCACGATAGAAATCGACAAGGCGA | 94 |
| SEC17_TU_R | aaaagctggagctccaccgcggtggcggccgctctagaactagtggatccCACGAACAAAGGTTTATTGCGCTTG | 95 |
| SEC4_TU_R | aaaagctggagctccaccgcggtggcggccgctctagaactagtggatccTAGATAATATAAAAGTGACATCTAA | 96 |
| SLY1_TU_R | aaaagctggagctccaccgcggtggcggccgctctagaactagtggatccGCCTAAAGCACATTTCATAAATAAA | 97 |
| SRP68_TU_R | aaaagctggagctccaccgcggtggcggccgctctagaactagtggatccTAATTTAACGTATAGTTATGTAAAG | 98 |
| SSU72_TU_R | aaaagctggagctccaccgcggtggcggccgctctagaactagtggatccTTCTTGATAAAAAAATAGCTATGTG | 99 |
| SUI1_TU_R | aaaagctggagctccaccgcggtggcggccgctctagaactagtggatccACTTGTTCTTATATCTCTGTATGTA | 100 |
| TRS20_TU_R | aaaagctggagctccaccgcggtggcggccgctctagaactagtggatccTGTAACGGAACACTCAAAAGTGACT | 101 |
| UFD1_TU_R | aaaagctggagctccaccgcggtggcggccgctctagaactagtggatccGGTAAACGAAGAGAATTACTTCGGC | 102 |
| UTP11_TU_R | aaaagctggagctccaccgcggtggcggccgctctagaactagtggatccACAAATCTTGTCCTAAATACTCCCA | 103 |
| UTP20_TU_R | aaaagctggagctccaccgcggtggcggccgctctagaactagtggatccACTGGTATGTCTTTTATCTAACAGT | 104 |
| UTP22_TU_R | aaaagctggagctccaccgcggtggcggccgctctagaactagtggatccACCTAGCTTTATTCTGAGCGTCGCC | 105 |
| UTP5_TU_R | aaaagctggagctccaccgcggtggcggccgctctagaactagtggatccAACGATGCCAGATGCAGTTCAAAAA | 106 |

TABLE 13

Essential genes

| Standard Gene Name | Systematic Gene Name | Transcript Accession number | Protein Accession number |
|---|---|---|---|
| ADE13 | YLR359W | NM_001182248.1 | NP_013463.1 |
| ARC35 | YNR035C | NM_001183212.1 | NP_014433.1 |
| CDC42 | YLR229C | NM_001182116.1 | NP_013330.1 |
| DED1 | YOR204W | NM_001183623.3 | NP_014847.3 |
| EMW1 | YNL313C | NM_001183151.1 | NP_014086.1 |
| ERG1 | YGR175C | NM_001181304.1 | NP_011691.1 |
| ERG25 | YGR060W | NM_001181189.3 | NP_011574.3 |
| ERO1 | YML130C | NM_001182493.1 | NP_013576.1 |
| FAS2 | YPL231W | NM_001184045.1 | NP_015093.1 |
| GRC3 | YLL035W | NM_001181855.1 | NP_013065.1 |
| HSP10 | YOR020C | NM_001183439.1 | NP_014663.1 |
| HTS1 | YPR033C | NM_001184130.1 | NP_015358.1 |
| ILV5 | YLR355C | NM_001182244.1 | NP_013459.1 |
| IPI3 | YNL182C | NM_001183020.1 | NP_014217.1 |
| IQG1 | YPL242C | NM_001184056.1 | NP_015082.1 |
| MRD1 | YPR112C | NM_001184269.1 | NP_015437.1 |
| MTR2 | YKL186C | NM_001179752.1 | NP_012735.1 |
| NAB3 | YPL190C | NM_001184004.1 | NP_015134.1 |
| NDC1 | YML031W | NM_001182389.1 | NP_013681.1 |
| NOC4 | YPR144C | NM_001184241.1 | NP_015470.1 |
| NRD1 | YNL251C | NM_001183089.1 | NP_014148.1 |
| PGA1 | YNL158W | NM_001182996.1 | NP_014241.1 |
| POL1 | YNL102W | NM_001182940.3 | NP_014297.3 |
| POP6 | YGR030C | NM_001181159.1 | NP_011544.1 |
| PRE6 | YOL038W | NM_001183292.1 | NP_014604.1 |
| PSA1 | YDL055C | NM_001180114.1 | NP_010228.1 |
| RFT1 | YBL020W | NM_001178260.1 | NP_009533.1 |
| RIO1 | YOR119C | NM_001183538.3 | NP_014762.3 |

TABLE 13-continued

Essential genes

| Standard Gene Name | Systematic Gene Name | Transcript Accession number | Protein Accession number |
|---|---|---|---|
| RNA1 | YMR235C | NM_001182742.1 | NP_013962.1 |
| RPB11 | YOL005C | NM_001183259.1 | NP_014638.1 |
| RPC11 | YDR045C | NM_001180353.1 | NP_010330.1 |
| RPN8 | YOR261C | NM_001183680.3 | NP_014904.3 |
| RPT4 | YOR259C | NM_001183678.3 | NP_014902.3 |
| SDA1 | YGR245C | NM_001181374.3 | NP_011761.3 |
| SEC11 | YIR022W | NM_001179544.1 | NP_012288.1 |
| SEC14 | YMR079W | NM_001182578.1 | NP_013796.1 |
| SEC17 | YBL050W | NM_001178290.1 | NP_009503.1 |
| SEC4 | YFL005W | NM_001179961.1 | NP_116650.1 |
| SLY1 | YDR189W | NM_001180497.1 | NP_010475.1 |
| SRP68 | YPL243W | NM_001184057.1 | NP_015081.1 |
| SSU72 | YNL222W | NM_001183060.1 | NP_014177.1 |
| SUI1 | YNL244C | NM_001183082.1 | NP_014155.1 |
| TRS20 | YBR254C | NM_001178602.1 | NP_009813.1 |
| UFD1 | YGR048W | NM_001181177.1 | NP_011562.1 |
| UTP11 | YKL099C | NM_001179665.1 | NP_012823.2 |
| UTP20 | YBL004W | NM_001178244.1 | NP_009551.2 |
| UTP22 | YGR090W | NM_001181219.3 | NP_011604.3 |
| UTP5 | YDR398W | NM_001180706.1 | NP_010686.1 |
| VAS1 | YGR094W | NM_001181223.1 | NP_011608.1 |

While the disclosure has been particularly shown and described with reference to specific embodiments, it should be understood by those having skill in the art that various changes in form and detail may be made therein without departing from the spirit and scope of the present disclosure.

What is claimed is:

1. A modified microorganism, the growth of which can be controlled by exogenously provided first and second compounds, the modified microorganism having genetic alterations comprising:
   i) a promoter inducible by the first compound, wherein the inducible promoter is operably linked to an RNA coding sequence, expression of which is essential for growth of the microorganism, wherein the RNA coding sequence does not encode an auxotrophic marker;
   ii) a pair of site specific recombinase recognition sites (SSRRS) flanking or within the RNA coding sequence such that recombination between the SSRRS disrupts expression of the RNA coding sequence; and iii) a site specific recombinase (SSR) coding region, wherein the SSR is specific for the SSRRS, and wherein expression of the SSR is repressed by the second compound;
   wherein the modified microorganism is in an in vitro culture comprising a culture medium, wherein the culture medium comprises a sub-micromolar concentration of the first and/or second compounds, and wherein the culture medium comprises a greater than sub-micromolar concentration of at least one decoy compound.

2. The modified microorganism of claim 1, wherein a) the promoter is inducible by a sub-micromolar concentration of the first compound, or b) wherein the expression of the SSR is repressible by or inhibited by a sub-micromolar concentration of the second compound, or both a) and b).

3. The modified microorganism of claim 1, wherein the modified microorganism has the same or an enhanced growth rate relative to a microorganism of the same type that does not comprise the genetic alterations.

4. The modified microorganism of claim 1, further comprising at least one decoy RNA coding sequence or other decoy genetic element introduced into the microorganism, wherein if the decoy RNA coding sequence is present and expressed its expression is not affected by the first or the second compound.

5. The modified microorganism of claim 1, wherein the modified microorganism is a pathogenic microorganism.

6. A kit for use in controlling growth of a microorganism of claim 1, the kit comprising a plurality of compounds, wherein the plurality of compounds includes the first and second compounds and the at least one decoy compound, wherein the at least one decoy compound is included in a molar excess relative to the first and second compounds.

7. The kit of claim 6, further comprising at least 2, 3, 4 or 5 additional decoy compounds, wherein the additional decoy compounds are each included in a molar excess relative to the first and second compounds.

8. The kit of claim 6, further comprising a microorganism of claim 1.

9. The kit of claim 6, further comprising a growth medium.

10. A method for controlling growth of a population of microorganisms of claim 1, comprising culturing the population of microorganisms in a culture medium that comprises a sub-micromolar concentration of the first and second compounds, wherein the first and second compounds are added to the culture medium in a composition that comprises the at least one decoy compound, wherein the at least one decoy compound is included in a molar excess relative to the first and second compounds, and wherein the at least one decoy compound does not retard the growth of the microorganisms in the population.

11. The method of claim 10, wherein the population of microorganisms comprises pathogenic microorganisms.

* * * * *